US007161031B2

(12) United States Patent  
Reddy et al.

(10) Patent No.: US 7,161,031 B2
(45) Date of Patent: Jan. 9, 2007

(54) AMINO-SUBSTITUTED SULFONANILIDES AND DERIVATIVES THEREOF FOR TREATING PROLIFERATIVE DISORDERS

(75) Inventors: E. Premkumar Reddy, Villanova, PA (US); M.V. Ramana Reddy, Upper Darby, PA (US); Stanley C. Bell, Narberth, PA (US)

(73) Assignees: Temple University - Of The Commonwealth System of Higher Education, Philadelphia, PA (US); Onconova Therapeutics, Inc., Lawrenceville, NJ (US)

( * ) Notice: Subject to any disclaimer, the term of this patent is extended or adjusted under 35 U.S.C. 154(b) by 298 days.

(21) Appl. No.: 10/505,998

(22) PCT Filed: Feb. 28, 2003

(86) PCT No.: PCT/US03/06358

§ 371 (c)(1),
(2), (4) Date: Aug. 27, 2004

(87) PCT Pub. No.: WO03/072063

PCT Pub. Date: Sep. 4, 2003

(65) Prior Publication Data

US 2005/0096484 A1   May 5, 2005

Related U.S. Application Data

(60) Provisional application No. 60/360,710, filed on Feb. 28, 2002.

(51) Int. Cl.
*C07C 307/02* (2006.01)
*A01N 41/06* (2006.01)
*C07K 17/06* (2006.01)

(52) U.S. Cl. .................. 564/84; 564/85; 564/86; 564/87; 564/88; 564/89; 564/90; 564/91; 564/92; 564/93; 514/601; 514/602; 514/603; 514/604; 530/402; 530/403; 530/404; 530/405

(58) Field of Classification Search .................. None
See application file for complete search history.

(56) References Cited

U.S. PATENT DOCUMENTS

| 2,531,367 | A | 11/1950 | Sprague | 260/518 |
|---|---|---|---|---|
| 4,035,421 | A | 7/1977 | Snyder, Jr. | 260/556 |
| 4,258,058 | A | 3/1981 | Witte et al. | 424/309 |
| 5,302,724 | A | 4/1994 | Howbert et al. | 548/452 |
| 5,780,483 | A | 7/1998 | Widdowson et al. | 514/311 |
| 5,880,151 | A | 3/1999 | Medina et al. | 514/518 |
| 5,886,044 | A | 3/1999 | Widdowson et al. | 514/596 |
| 6,121,304 | A | 9/2000 | Flygare et al. | 514/403 |
| 6,191,170 | B1 | 2/2001 | Medina | 514/604 |
| 6,262,113 | B1 | 7/2001 | Widdowson et al. | 514/522 |
| 6,359,013 | B1 | 3/2002 | Reddy et al. | 514/710 |
| 6,486,210 | B1 | 11/2002 | Reddy et al. | 514/708 |
| 6,541,475 | B1 | 4/2003 | Reddy et al. | 514/252.12 |
| 6,548,553 | B1 | 4/2003 | Reddy et al. | 514/710 |
| 6,586,617 | B1 | 7/2003 | Tabuchi et al. | 558/394 |
| 6,599,932 | B1 | 7/2003 | Reddy et al. | 514/438 |
| 6,646,009 | B1 | 11/2003 | Reddy et al. | 514/604 |
| 6,656,973 | B1 | 12/2003 | Cosenza et al. | 514/710 |
| 6,667,346 | B1 | 12/2003 | Reddy et al. | 514/710 |
| 6,762,207 | B1 | 7/2004 | Reddy et al. | 514/709 |
| 6,767,926 | B1 | 7/2004 | Cosenza et al. | 514/710 |
| 6,787,667 | B1 | 9/2004 | Reddy et al. | 562/429 |
| 7,053,123 | B1 | 5/2006 | Reddy et al. | 514/710 |
| 7,056,953 | B1 | 6/2006 | Reddy et al. | 514/710 |
| 2005/0130942 | A1 | 6/2005 | Reddy et al. | 514/114 |

FOREIGN PATENT DOCUMENTS

| DE | 2118493 | 10/1972 |
|---|---|---|
| JP | 04202173 | 7/1992 |
| WO | WO 95/24190 | 9/1995 |
| WO | WO 00/17159 | 3/2000 |
| WO | WO 02/067865 | 9/2002 |

OTHER PUBLICATIONS

CA:78:15764m, "2-Aminostilbenes", abstracting Ger. Offen., 2,118,493 (Oct. 26, 1972).
Waldau and Putter, "Biaryls, Stilbenes, Benzo[c]Cinnolines, And Dibenz [c,mn] Acridines From Sulfonamides", *Agnew. Chem., Int., Ed. Engl.* 11(9), 826-8 (1972).
J.E. Oliver and A.B. DeMilo, "A Knoevenagel-Type Of Styrene-Sul-Fonanilides", *Synthesis*, 321-322 (1975).
B. Aswarthamma, et al., "Synthesis And Spectral Studies Of Some Trans-1 (Aryl)-2- (Anilinesulphonly) Ethylenes (Styrene-ω-Sulphonanilides)", *Chimica Acta Turcica* 24 (1996), pp. 7-10.
A. Touati, et al., "Synthese De Sulfonamides, Sulfonates Et Thiosulfonates, Inhibiteurs De L'alcool Conferylique Deshydrogenase", *J.Soc.Alger.Chim.*, 1996, 6(1), pp. 39-52.
P. Wipf, et al., "Sulfonylated Aminothiazoles As New Small Molecule Inhibitors Of Protein Phosphatases", *Bioorganic & Medicinal Chemistry Letters* 11 (2001) pp. 313-317.
Patent Abstracts of Japan, Abstract of JP04202173. (1992).
A. DeMilo, "Sulfonamide Insect Chemosterilants", *J. Agr. Food Chem.*, 1974, 22(2), 197-99.
C. R. A. Godfrey et al., "A Novel Route to Unsymmetrical Stilbene Derivatives via Intramolecular Free Radical *ipso* Substitution Reactions", *Tetrahedron Lett.*, 1998, 39, 723-26.

(Continued)

*Primary Examiner*—Brian Davis
(74) *Attorney, Agent, or Firm*—Drinker Biddle & Reath LLP; Daniel A. Monaco

(57) ABSTRACT

Compounds useful as antiproliferative agents, including, for example, anticancer agents, are provided according to formula I: wherein: Ar, X, $X^1$, g, R and $R^3$ are as defined herein.

77 Claims, No Drawings

OTHER PUBLICATIONS

S. Hartig, "Über einige Derivate der β-Styrolsulfonsäure", *Journal für praktische Chemie*, 1966, 33(3-4): 215-24.

*Chem. Abs.* 66:18556, abstracting S. Hartig, "Über einige Derivate der β-Styrolsulfonsäure", *Journal für praktische Chemie*, 1966, 33(3-4): 215-24.

G. Manecke et al., "Polymere Hydrochinonsulfonamide", *Die Makromolekulare Chemie*, 1971, 145, 53-66.

*Chem. Abs.* 75:98861, abstracting G. Manecke, et al., "Polymere Hydrochinonsulfonamide", *Die Makromolekulare Chemie*, 1971, 145, 53-66.

K. Okuma, et al., "Reactions of (Aryloxy)oxosulfonium Ylides with Carbonyl Compounds", *J. Org. Chem.*, 1984, 49, 1402-07.

D. M. Purohit et al., "Synthesis and Antimicrobial Activity of Sulfonamides, Imidazolinones, N', N"-Diarylphosphinic Amide Derivatives with Potent "Dichloran" Moiety", *Ind. J. Het. Chem.*, 1998, 8, 67-70.

A. Touati, et al. "Synthèse de sulfonamides, sulfonates et thiosulfonates, inhibiteurs de l'alcool coniférylique déhydrogénase", *J. Soc. Alger. Chim.*, 1996, 6(1), 39-52.

W. E. Truce, et al., "Cyclopropanesulfonic Acid Esters and Amides", 1968, 33(10), 3849-51.

AMINO-SUBSTITUTED SULFONANILIDES AND DERIVATIVES THEREOF FOR TREATING PROLIFERATIVE DISORDERS

This application is a 371 of PCT/US03/06358 filed Feb. 28, 2003.

FIELD OF THE INVENTION

The invention relates to compositions and methods for the treatment of proliferative disorders, including but not limited to cancer.

BACKGROUND OF THE INVENTION

α-β-Unsaturated Sulfonamides

Cancer remains a leading-cause of mortality in the United States and in the world. To be useful, a new chemotherapeutic agent should have a wide spectrum of activity and significant therapeutic index. Styrene-ω-sulfonanilide has been prepared by reacting styrylsulfonyl chloride with aniline (Bordwell et al., *J. Amer. Chem. Soc.* 68:139, 1946). This and certain other styrene-ω-sulfonanilides have been prepared by Knoevenagel-type synthesis as possible chemosterilants against the common house fly *Musca domestica* L. (Oliver et al., *Synthesis* 321–322, 1975).

U.S. Pat. No. 4,035,421 to Snyder, Jr. describes the preparation of N-(3,4-dichlorophenyl)-2-phenylethenesulfonamide and its use as an antibacterial agent.

The styrene-ω-sulfonanilides 3'-hydroxy-4-nitrostyrene-β-sulfonanilide, 3'-hydroxy-2-nitrostyrene-β-sulfonanilide and 5'-hydroxy-2'-methyl-4-nitrostyrene-β-sulfonanilide were utilized as intermediates in the preparation of certain stilbenes by Waldau et al. *Angew. Chem., Int. Ed. Engl.* 11(9):826–8 (1972). The styrene-ω-sulfonanilides 3'-hydroxy-3-nitrostyrene-β-sulfonanilide and 5'-hydroxy-2'-methyl-4-nitrostyrene-β-sulfonanilide have been utilized in the preparation of stilbenes used as dyes (DE 2118493-Farbenfab AG).

Aswarthamma et al., *Chimica Acta Turcica* 24:7–10 (1996) disclose the preparation of certain trans-(1-aryl-(2-anilinesulphonyl)ethylenes. No biological activity is set forth for the compounds. Touarti et al., *J. Soc. Alger. Chim.* 6(1):39–52 (1996) disclose the preparation of certain α,β-unsaturated sulfonamides for inhibition of coniferyl alcohol dehydrogenase (CADH).

Except for the isolated teaching of antibacterial activity of N-(3,4-dichlorophenyl)-2-phenylethenesulfonamide, no useful pharmaceutical activity has been proposed for the limited numbers of α,β-unsaturated sulfonamides known to the prior art. In particular, no anti-cell proliferation or anticancer utility has been proposed for this class of compounds.

New cell antiproliferative agents, and anticancer therapeutics in particular, are needed which are useful in inhibiting proliferation of and/or killing cancer cells. In particular, such agents are needed which are selective in the killing of proliferating cells such as tumor cells, but not normal cells. Antineoplasitc agents are needed which are effective against a broad range of tumor types.

SUMMARY OF THE INVENTION

It is an object of the invention to provide compounds, compositions and therapeutic methods. The biologically active compounds are in the form of amino substituted sulfonanilides, and salts thereof.

It is an object of the invention to provide compounds, compositions and methods for the treatment of cancer and other proliferative diseases.

It is an object of the invention to provide compounds which are selective in killing tumor cells but not normal cells.

It is an object of the invention to provide compounds, compositions and methods for inducing neoplastic cells to selectively undergo apoptosis.

In one aspect, the invention is directed to novel compounds of formula I:

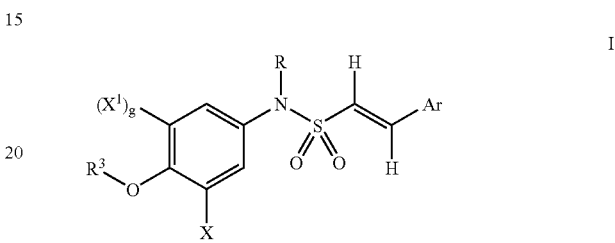

wherein:

Ar is selected from the group consisting of substituted and unsubstituted aryl, and substituted and unsubstituted heteroaryl;

X is selected from the group consisting of (i) and (ii) below:

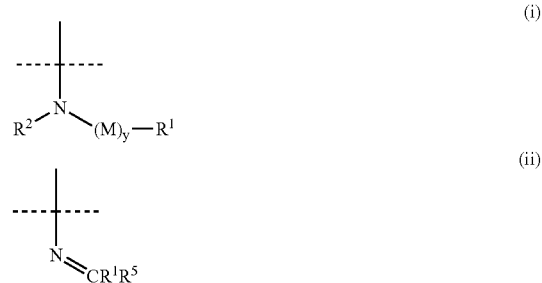

$X^1$ is selected from the group consisting of (i), (ii) and (iii) below:

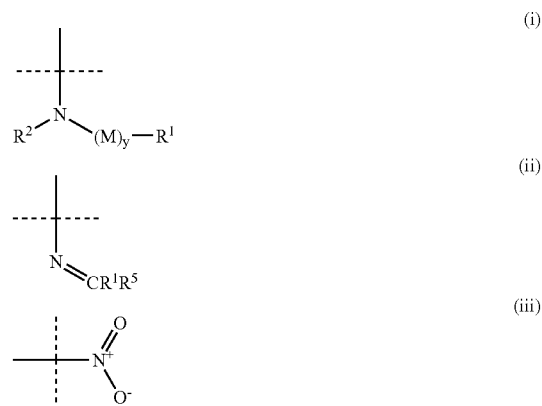

wherein $X^1$ is optionally protected with one or more chemical protecting groups;

g is 0 or 1;

each M is a bivalent connecting group independently selected from the group consisting of —($C_1$–$C_6$)alkylene-, —$(CH_2)_a$—V—$(CH_2)_b$—, —$(CH_2)_d$—W—$(CH_2)_e$— and —Z—;

each y is independently selected from the group consisting of 0 and 1;

each V is independently selected from the group consisting of —C(=O)—, —C(=O)—O—, —C(=O)—($C_1$–$C_6$)perfluoroalkylene-, —C(=S)—, —S(=O)—, —$SO_2$—, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

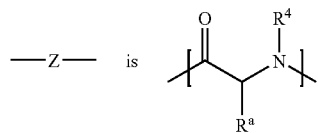

wherein the absolute stereochemistry of —Z— is D or L or a mixture of D and L;

R is selected from the group consisting of —H, ($C_1$–$C_6$)alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;

each $R^a$ is independently selected from the group consisting of —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl, —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, —($C_1$–$C_6$)perfluoroalkyl, unsubstituted aryl, substituted aryl, substituted heterocyclic, unsubstituted heterocyclic, —$CO_2R^5$, —C(=O)$NR^4_2$, —$CR^4R^6R^7$, —C(=NH)—$NR^4_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —($C_1$–$C_6$)alkyl, and aryl($C_1$–$C_3$)alkyl, wherein —$R^2$ and —$(M)_y$—$R^1$ may optionally be linked covalently to form a 5-, 6- or 7-membered substituted or unsubstituted heterocycle;

$R^3$ is independently selected from —($C_1$–$C_6$)alkyl;

each $R^4$ is independently selected from the group consisting of —H, and —($C_1$–$C_6$)alkyl;

wherein:

when $R^4$ and $R^1$ are bonded to the same nitrogen atom, $R^1$ and $R^4$ may combine to form a heterocycle; and when two $R^4$ groups are geminally bonded to the same nitrogen, the two $R^4$ groups may combine to form a heterocycle;

each $R^5$ is independently selected from the group consisting of —H, —($C_1$–$C_6$)alkyl and —($C_1$–$C_6$)acyl;

each $R^6$ is independently selected from the group consisting of —H, —($C_1$–$C_6$)alkyl, —$CO_2R^5$, —C(=O)$R^7$, —$OR^5$, —$SR^4$, —($C_1$–$C_3$)alkoxy, —($C_1$–$C_3$)alkylthio, guanidino, —$NR^4_2$, phenyl, substituted phenyl, heterocyclic, substituted heterocyclic and halogen;

each $R^7$ is independently selected from the group consisting of —H, halogen, —($C_1$–$C_6$)alkyl, —$NR^4_2$ and heterocycles containing two nitrogen atoms; and wherein the substituents for the substituted aryl and substituted heterocyclic groups comprising or included within Ar, R, $R^1$, $R^a$, $R^6$ and $R^7$, are independently selected from the group consisting of halogen, ($C_1$–$C_6$)alkyl, ($C_1$–$C_6$)alkoxy, —$NO_2$, —C≡N, —$CO_2R^5$, —C(=O)O($C_1$–$C_3$)alkyl, —OH, —($C_2$–$C_6$)—OH, phosphonato, —$NR^4_2$, —NHC(=O)($C_1$–$C_6$)alkyl, sulfamyl, carbamyl, —OC(=O)($C_1$–$C_3$)alkyl, —O($C_2$–$C_6$)—N(($C_1$–$C_6$)alkyl)$_2$ and —$CF_3$;

provided (1) when $R^1$ is a monovalent peptidyl moiety of molecular weight less than 1000 and V is —C(=O)—, —C(=S)—, —S(=O)— or —$SO_2$—, and b is 0;

then said peptidyl moiety is coupled to M through the peptide's amino terminus or through a sidechain amino group to form an amide, thioamide, sulfinamide or sulfonamide respectively;

(2) when $R^1$ is a monovalent peptidyl moiety of molecular weight less than 1000 and V is —C(=O)$NR^3$—, —$SO_2NR^3$—, or —$NR^4$—, and b is 0, then said peptidyl moiety is coupled to M through the peptide's carboxy terminus or through a sidechain carboxyl group to form an imide, sulfonimide, or carboxamide respectively; and (3) when $R^1$ is a monovalent peptidyl moiety of molecular weight less than 1000 and W is —S— or —O—, and d is 0, then said peptidyl moiety is coupled to M through the peptide's carboxy terminus or through a sidechain carboxyl group to form a carbothioic acid ester or the carboxylic ester respectively;

or a salt of such a compound.

Preferred compounds of formula I include, for example, the following compounds and salts of such compounds:

(E)-2,4,6-trimethoxystyryl-N-[(3-trifluoroacetamido)-4-methoxy-phenyl]-sulfonamide; and (E)-2,4,6-trimethoxystyryl-N-[(3-acetoxyacetamido)-4-methoxyphenyl]-sulfonamide.

According to one embodiment of the invention;

each V is independently selected from the group consisting of —C(=O)—, —C(=S)—, —S(=O)—, —$SO_2$—, —C(=O)$NR^4$—, —C(=S)$NR^4$— and —$SO_2NR^4$—;

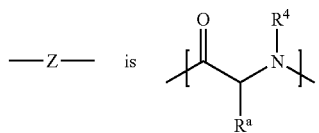

wherein the absolute stereochemistry of —Z— is either D or L;

each $R^1$ is independently selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000; provided that when y is 0 and $R^1$ is —$CO_2R^5$, $R^5$ is not —H; and each $R^6$ is independently selected from the group consisting of —H, —($C_1$–$C_6$)alkyl, —$CO_2R^5$, —C(=O)$R^7$, —OH, —$SR^4$, —($C_1$–$C_3$)alkoxy, —($C_1$–$C_3$)alkylthio, guanidino, —$NR^4_2$, phenyl, substituted phenyl, heterocyclic, substituted heterocyclic and halogen.

According to a preferred sub-embodiment thereof, there are provided compounds of formula I, wherein Z has an L absolute configuration.

According to a sub-embodiment thereof, there are provided compounds of formula I, wherein R is —H or ($C_1$–$C_6$) alkyl.

In a further sub-embodiment, novel compounds of formula I are provided wherein Ar is optionally substituted phenyl.

According to first embodiment of compounds of formula I, there are provided compounds of the formula III, below:

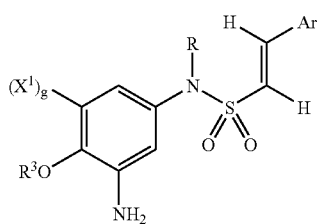

III

Ar is selected from the group consisting of substituted and unsubstituted aryl, and substituted and unsubstituted heteroaryl;

$X^1$ is selected from the group consisting of (i), (ii) and (iii) below:

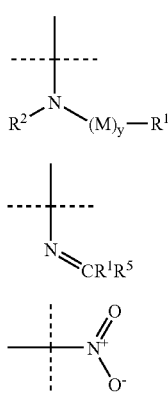

wherein $X^1$ is optionally protected with one or more chemical protecting groups;

g is 0 or 1;

M is a bivalent connecting group selected from the group consisting of —($C_1$–$C_6$)alkylene-, —$(CH_2)_a$—V—$(CH_2)_b$—, —$(CH_2)_d$—W—$(CH_2)_e$— and —Z—;

y is selected from the group consisting of 0 and 1;

V is selected from the group consisting of —C(=O)—, —C(=S)—, —S(=O)—, —$SO_2$—, —C(=O)$NR^4$—, —C(=S)$NR^4$— and —$SO_2NR^4$—

W is selected from the group consisting of —$NR^4$—, —O— and —S—;

a is selected from the group consisting of 0, 1, 2 and 3;
b is selected from the group consisting of 0, 1, 2 and 3;
d is selected from the group consisting of 1, 2 and 3;
e is selected from the group consisting of 0, 1, 2 and 3;

—Z— is 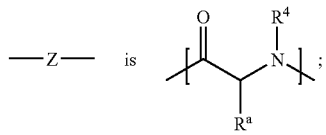;

wherein the absolute stereochemistry of —Z— is either D or L;

R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl($C_1$–$C_3$)alkyl, unsubstituted aryl($C_1$–$C_3$)alkyl, substituted heterocyclic($C_1$–$C_3$) alkyl and unsubstituted heterocyclic($C_1$–$C_3$)alkyl;

$R^a$ is selected from the group consisting of —H, —$CH_3$, —$(CH_2)_3$—NH—C($NH_2$)(=NH), —$CH_2$C(=O)$NH_2$, —$CH_2COOH$, —$CH_2SH$, —$(CH_2)_2$C(=O)—$NH_2$, —$(CH_2)_2COOH$, —$CH_2$-(2-imidazolyl), —CH($CH_3$)—$CH_2$—$CH_3$, —$CH_2CH(CH_3)_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;

$R^1$ is selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —($C_1$–$C_6$)alkyl, and aryl($C_1$–$C_3$)alkyl, wherein —$R^2$ and —$(M)_y$—$R^1$ may optionally be linked covalently to form a 5-, 6- or 7-membered substituted or unsubstituted heterocycle;

$R^3$ is independently selected from —($C_1$–$C_6$)alkyl;

each $R^4$ is independently selected from the group consisting of —H, and —($C_1$–$C_6$)alkyl;

wherein:
when $R^4$ and $R^1$ are bonded to the same nitrogen atom, $R^1$ and $R^4$ may combine to form a heterocycle; and when two $R^4$ groups are geminally bonded to the same nitrogen, the two $R^4$ groups may combine to form a heterocycle;

each $R^5$ is independently selected from the group consisting of —H, —($C_1$–$C_6$)alkyl and —($C_1$–$C_6$)acyl;

$R^6$ is selected from the group consisting of —H, —($C_1$–$C_6$)alkyl, —$CO_2R^5$, —C(=O)$R^7$, —OH, —$SR^4$, —($C_1$–$C_3$)alkoxy, —($C_1$–$C_3$)alkylthio, guanidino, —$NR^4_2$, phenyl, substituted phenyl, heterocyclic, substituted heterocyclic and halogen;

$R^7$ is selected from the group consisting of —H, halogen, —($C_1$–$C_6$)alkyl, —$NR^4_2$ and heterocycles containing two nitrogen atoms; and wherein the substituents for the substituted aryl and substituted heterocyclic groups comprising or included within Ar, R, $R^1$, $R^2$, $R^a$, $R^6$ and $R^7$, are independently selected from the group consisting of halogen, $(C_1-C_6)$alkyl, $(C_1-C_6)$alkoxy, $-NO_2$, $-C\equiv N$, $-CO_2R^5$, $-C(=O)O(C_1-C_3)$alkyl, $-OH$, $-(C_2-C_6)-OH$, phosphonato, $-NR^4{}_2$, $-NHC(=O)(C_1-C_6)$alkyl, sulfamyl, carbamyl, $-OC(=O)(C_1-C_3)$alkyl, $-O(C_2-C_6)-N((C_1-C_6)alkyl)_2$ and $-CF_3$;

provided (1) when $R^1$ is a monovalent peptidyl moiety of molecular weight less than 1000 and V is $-C(=O)-$, $-C(=S)-$, $-S(=O)-$ or $-SO_2-$, and b is 0;

then said peptidyl moiety is coupled to M through the peptide's amino terminus or through a sidechain amino group to form an amide, thioamide, sulfinamide or sulfonamide respectively;

(2) when $R^1$ is a monovalent peptidyl moiety of molecular weight less than 1000 and V is $-C(=O)NR^3-$, $-SO_2NR^3-$, or $-NR^4-$, and b is 0, then said peptidyl moiety is coupled to M through the peptide's carboxy terminus or through a sidechain carboxyl group to form an imide, sulfonimide, or carboxamide respectively; and (3) when $R^1$ is a monovalent peptidyl moiety of molecular weight less than 1000 and W is $-S-$ or $-O-$, and d is 0, then said peptidyl moiety is coupled to M through the peptide's carboxy terminus or through a sidechain carboxyl group to form a carbothioic acid ester or the carboxylic ester respectively;

or a salt of such a compound.

Suitable protecting groups are those groups which are stable to reactions designed to derivatize the 3-amino group of formula III. Subsequently said protecting groups are optionally removed to regenerate the group $X^1$.

In another sub-embodiment, thereof, there are provided compounds of the formula IIIa, below:

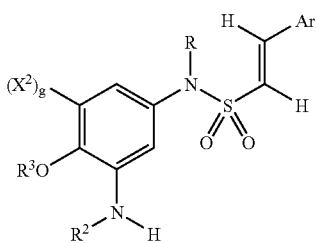

IIIa wherein:

Ar is selected from the group consisting of substituted and unsubstituted aryl, and substituted and unsubstituted heteroaryl;

$X^2$ is selected from the group consisting of $NO_2$ and $-NH_2$, optionally protected with a chemical protecting group;

g is 0 or 1;

R is selected from the group consisting of $-H$, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heterocyclic, unsubstituted heterocyclic, substituted aryl$(C_1-C_3)$alkyl, unsubstituted aryl$(C_1-C_3)$alkyl, substituted heterocyclic$(C_1-C_3)$alkyl and unsubstituted heterocyclic$(C_1-C_3)$alkyl;

$R^2$ is independently selected from the group consisting of $-H$, $-(C_1-C_6)$alkyl, and aryl$(C_1-C_3)$alkyl, wherein $-R^2$ and $-(M)_y-R^1$ may optionally be linked covalently to form a 5-, 6- or 7-membered substituted or unsubstituted heterocycle;

each $R^3$ is independently selected from $-(C_1-C_6)$alkyl;

or a salt of such a compound.

In a sub-embodiment thereof, there is provided a compound wherein Ar is optionally substituted phenyl; or a salt of such a compound.

According to another sub-embodiment of compounds of formula I, there is provided compounds of formula I':

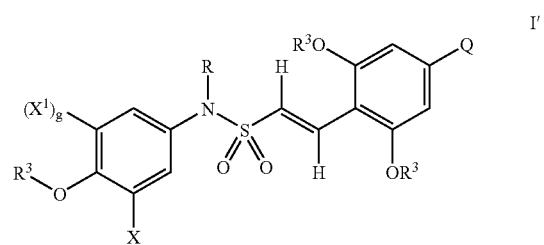

I' wherein:

X is selected from the group consisting of (i) and (ii) below:

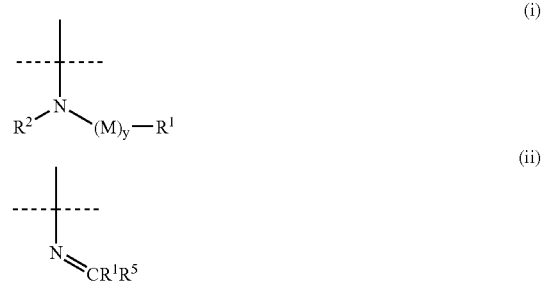

(i)

(ii)

$X^1$ is selected from the group consisting of (i), (ii) and (iii) below:

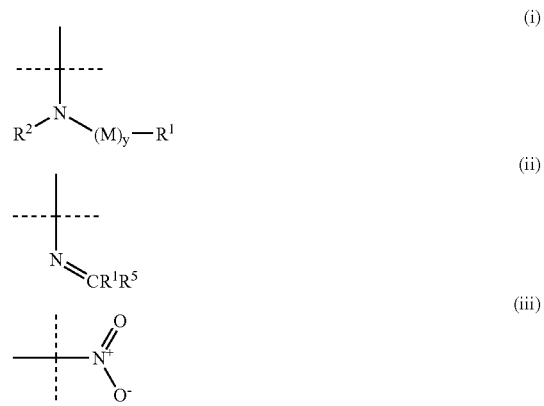

(i)

(ii)

(iii)

wherein $X^1$ is optionally protected with one or more chemical protecting groups;

g is 0 or 1;

each M is a bivalent connecting group independently selected from the group consisting of $-C_1-C_6$alkylene-, $-(CH_2)_a-V-(CH_2)_b-$, $-(CH_2)_d-W-(CH_2)_e-$ and $-Z-$;

each y is independently selected from the group consisting of 0 and 1;

each V is independently selected from the group consisting of —C(=O)—, —C(=S)—, —S(=O)—, —$SO_2$—, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

—Z— is wherein the absolute stereochemistry of —Z— is either D or L;

R is selected from the group consisting of —H, ($C_1$–$C_6$)alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;

each $R^a$ is independently selected from the group consisting of —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —($C_1$–$C_6$)alkyl, and aryl($C_1$–$C_3$)alkyl, wherein —$R^2$ and —$(M)_y$—$R^1$ may optionally be linked covalently to form a 5-, 6- or 7-membered substituted or unsubstituted heterocycle;

each $R^3$ is independently selected from —($C_1$–$C_6$)alkyl;

each $R^4$ is independently selected from the group consisting of —H, and —($C_1$–$C_6$)alkyl;

wherein:

when $R^4$ and $R^1$ are bonded to the same nitrogen atom, $R^1$ and $R^4$ may combine to form a heterocycle; and when two $R^4$ groups are geminally bonded to the same nitrogen, the two $R^4$ groups may combine to form a heterocycle;

each $R^5$ is independently selected from the group consisting of —H, —($C_1$–$C_6$)alkyl and —($C_1$–$C_6$)acyl;

each $R^6$ is independently selected from the group consisting of —H, —($C_1$–$C_6$)alkyl, —$CO_2R^5$, —C(=O)$R^7$, —OH, —$SR^4$, —($C_1$–$C_3$)alkoxy, —($C_1$–$C_3$)alkylthio, guanidino, —$NR^4_2$, phenyl, substituted phenyl, heterocyclic, substituted heterocyclic and halogen;

each $R^7$ is independently selected from the group consisting of —H, halogen, —($C_1$–$C_6$)alkyl, —$NR^4_2$ and heterocycles containing two nitrogen atoms; and Q is selected from the group consisting of —H, —($C_1$–$C_6$)alkoxy, halogen, —($C_1$–$C_6$)alkyl and —$NR^4_2$;

wherein the substituents for the substituted aryl and substituted heterocyclic groups comprising or included within R, $R^1$, $R^a$, $R^6$ and $R^7$, are independently selected from the group consisting of halogen, ($C_1$–$C_6$)alkyl, ($C_1$–$C_6$)alkoxy, —$NO_2$, —C≡N, —$CO_2R^5$, —C(=O)O($C_1$–$C_3$)alkyl, —OH, —($C_2$–$C_6$)—OH, phosphonato, —$NR^4_2$, —NHC(=O)($C_1$–$C_6$)alkyl, sulfamyl, carbamyl, —OC(=O)($C_1$–$C_3$)alkyl, —O($C_2$–$C_6$)—N(($C_1$–$C_6$)alkyl)$_2$ and —$CF_3$;

provided (1) when $R^1$ is a monovalent peptidyl moiety of molecular weight less than 1000 and V is —C(=O)—, —C(=S)—, —S(=O)— or —$SO_2$—, and b is 0;

then said peptidyl moiety is coupled to M through the peptide's amino terminus or through a sidechain amino group to form an amide, thioamide, sulfinamide or sulfonamide respectively;

(2) when $R^1$ is a monovalent peptidyl moiety of molecular weight less than 1000 and V is —C(=O)$NR^3$—, —$SO_2NR^3$—, or —$NR^4$—, and b is 0, then said peptidyl moiety is coupled to M through the peptide's carboxy terminus or through a sidechain carboxyl group to form an imide, sulfonimide, or carboxamide respectively; and (3) when $R^1$ is a monovalent peptidyl moiety of molecular weight less than 1000 and W is —S— or —O—, and d is 0, then said peptidyl moiety is coupled to M through the peptide's carboxy terminus or through a sidechain carboxyl group to form a carbothioic acid ester or the carboxylic ester respectively;

or a salt of such a compound.

In a further sub-embodiment there are provided compounds of formula IIIa':

IIIa' wherein:

$X^2$ is selected from the group consisting of $NO_2$ and —$NH_2$, optionally protected with a chemical protecting group;

g is 0 or 1;

R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl($C_1$–$C_3$)alkyl, unsubstituted aryl($C_1$–$C_3$)alkyl, substituted heterocyclic($C_1$–$C_3$) alkyl and unsubstituted heterocyclic($C_1$–$C_3$)alkyl;

$R^2$ is independently selected from the group consisting of —H, —($C_1$–$C_6$)alkyl, and aryl($C_1$–$C_3$)alkyl, wherein —$R^2$ and —$(M)_y$—$R^1$ may optionally be linked covalently to form a 5-, 6- or 7-membered substituted or unsubstituted heterocycle;

each $R^3$ is independently selected from —($C_1$–$C_6$)alkyl;

each $R^4$ is independently selected from the group consisting of —H, and —($C_1$–$C_6$)alkyl;

Q is selected from the group consisting of —H, —($C_1$–$C_6$)alkoxy, halogen, —($C_1$–$C_6$)alkyl and —$NR^4{}_2$;

or a salt of such a compound.

The strategy for synthesizing compounds of formula I involves derivatization of primary or secondary amino group at the 3-position of an intermediate of formula IIIa'. Such derivatizations of the 3-amino group include for example reactions to form carboxamides, sulfonamides alkyl amines, nitrogen-containing heterocycles, imines, guanidines, ureas, amidines, and amino ketones.

The intermediate of formula IIIa' also incorporates an optional group at the 5-position, which can be a nitro group or a protected amino group. In the synthetic strategy, this 5-substituent serves as a second, latent amino group. The use of this protecting group strategy allows for differential derivatization of these two amino groups, i.e., the 3-amino group of formula IIIa' and the moiety at the 5-position which is inert to the conditions of the derivatization of the 3-amino group. Hence, the synthetic route involves first derivatizing the 3-amino group, followed by conversion of the 5-substituent to an amino group via either (a) deprotection, if $X^2$ is a protected amine, or (b) chemical reduction if $X^2$ is a nitro group. From a retrosynthetic viewpoint, this synthetic route allows for differential derivatization of two amino groups, one at the 5-position which is protected (either with a chemical protecting group, or by being in a nitro oxidation state) and thereby inert to the conditions of the derivatization of the 3-amino group. Suitable chemical protecting groups for the 5-position protected amine, include for example, benzyl, 2,4-dimethoxy-benzyl and benzyloxycarbonyl (CBZ). In a similar manner, when $X^2$ is —$NO_2$, the 3-amino group may be derivatized in the aforesaid manner. Subsequently the —$NO_2$ group may optionally be chemically reduced to the corresponding 5-amino group via a variety of procedures known to those skilled in the art.

Subsequently, the 5-amino group, generated by either reduction of a 5-nitro group or by removing a protecting group from a protected 5-amino compound, is optionally derivatized. Derivatization of the 5-amino group may be the same or different from the derivatization of the 3-amino group.

According to a sub-embodiment of said compounds of formula IIIa', compounds are provided wherein Q is ($C_1$–$C_6$) alkoxy; or salts thereof.

According to another sub-embodiment compounds of formula IIIa' are provided wherein Q is —$OCH_3$; or salts thereof.

According to a further sub-embodiment, compounds of formula IIIa' are provided wherein $R^3$ is —$CH_3$; or salts thereof.

One such compound is (E)-2,4,6-trimethoxystyryl-4-methoxy-3-aminophenylsulfonamide, or a salt of such a compound.

According to a second embodiment of the invention of formula I,

X is

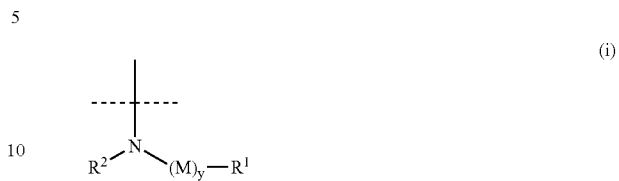

and y is 1; M is —$(CH_2)_a$—V—$(CH_2)_b$—; and V is —C(=O)—.

According to a sub-embodiment thereof are provided compounds wherein Ar is optionally substituted phenyl; and salts thereof.

According to a sub-embodiment thereof, compounds of the formula IV, below, and salts thereof are provided:

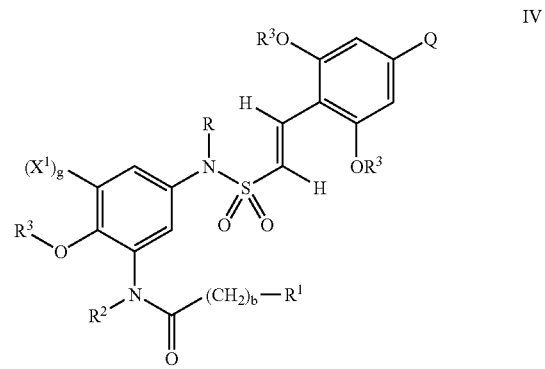

In a sub-embodiment thereof, compounds of formula IV are provided wherein g is 0; and salts thereof.

Preferred compounds of formula IV, include, for example, the following compounds and salts thereof:

(E)-2,4,6-trimethoxystyryl-N-(3-carboxyacetamido-4-methoxyphenyl)-sulfonamide;

(E)-2,4,6-trimethoxystyryl-N-[3-(3,5-dinitrobenzamido)-4-methoxy-phenyl]-sulfonamide;

(E)-2,4,6-trimethoxystyryl-N-[3-(3,5-diaminobenzamido)-4-methoxy-phenyl]-sulfonamide;

(E)-2,4,6-trimethoxystyryl-N-(3-chloroacetamido-4-methoxyphenyl)-sulfonamide;

(E)-2,4,6-trimethoxystyryl-N-[3-(4-methylpiperazinyl) acetamido-4-methoxyphenyl]sulfonamide;

(E)-2,4,6-trimethoxystyryl-N-[(3-benzamido)-4-methoxyphenyl]-sulfonamide;

(E)-2,4,6-trimethoxystyryl-N-3[(4-nitrobenzamido)-4-methoxyphenyl]-sulfonamide;

(E)-2,4,6-trimethoxystyryl-N-3[(4-aminobenzamido)-4-methoxyphenyl]-sulfonamide;

(E)-2,4,6-trimethoxystyryl-N-[(3-acetamido)-4-methoxyphenyl]-sulfonamide;

(E)-2,4,6-trimethoxystyryl-N-[(3-hydroxyacetamido)-4-methoxyphenyl)]-sulfonamide; and (E)-2,4,6-trimethoxystyryl-N-[(3-N,N-dimethylacetamido)-4-methoxyphenyl]-sulfonamide.

According to a third embodiment of the invention of formula I, X is

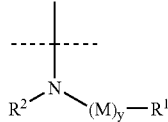

(i)

and y is 1; and M is —Z—.

According to a sub-embodiment thereof, compounds are provided wherein Ar is optionally substituted phenyl, and salts thereof.

According to another sub-embodiment thereof, compounds of formula V and salts thereof, are provided:

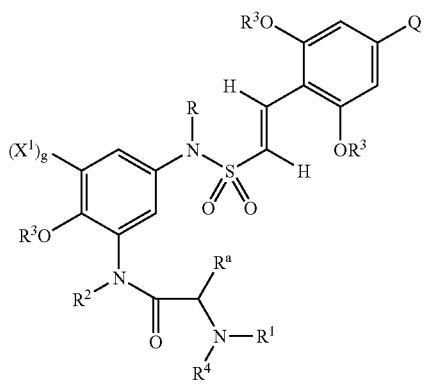

V wherein:

each $R^a$ is independently selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein $R^a$ and $R^1$ combine to form a 5-, 6- or 7-membered heterocyclic ring.

Heterocyclic rings formed by the combination of $R^a$ and $R^1$ include for example: pyrrolidine, hydroxy pyrrolidine, piperidine, homopiperidine and thiazolidine.

In a sub-embodiment thereof, compounds of formula V are provided wherein g is 0; and salts thereof.

Preferred compounds of formula V include, for example, the following compounds and salts thereof:

(E)-2,4,6-trimethoxystyryl-N-(3-amino-4-methoxyphenyl)sulfonamide-L-lysineamide;

(E)-2,4,6-trimethoxystyryl-N-(3-amino-4-methoxyphenyl)sulfonamide-L-serineamide; and (E)-2,4,6-trimethoxystyryl-N-(3-amino-4-methoxyphenyl)sulfonamide-D-serineamide;

According to a fourth embodiment of the invention of formula I,

X is

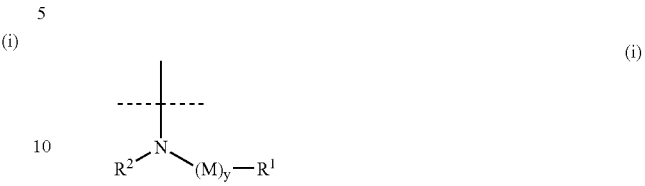

(i)

and y is 1; M is —(CH$_2$)$_a$—V—(CH$_2$)$_b$—; and V is —SO$_2$—.

According to a further sub-embodiment thereof compounds are provided wherein Ar is optionally substituted phenyl; and salts thereof. According to a sub-embodiment thereof compounds of formula VI and salts thereof are provided:

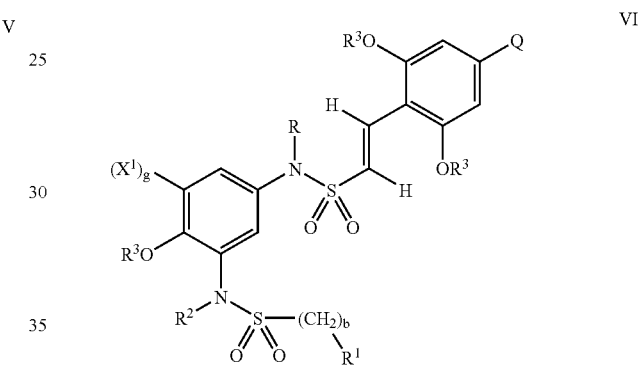

VI

In one such embodiment, compounds of formula VI are provided wherein g is 0; and salts thereof.

Compounds of formula VI, include for example the following compounds and salts thereof:

(E)-2,4,6-trimethoxystyryl-N-(3-carboxymethylsulfamyl-4-methoxyphenyl)-sulfonamide;

(E)-2,4,6-trimethoxystyryl-N-[3-(3,5-dinitrobenzenesulfamyl)-4-methoxy-phenyl]sulfonamide; and (E)-2,4,6-trimethoxystyryl-N-[3-(3,5-diaminobenzenesulfamyl)-4-methoxy-phenyl]sulfonamide.

According to a fifth embodiment of the invention of formula I, X is

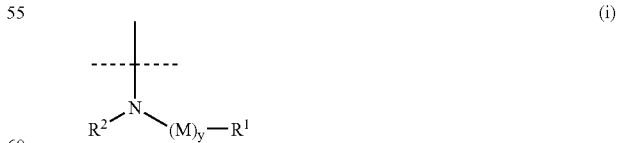

(i)

and y is 0 and $R^1$ is —C(=NH)—NR$^4$$_2$.

According to a sub-embodiment thereof compounds are provided wherein Ar is optionally substituted phenyl; and salts thereof. According to another sub-embodiment thereof, compounds of formula VII, and salts thereof, are provided:

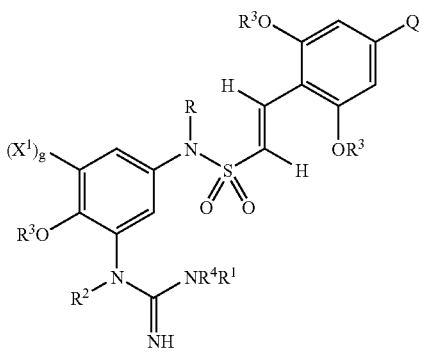

VII

In a sub-embodiment thereof, compounds of formula VII are provided wherein g is 0; and salts thereof.

One such compound is (E)-2,4,6-trimethoxystyryl-N-(3-guanidino-4-methoxy-phenyl)sulfonamide, or a salt of such a compound.

According to a sixth embodiment of the invention of formula I, X is

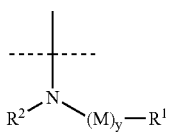

(i)

and y is 1; and M is —(C$_1$–C$_6$)alkylene-.

According to one sub-embodiment thereof, compounds are provided wherein Ar is optionally substituted phenyl; and salts thereof.

According to another sub-embodiment thereof, compounds of the formula VIII, and salts thereof, are provided:

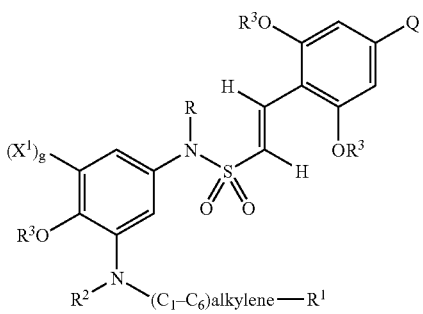

VIII

In a sub-embodiment thereof, compounds of formula VIII are provided wherein g is 0; and salts thereof.

Exemplary compounds of formula VIII include for example, the following compounds and salts thereof:

(E)-2,4,6-trimethoxystyryl-N-(3-carboxymethylamino-4-methoxy-phenyl)sulfonamide; and (E)-2,4,6-trimethoxystyryl-N-(3-N-methylamino-4-methoxyphenyl)-sulfonamide.

According to a seventh embodiment of the invention, compounds of the formula IX and salts thereof are provided:

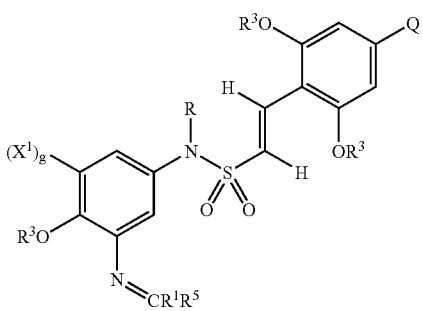

IX

In a sub-embodiment thereof, compounds of formula IX are provided wherein g is 0; and salts thereof.

One such compound is (E)-2,4,6-trimethoxystyryl-N-3 [(4-nitrophenylimino)-4-methoxyphenyl]sulfonamide, or a salt of such a compound.

According to an eighth embodiment of the invention of formula I,

X is

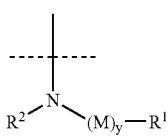

(i)

and y is 1; M is —(CH$_2$)$_a$—V—(CH$_2$)$_b$—; and V is —C(=O)NR$^4$—.

According to one sub-embodiment thereof compounds are provided wherein Ar is optionally substituted phenyl; and salts thereof.

According to another sub-embodiment thereof, compounds of formula X and salts thereof are provided:

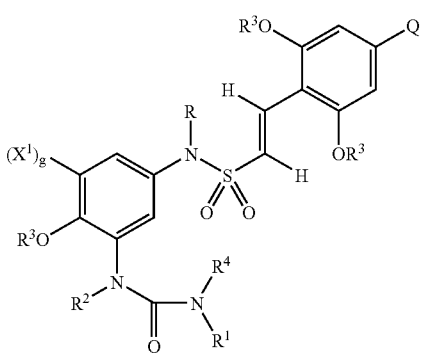

X

In a sub-embodiment thereof, compounds of formula X are provided wherein g is 0; and salts thereof.

An exemplary compound of formula X is (E)-2,4,6-trimethoxystyryl-N-(3-ureido-4-methoxyphenyl)sulfonamide, or a salt of such a compound.

According to a ninth embodiment of the invention, compounds of the formula II and salts thereof are provided:

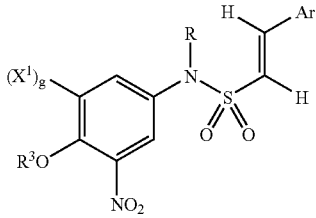

wherein:

Ar is selected from the group consisting of substituted and unsubstituted aryl, and substituted and unsubstituted heteroaryl;

$X^1$ is selected from the group consisting of (i), (ii) and (iii) below:

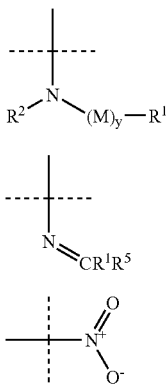

wherein $X^1$ is optionally protected with one or more chemical protecting groups;

g is 0 or 1;

M is a bivalent connecting group selected from the group consisting of —$(C_1–C_6)$alkylene-, —$(CH_2)_a$—V—$(CH_2)_b$—, —$(CH_2)_d$—W—$(CH_2)_e$— and —Z—;

y is selected from the group consisting of 0 and 1;

V is selected from the group consisting of —C(=O)—, —C(=S)—, —S(=O)—, —$SO_2$—, —C(=O)$NR^4$—, —C(=S)$NR^4$— and —$SO_2NR^4$—

W is selected from the group consisting of —$NR^4$—, —O— and —S—;

a is selected from the group consisting of 0, 1, 2 and 3;

b is selected from the group consisting of 0, 1, 2 and 3;

d is selected from the group consisting of 1, 2 and 3;

e is selected from the group consisting of 0, 1, 2 and 3;

—Z— is

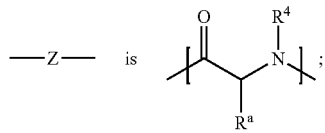

wherein the absolute stereochemistry of —Z— is either D or L;

R is selected from the group consisting of —H, $(C_1–C_6)$alkyl, $(C_1–C_6)$alkoxy, $(C_3–C_6)$alkenyl, $(C_2–C_6)$heteroalkyl, $(C_3–C_6)$heteroalkenyl, $(C_2–C_6)$hydroxyalkyl, substituted aryl, unsubstituted aryl, substituted heterocyclic, unsubstituted heterocyclic, substituted aryl$(C_1–C_3)$alkyl, unsubstituted aryl$(C_1–C_3)$alkyl, substituted heterocyclic$(C_1–C_3)$alkyl and unsubstituted heterocyclic$(C_1–C_3)$alkyl;

$R^a$ is selected from the group consisting of —H, —$CH_3$, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2$ COOH, —$CH_2$-(2-imidazolyl), —$CH(CH_3)$—$CH_2$—$CH_3$, —$CH_2CH(CH_3)_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —$CH(CH_3)_2$ and —$CH_2$—$CH_3$; and includes compounds wherein $R^a$ and $R^1$ combine to form a 5-, 6- or 7-membered heterocyclic ring;

$R^1$ is selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —$(C_1–C_6)$alkyl, and aryl$(C_1–C_3)$alkyl, wherein —$R^2$ and —$(M)_y$—$R^1$ may optionally be linked covalently to form a 5-, 6- or 7-membered substituted or unsubstituted heterocycle;

$R^3$ is independently selected from —$(C_1–C_6)$alkyl;

each $R^4$ is independently selected from the group consisting of —H, and —$(C_1–C_6)$alkyl;

wherein:

when $R^4$ and $R^1$ are bonded to the same nitrogen atom, $R^1$ and $R^4$ may combine to form a heterocycle; and when two $R^4$ groups are geminally bonded to the same nitrogen, the two $R^4$ groups may combine to form a heterocycle;

each $R^5$ is independently selected from the group consisting of —H, —$(C_1–C_6)$alkyl and —$(C_1–C_6)$acyl;

$R^6$ is selected from the group consisting of —H, —$(C_1–C_6)$alkyl, —$CO_2R^5$, —C(=O)$R^7$, —OH, —$SR^4$, —$(C_1–C_3)$alkoxy, —$(C_1–C_3)$alkylthio, guanidino, —$NR^4_2$, phenyl, substituted phenyl, heterocyclic, substituted heterocyclic and halogen;

$R^7$ is selected from the group consisting of —H, halogen, —$(C_1–C_6)$alkyl, —$NR^4_2$ and heterocycles containing two nitrogen atoms; and wherein the substituents for the substituted aryl and substituted heterocyclic groups comprising or included within Ar, R, $R^1$, $R^2$, $R^a$, $R^6$ and $R^7$, are independently selected from the group consisting of halogen, $(C_1–C_6)$alkyl, $(C_1–C_6)$alkoxy, —$NO_2$, —C≡N, —$CO_2R^5$, —C(=O)O $(C_1–C_3)$alkyl, —OH, —$(C_2–C_6)$—OH, phosphonato, —$NR^4_2$, —NHC((=O)$(C_1–C_6)$alkyl, sulfamyl, carbamyl, —OC(=O)$(C_1–C_3)$alkyl, —O$(C_2–C_6)$—N$((C_1–C_6)$alkyl$)_2$ and —$CF_3$;

provided (1) when $R^1$ is a monovalent peptidyl moiety of molecular weight less than 1000 and V is —C(=O)—, —C(=S)—, —S(=O)— or —$SO_2$—, and b is 0;

then said peptidyl moiety is coupled to M through the peptide's amino terminus or through a sidechain amino group to form an amide, thioamide, sulfinamide or sulfonamide respectively;

(2) when $R^1$ is a monovalent peptidyl moiety of molecular weight less than 1000 and V is —C(=O)$NR^3$—, —$SO_2NR^3$—, or —$NR^4$—, and b is 0, then said peptidyl moiety is coupled to M through the peptide's carboxy terminus or through a sidechain carboxyl group to form an imide, sulfonimide, or carboxamide respectively; and (3) when $R^1$ is a monovalent peptidyl moiety of molecular weight less than 1000 and W is —S— or —O—, and d is 0, then said peptidyl moiety is coupled to M through the peptide's carboxy terminus or through a sidechain carboxyl group to form a carbothioic acid ester or the carboxylic ester respectively;

or a salt of such a compound.

According to a sub-embodiment thereof, compounds of formula IIa are provided:

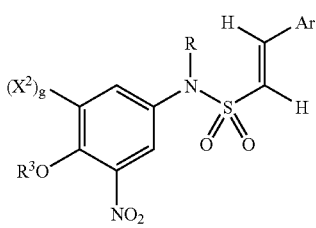

IIa wherein:

g is 0 or 1;

R is selected from the group consisting of —H, $(C_1-C_6)$ alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heterocyclic, unsubstituted heterocyclic, substituted aryl$(C_1-C_3)$alkyl, unsubstituted aryl$(C_1-C_3)$alkyl, substituted heterocyclic$(C_1-C_3)$ alkyl and unsubstituted heterocyclic$(C_1-C_3)$alkyl;

$R^3$ is independently selected from —$(C_1-C_6)$alkyl;

$X^2$ is selected from the group consisting of $NO_2$ and —$NH_2$, optionally protected with a chemical protecting group;

or a salt of such a compound.

Compounds of formula IIa are intermediates in the synthesis of compounds of formula I wherein the 3-nitro group may be chemically reduced with for example, hydrazine and a palladium catalyst to form a compound of formula IIIa as described above.

One such compound of formula IIa is (E)-2,4,6-trimethoxystyryl-4-methoxy-3-nitrophenylsulfonamide.

In another embodiment, an intermediate in the preparation of compounds of the present invention is a compound of the formula C or a salt of such a compound:

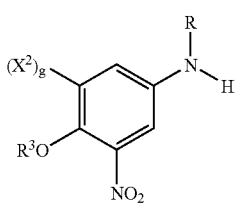

C

In a further embodiment, an intermediate in the preparation of compounds of the present invention is a compound of the formula C'; or a salt of such a compound.

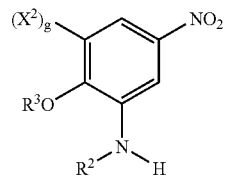

C'

In each of the formulas C and C':

$R^3$ is independently selected from —$(C_1-C_6)$alkyl;

$X^2$ is selected from the group consisting of $NO_2$ and —$NH_2$, optionally protected with a chemical protecting group; and g is 0 or 1.

According to other embodiments of the invention, processes for preparing compounds according to formula I are provided.

In one such embodiment, a process for preparing a compound of formula I is provided comprising:

(1) coupling a compound of formula IIIa or a salt of such a compound:

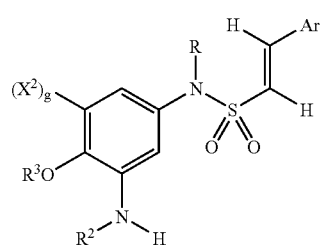

IIIa wherein:

Ar is selected from the group consisting of substituted and unsubstituted aryl, and substituted and unsubstituted heteroaryl;

$X^2$ is selected from the group consisting of $NO_2$ and —$NH_2$, optionally protected with a chemical protecting group;

g is 0 or 1;

R is selected from the group consisting of —H, $(C_1-C_6)$ alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heterocyclic, unsubstituted heterocyclic, substituted aryl$(C_1-C_3)$alkyl, unsubstituted aryl$(C_1-C_3)$alkyl, substituted heterocyclic$(C_1-C_3)$ alkyl and unsubstituted heterocyclic$(C_1-C_3)$alkyl;

each $R^3$ is independently selected from —$(C_1-C_6)$alkyl;

or a salt of such a compound.

with a compound of formula XI:

$$R^1—A \qquad XI$$

wherein one or more functional groups comprising $R^1$ are optionally protected by chemical protecting groups; and wherein A is a moiety containing an electrophilic reactive center, and said moiety is selected from the group consisting of:
  (a) an alkyl moiety having a leaving group, e.g., a moiety such as a halide, a mesylate or a tosylate;
  (b) an aryl halide moiety or aryl pseudo halide moiety.
  (c) a carboxylic acid moiety activated with a leaving group, for example a carboxylic acid chloride moiety or a carboxylic acid anhydride moiety;
  (d) a sulfonic acid moiety activated with a leaving group, for example a sulfonyl chloride moety;
  (e) a carbamic acid moiety activated with a leaving group, for example a carbamyl chloride moiety;
  (f) a cyanate moiety, for example, potassium cyanate;
  (g) an aldehyde or ketone moiety, or a hydrate thereof, or a ketal or acetal thereof;
  (h) a carboxylic acid moiety or an amino acid moiety, wherein an amide coupling agent is employed in the reaction; and
  (i) a moiety that is the product of the reaction of a substituted thiourea moiety and a 1-methyl- or 1-phenyl-2-halopyridinium salt, preferably 2-chloro-1-methylpyridinium iodide, which iodide is also known as Mukaima's reagent;
to form a compound of formula Ia:

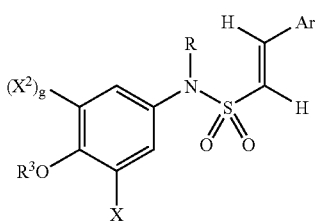

Ia (2) optionally:
  (a) when —$X^2$ is —$NH_2$ protected with a protecting group, removing said protecting group from said —$X^2$ to yield a compound of formula Ib; or
  (b) when —$X^2$ is —$NO_2$, chemically reducing said —$NO_2$; to form a compound of formula Ib:

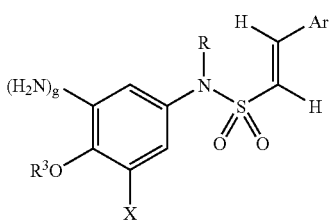

Ib (3) optionally coupling said compound of formula Ib or a salt of such a compound:
  with a compound of formula XI:

$R^1$—A        XI wherein one or more functional groups comprising $R^1$ are optionally protected by chemical protecting groups and A is defined as above; and (4) optionally removing said protecting groups protecting functionalities comprising $R^1$ to form a compound of formula I:

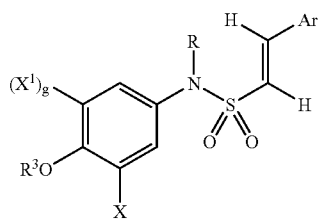

I or a salt of such a compound.

In the aforesaid process of coupling compounds of formula IIIa to compounds of formula XI, and the coupling of compounds of formula Ib to compounds compounds of formula A, the electrophile XI in the second coupling may be the same or different from that in the first coupling. Halides which may comprise a leaving group component of the electrophylic functionality A are preferably chloro, bromo or iodo. The term "pseudo halide" refers to a moiety which behaves like a halide in palladium or nickel-catalyzed amination reactions. Pseudo halide moieties include for example, triflates and mesylates.

Carboxylic acid moieties which may comprise the electrophilic functionality A include, for example, amino acid residues bearing optional protecting groups on any alpha-amino functionality, sidechain amino functionality, alpha carboxylic acid functionality, sidechain carboxylic acid functionality or other sidechain functionalities that require a protecting group. Such amino acids may be naturally occurring amino acids or synthetic amino acids including amino acids of either R— or S— absolute configuration.

Additionally, in the aforesaid process of coupling compounds of formula IIIa to compounds of formula XI, and the coupling of compounds of formula Ib to compounds of formula XI, the term "protecting group" refers to a derivative of a chemical functional group which is employed to derivatize chemical functionalities which would otherwise be incompatable with the conditions of a desired reaction. The protecting group renders this functionality stable to the desired reaction conditions and may later be removed to regenerate the de-protected functionality. One example of the use of protecting groups is in the common reaction of the amino group of a first amino acid with the carboxyl group of a second amino acid to form an amide bond. However, since each reactant contains both an amino and a carboxylate functional group, the reaction between them is (1) nonspecific as to which amino group will react with which carboxyl group, and (2) subject to polymerization since the product of the reaction still contains both reactive moieties. A protecting group on the carboxylate of the first amino acid and a protecting group acid on the amino group of the second amino acid will serve to limit the reagents to the single desired reaction of the amino group of the first amino acid with the carboxylic acid of the second amino acid and yields a product which will not react further because both of the remaining reactive moieties are blocked by protecting groups which may be subsequently be removed.

Any chemical functionality that is a structural component of $R^1$ may be optionally protected with a chemical protecting group if such a protecting group is useful in the synthesis of compounds of formula I. Appropriate protecting groups for functionalities comprising $R^1$, include for example, such moieties as tert-butoxy carbonyl (t-Boc) or 9-fluorenyl-methoxycarbonyl (Fmoc).

Additionally, in the aforesaid process of coupling compounds of formula IIIa to compounds of formula XI, and the optional coupling of compounds of formula Ib to compounds of formula XI, "amide coupling reagents" are compounds used to couple unactivated carboxylic acid moieties to amino groups, such as the aromatic amino moiety of a compound of formula I wherein —X is $NH_2$ (i.e., wherein X is formula (i), y is 0, $R^1$ is —H and $R^2$ is —H). Such amide coupling reagents include for example, reagents such as diisopropyl carbodiimide and O-(7-azabenzotriazol-1-yl)-N,N,N',N'-tetramethyluronium hexafluoro-phosphate (HATU).

Following the aforesaid process of coupling compounds of formula IIIa to compounds of formula XI, and the optional coupling of compounds of formula Ib to compounds of formula XI, any protecting groups used in the synthesis of a compound of formula I, are optionally removed.

According to a further embodiment of the invention, a process for preparing compounds according to formula IIIa is provided, comprising:

(1) chemically reducing a compound according to formula IIa:

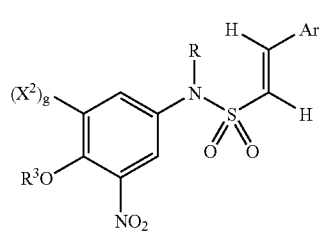

and (2) optionally alkylating the resulting aniline via any suitable amine alkylation; to form a compound of formula IIIa;

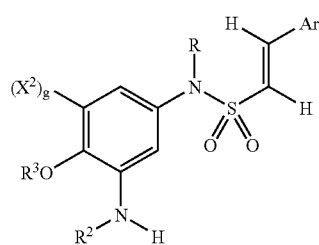

wherein:

Ar is selected from the group consisting of substituted and unsubstituted aryl, and substituted and unsubstituted heteroaryl;

$X^2$ is selected from the group consisting of $NO_2$ and —$NH_2$, optionally protected with a chemical protecting group;

g is 0 or 1;

R is selected from the group consisting of —H, $(C_1-C_6)$ alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heterocyclic, unsubstituted heterocyclic, substituted aryl$(C_1-C_3)$alkyl, unsubstituted aryl$(C_1-C_3)$alkyl, substituted heterocyclic$(C_1-C_3)$alkyl and unsubstituted heterocyclic$(C_1-C_3)$alkyl;

each $R^3$ is independently selected from —$(C_1-C_6)$alkyl; or a salt of such a compound.

The term "chemically reducing" or "chemical reduction" refers to a chemical reaction wherein the reactant which is reduced has a net gain of electrons. In the aforesaid process, the —$NO_2$ functionality is reduced to a —$NH_2$ functionality. This reduction reaction may be effected by a variety of procedures familiar to one of ordinary skill in synthetic chemistry. Such procedures include for example: catalytic hydrogenation using a catalyst such as, for example, palladium or platinum and a hydrogen source, which may be for example, introduction of $H_2$ gas, or may be via a chemical generator of hydrogen such as hydrazine. Other procedures include for example, metal and metal salt reagents such as, for example, $Sn^\circ$, $Zn^\circ$, $Fe^\circ$ and $SnCl_2$. Other reagents that accomplish this type of chemical reduction include for example, sulfite reagents such as sodium hydrosulfite.

Suitable alkylations of an aniline nitrogen include:

(a) alkylation with an alkyl moiety having a leaving group, such as, for example and alkyl halide or an alkyl mesylate; and (b) reductive amination, ie., reaction with an aldehyde or a ketone in the presence of a reducing agent such as sodium cyano borohydride or sodium triacetoxy borohydride.

Compounds of formula IIa may be prepared by a process comprising condensing a compound of formula D

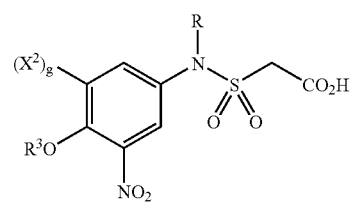

with a compound of formula E

to form a compound of formula IIa:

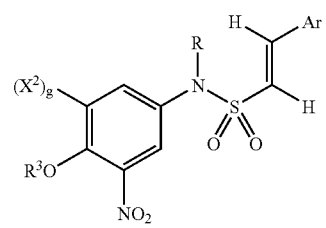

wherein:

Ar is selected from the group consisting of substituted and unsubstituted aryl, and substituted and unsubstituted heteroaryl;

g is 0 or 1;

$R^3$ is independently selected from —$(C_1-C_6)$alkyl;

$X^2$ is selected from the group consisting of —$NO_2$ and —$NH_2$, optionally protected with a chemical protecting group.

In another embodiment of the invention, a process for preparing a compound of formula I is provided comprising:

(1) coupling a compound of formula C':

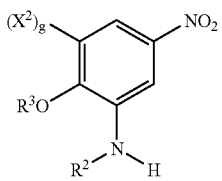

wherein:

$X^2$ is —$NH_2$, optionally protected with a chemical protecting group.

g is 0 or 1;

$R^3$ is independently selected from —$(C_1-C_6)$alkyl;

or a salt of such a compound;

with a compound of formula XI $R^1$—A    XI wherein:

$R^1$ is selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000;

each $R^4$ is independently selected from the group consisting of —H, and —$(C_1-C_6)$alkyl; wherein:

when $R^4$ and $R^1$ are bonded to the same nitrogen atom, $R^1$ and $R^4$ may combine to form a heterocycle; and when two $R^4$ groups are geminally bonded to the same nitrogen, the two $R^4$ groups may combine to form a heterocycle;

each $R^5$ is independently selected from the group consisting of —H, —$(C_1-C_6)$alkyl and —$(C_1-C_6)$acyl;

$R^6$ is selected from the group consisting of —H, —$(C_1-C_6)$alkyl, —$CO_2R^5$, —C(=O)$R^7$, —OH, —$SR^4$, —$(C_1-C_3)$alkoxy, —$(C_1-C_3)$alkylthio, guanidino, —$NR^4_2$, phenyl, substituted phenyl, heterocyclic, substituted heterocyclic and halogen;

$R^7$ is selected from the group consisting of —H, halogen, —$(C_1-C_6)$alkyl, —$NR^4_2$ and heterocycles containing two nitrogen atoms;

wherein the substituents for the substituted aryl and substituted heterocyclic groups comprising or included within $R^1$, $R^6$ and $R^7$, are independently selected from the group consisting of halogen, $(C_1-C_6)$alkyl, $(C_1-C_6)$alkoxy, —$NO_2$, —C≡N, —$CO_2R^5$, —C(=O)O$(C_1-C_3)$alkyl, —OH, —$(C_2-C_6)$—OH, phosphonato, —$NR^4_2$, —NHC(=O)$(C_1-C_6)$alkyl, sulfamyl, —OC(=O)$(C_1-C_3)$alkyl, —O$(C_2-C_6)$—N$((C_1-C_6)$alkyl$)_2$ and —$CF_3$; and wherein one or more functional groups comprising $R^1$ are optionally protected by chemical protecting groups; and wherein A is a moiety containing an electrophilic reactive center, said moiety selected from the group consisting of:

(a) an alkyl moiety having a leaving group, e.g., a moiety such as a halide, a mesylate or a tosylate;

(b) an aryl halide moiety or aryl pseudo halide moiety.

(c) a carboxylic acid moiety activated with a leaving group, for example a carboxylic acid chloride moiety or a carboxylic acid anhydride moiety;

(d) a sulfonic acid moiety activated with a leaving group, for example a sulfonyl chloride moety;

(e) a carbamic acid moiety activated with a leaving group, for example a carbamyl chloride moiety;

(f) a cyanate moiety, for example, potassium cyanate;

(g) an aldehyde or ketone moiety, or a hydrate thereof, or a ketal or acetal thereof;

(h) a carboxylic acid moiety or an amino acid moiety, wherein an amide coupling agent is employed in the reaction; and (i) a moiety that is the product of the reaction of a substituted thiourea moiety and a 1-methyl- or 1-phenyl-2-halopyridinium salt, preferably 2-chloro-1-methylpyridinium iodide, which iodide is also known as Mukaima's reagent;

to form a compound of formula Ia':

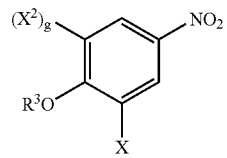

(2) optionally removing said protecting group from said —$X^2$ to yield a compound of formula Ib';

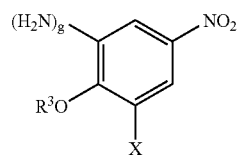

(3) optionally coupling said compound of formula Ib' or a salt of such a compound:

with a compound of formula XI:

$R^1$—A    XI wherein one or more functional groups comprising $R^1$ are optionally protected by chemical protecting groups; and wherein A is a moiety containing an electrophilic reactive center as defined above;

to form a compound of formula Ic':

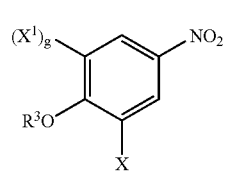

(4) chemically reducing said compound of formula Ic' to give a compound of formula Id':

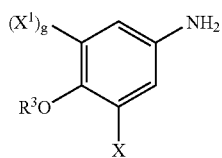
Id'

(5) optionally reacting said compound of formula Id' with:
(a) an aldehyde or ketone under reductive amination conditions; or
(b) alkylating the aniline nitrogen with an alkyl moiety having a leaving group.

To form a compound of formula Ie':

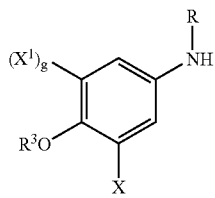
Ie'

Reagents which would effect a reductive amination, include for example, sodium cyanoborohydride in the presence of a weak acid such as acetic acid.

Alkylations of the aniline nitrogen of Id' may be accomplished with alkyl halides or alkyl mesylates.

(6) reacting said compound of formula Ie' with an ester of chlorosulfonylacetic acid, preferably methylchlorosulfonylacetate or ethylchlorosulfonylacetate, to give a compound of formula If':

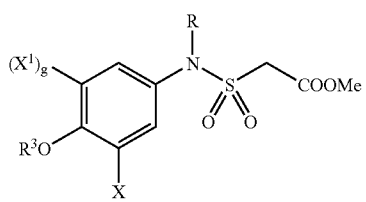
If'

(7) hydrolysing said compound of formula If', to give a compound of formula Ig':

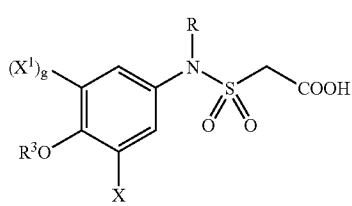
Ig'

(8) reacting said compound of formula Ig' with an aryl aldehyde, H:

H and
(9) optionally removing said protecting groups protecting functionalities comprising $R^1$ to form a compound of formula I:

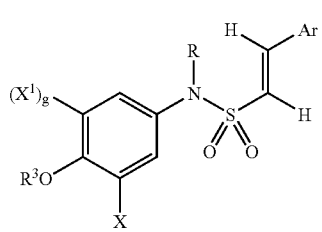
I

In another embodiment, a process for producing a compound of formula IV is provided. The process comprises
(1) coupling a compound of formula Ia'

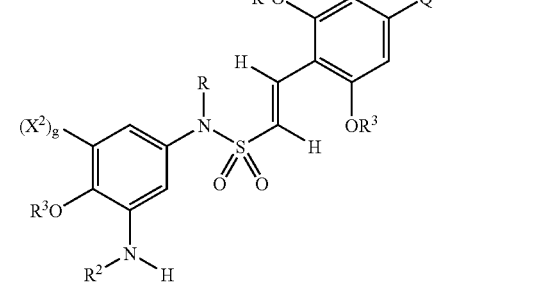
IIIa' with a compound of formula XII $R^1-A^1$  XII wherein one or more functional groups comprising $R^1$ are optionally protected by chemical protecting groups; and
wherein $A^1$ is a carboxylic acid moiety containing a leaving group;
to give a compound of formula IVa:

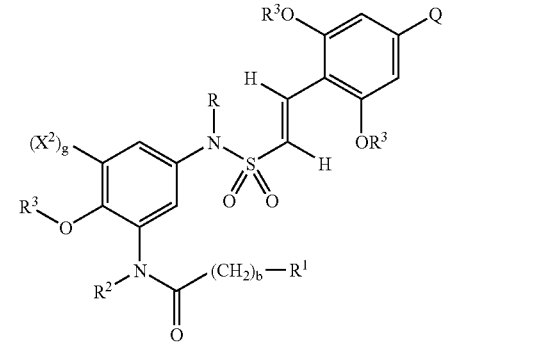
IVa (2) optionally:
(a) when —$X^2$ is —$NH_2$ protected with a protecting group, removing said protecting group from said —$X^2$ to yield a compound of formula IVb; or
(b) when —$X^2$ is —$NO_2$, chemically reducing said —$NO_2$ to —$NH_2$,
to form a compound of formula IVb:

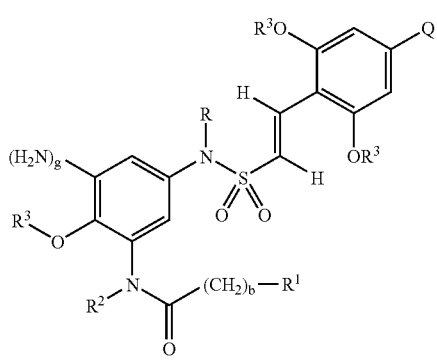

IVb (3) optionally coupling said compound of formula IVb or a salt of such a compound:
with a compound of formula XI:

$R^1$—A    XI wherein one or more functional groups comprising $R^1$ are optionally protected by chemical protecting groups; and A is a moiety containing an electrophilic reactive center defined as above; and (4) optionally removing said protecting groups protecting functionalities comprising $R^1$ to form a compound of formula IV, or a salt of such a compound:

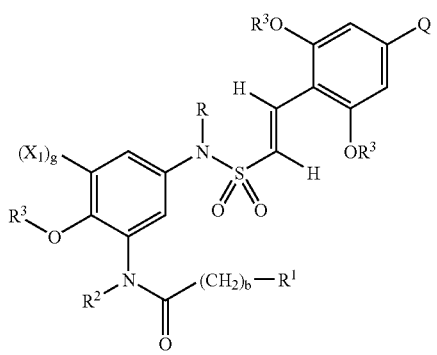

IV

According to another embodiment of the invention, a process for producing a compound according to formula V is provided. The process comprises:
(1) coupling a compound of formula IIIa':

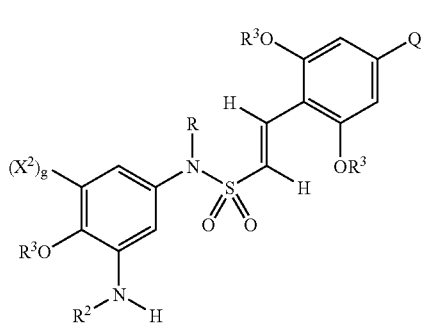

IIIa' with
(a) a compound of formula XIII $R^1$—$A^2$    XIII wherein one or more functional groups comprising $R^1$ are optionally protected by chemical protecting groups; and wherein $A^2$ is a carboxylic acid moiety; and
(b) a coupling reagent such as diisopropylcarbodiimide; to give a compound of Va:

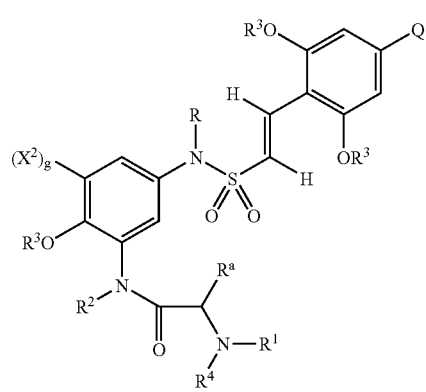

Va (2) optionally:
(a) when —$X^2$ is —$NH_2$ protected with a protecting group; removing said protecting group from said —$X^2$ to yield a compound of formula Vb; or
(b) when —$X^2$ is —$NO_2$, chemically reducing said —$NO_2$ to —$NH_2$
to form a compound of formula Vb:

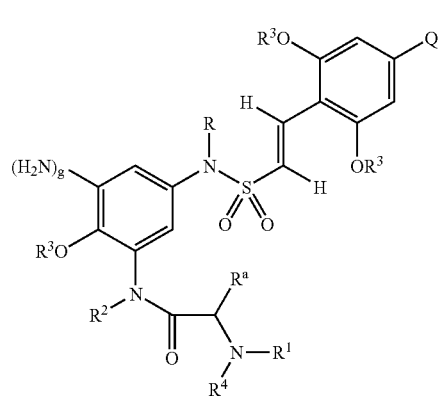

Vb (3) optionally coupling said compound of formula IVb or a salt of such a compound:
with a compound of formula XI:

$R^1$—A    XI wherein one or more functional groups comprising $R^1$ are optionally protected by chemical protecting groups; and
wherein A is a moiety containing an electrophilic reactive center as defined above; and
(4) optionally removing said protecting groups used in the synthesis such as tert-butoxy carbonyl (t-Boc) or 9-fluorenyl-methoxycarbonyl (Fmoc);

to form a compound of formula V, or a salt of such a compound:

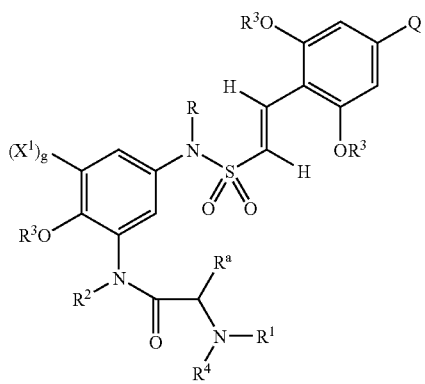

Amide coupling reagents used to couple unactivated carboxylic acids to anilinic amino groups and amino groups associated with peptidic $R^1$ substituents, include for example, reagents such as diisopropyl carbodiimide (DIC) and O-(7-azabenzotriazol-1-yl)-N,N,N',N'-tetramethyluronium hexafluorophosphate (HATU).

In a further embodiment of the invention, a process for producing a compound according to formula VI is provided, comprising:

(1) coupling a compound of formula IIIa':

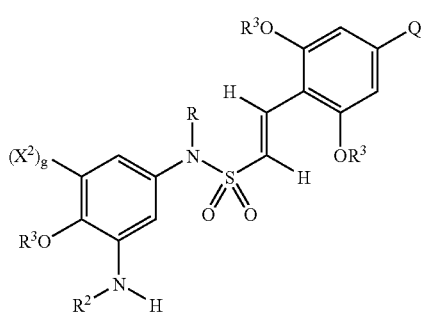

with a compound of formula XIV:

R$^1$—A$^3$   XIV wherein one or more functional groups comprising $R^1$ are optionally protected by chemical protecting groups; and
wherein $A^3$ is a sulfonyl chloride moiety;
to give a compound of VIa:

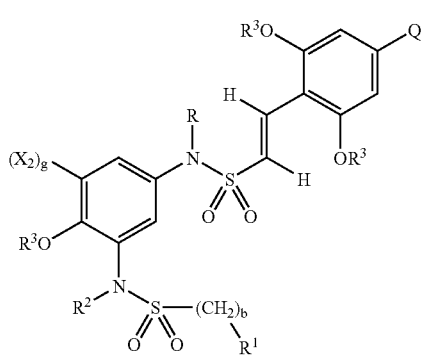

(2) optionally:
(a) when —$X^2$ is —$NH_2$ protected with a protecting group, removing said protecting group from —$X^2$ to yield a compound of formula VIb; or
(b) when —$X^2$ is —$NO_2$, chemically reducing said —$NO_2$ to —$NH_2$,
to form a compound of formula VIb:

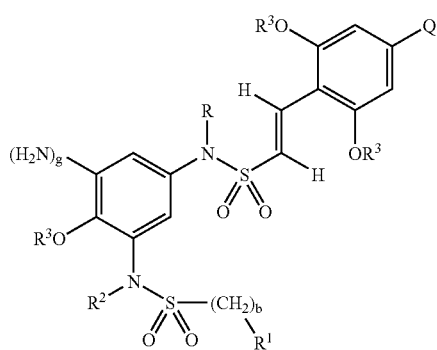

(3) optionally coupling said compound of formula VIb or a salt of such a compound:
with a compound of formula XI:

R$^1$—A   XI wherein one or more functional groups comprising $R^1$ are optionally protected by chemical protecting groups; and
wherein A comprises a moiety containing an electrophilic reactive center as defined above; and.

(4) optionally removing said protecting groups to form a compound of formula VI, or a salt of such a compound:

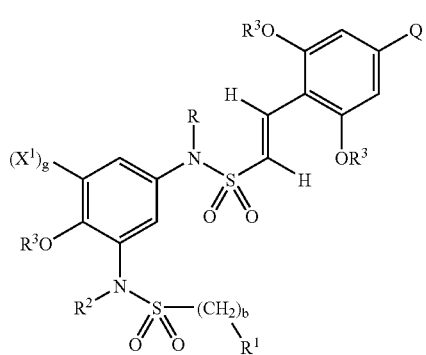

In another embodiment of the invention, a process for producing a compound according to formula VII is provided, comprising:

(1) coupling a compound of formula IIIa'

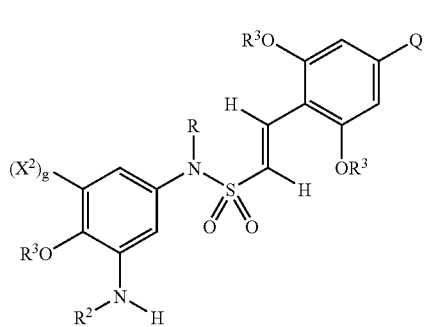

with a compound of formula XV:

$$R^1—A^4 \quad \quad XV$$

wherein one or more functional groups comprising $R^1$ are optionally protected by chemical protecting groups; and wherein $A^4$ is moiety which is a reactive intermediate produce of a substituted thiourea, such as N,N'-bis-(tert-butoxycarbonyl)thiourea and a 1-methyl- or 1-phenyl-2-halopyridinium salt, preferably 2-chloro-1-methylpyridinium iodide;

to give a compound of VIIa:

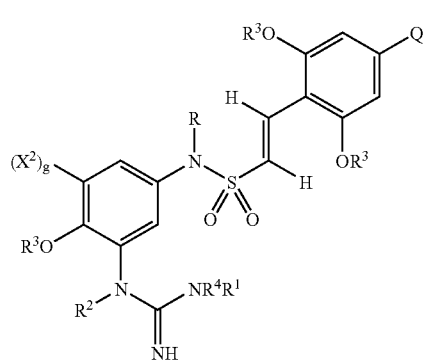

VIIa (2) optionally:
(a) when —$X^2$ is —$NH_2$ protected with a protecting group, removing said protecting group from —$X^2$ to yield a compound of formula VIIb; or
(b) when —$X^2$ is —$NO_2$, chemically reducing said —$NO_2$ to —$NH_2$ to form a compound of formula VIIb:

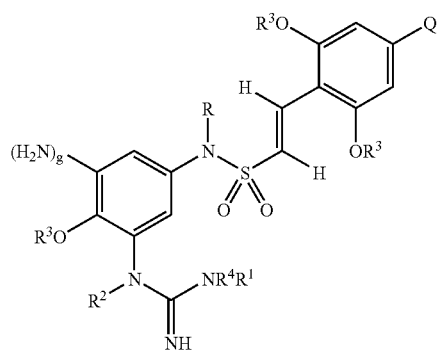

VIIb (3) optionally coupling said compound of formula VIIb or a salt of such a compound:
with a compound of formula XI:

$$R^1—A \quad \quad XI$$

wherein one or more functional groups comprising $R^1$ are optionally protected by chemical protecting groups; and wherein A comprises a moiety containing an electrophilic reactive center as defined above; and (4) optionally removing said protecting groups to form a compound of formula VII, or a salt of such a compound:

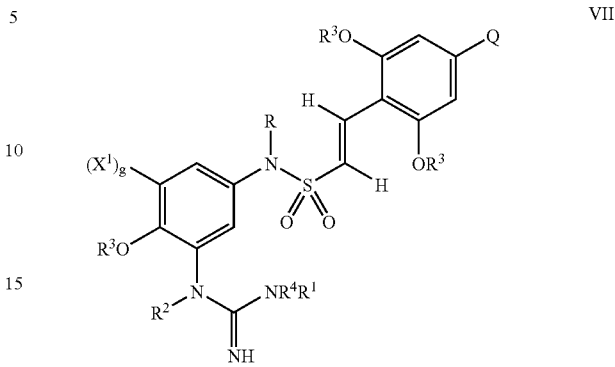

VII

In another embodiment of the invention, a process for producing a compound according to formula VIII is provided, comprising
(1) coupling a compound of formula IIIa':

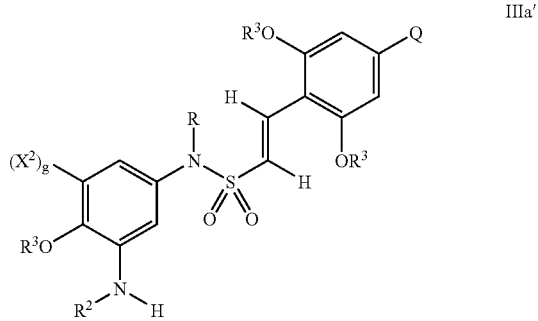

IIIa' with a compound of formula XVI $$R^1—A^5 \quad \quad XVI$$

wherein one or more functional groups comprising $R^1$ are optionally protected by chemical protecting groups; and
wherein $A^5$ is an alkyl moiety containing a leaving group;
to give a compound of VIIIa:

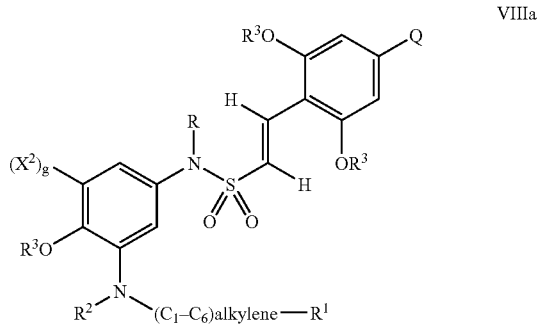

VIIIa (2) optionally
(a) when —$X^2$ is —$NH_2$ protected with a protecting group, removing said protecting group from —$X^2$ to yield a compound of formula VIIIb; or
(b) when —$X^2$ is —$NO_2$, chemically reducing said —$NO_2$ to —$NH_2$, to form a compound of formula VIIIb:

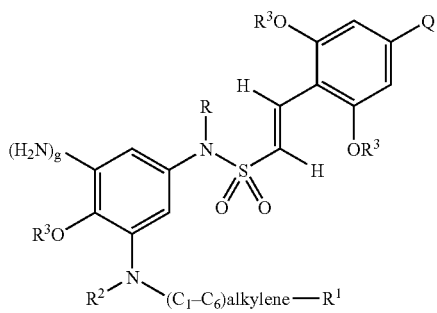
VIIIb (3) optionally coupling said compound of formula VIIIb or a salt of such a compound:
with a compound of formula XI:

R$^1$—A  XI wherein one or more functional groups comprising R$^1$ are optionally protected by chemical protecting groups; and
wherein A comprises a moiety containing an electrophilic reactive center as defined above; and
(4) optionally removing said protecting groups to form a compound of formula VIII, or a salt of such a compound:

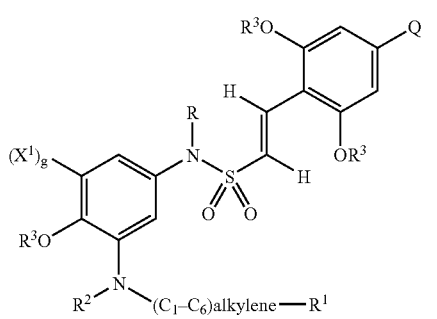
VIIIb

Appropriate leaving groups for alkyl moieties include for example, groups such as halides, mesylates or tosylates.

In a further embodiment of the invention, a process for producing a compound of formula IX is provided, comprising:
(1) coupling a compound of formula IIIa'

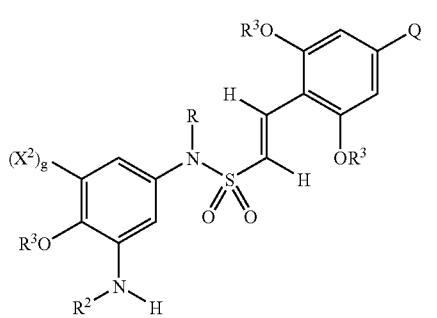
IIIa' wherein R$^2$ is —H;
with a compound of formula XVII

R$^1$—A$^6$  XVII wherein one or more functional groups comprising R$^1$ are optionally protected by chemical protecting groups; and wherein A$^6$ is a moiety containing an aldehyde or ketone moiety, a hydrate thereof, or a ketal or acetal thereof;
to give a compound of IXa:

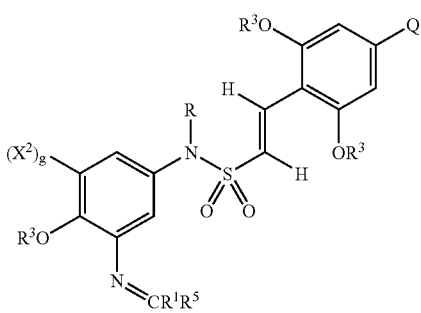
IXa (2) optionally
(a) when —X$^2$ is —NH$_2$ protected with a protecting group, removing said protecting group from —X$^2$ to yield a compound of formula IXb; or
(b) when —X$^2$ is —NO$_2$, chemically reducing said —NO$_2$ to —NH$_2$,
to form a compound of formula IXb:

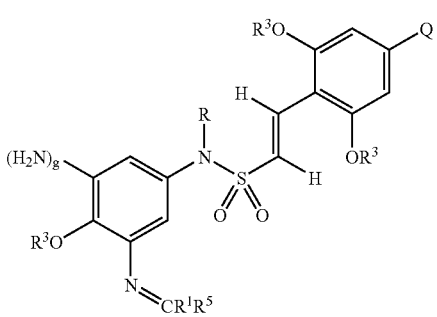
IXb (3) optionally coupling said compound of formula IXb or a salt of such a compound:
with a compound of formula XI:

R$^1$—A  XI wherein one or more functional groups comprising R$^1$ are optionally protected by chemical protecting groups; and
wherein A comprises a moiety containing an electrophilic reactive center as defined above; and
(4) optionally removing said protecting groups to form a compound of formula IX, or a salt of such a compound:

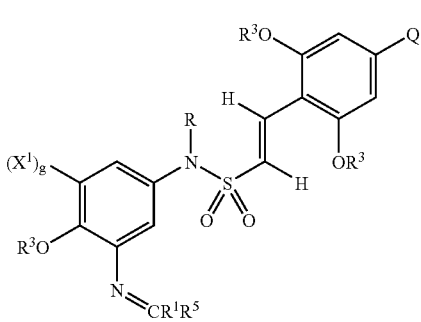
IX

In another embodiment of the invention, a process for producing a compound of formula X is provided, comprising:

(1) coupling a compound of formula IIIa':

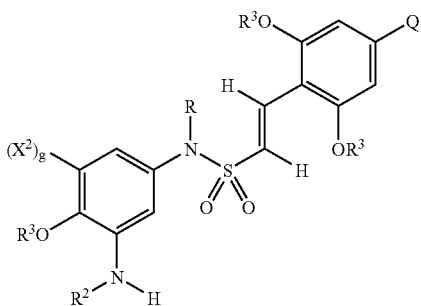

IIIa' with a compound of formula XVIII

R¹—A⁷    XVIII wherein one or more functional groups comprising R¹ are optionally protected by chemical protecting groups; and wherein (a) if A⁷ is a cyanate moiety, then R¹ is selected from the group consisting of —H, $(C_1-C_6)$alkyl and aryl; and R⁴ is —H; and b) if A⁷ is a carbamic acid moiety activated with a leaving group, then R¹ and R⁴ of formula X are as defined above; to give a compound of the formula Xa:

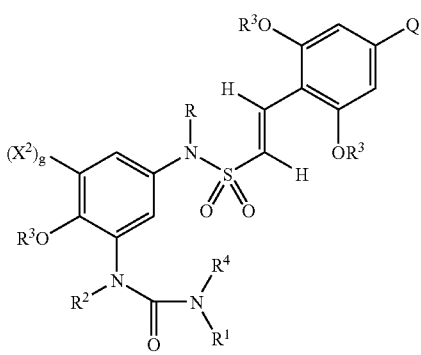

Xa (2) optionally:
(a) when —X² is —NH₂ protected with a protecting group, removing said protecting group from —X² to yield a compound of formula Xb; or
(b) when —X² is —NO₂, chemically reducing said —NO₂ to —NH₂,
to form a compound of formula Xb:

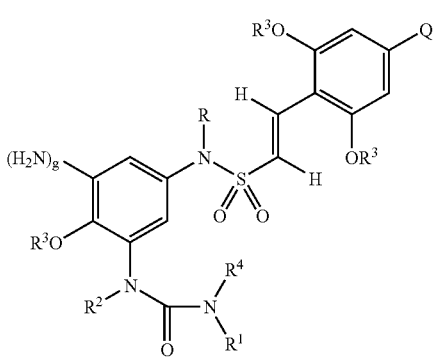

Xb (3) optionally coupling said 5-NH₂ compound of formula Xb or a salt of such a compound:
with a compound of formula XI

R¹—A    XI wherein one or more functional groups comprising R¹ are optionally protected by chemical protecting groups; and wherein A is a moiety containing an electrophilic reactive center as defined above; and (4) optionally removing said protecting groups to form a compound of formula X, or a salt of such a compound:

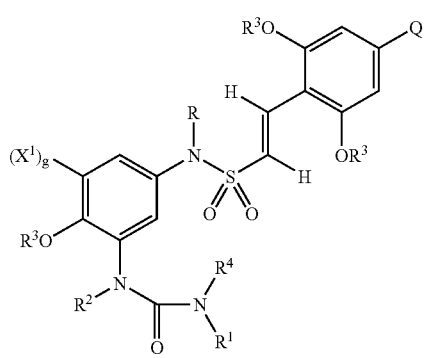

X

In yet another embodiment of the invention, a conjugate of the formula I-L-Ab is provided wherein I is a compound of formula I; Ab is an antibody; and —L— is a single bond or a linking group covalently linking said compound of formula I to said antibody.

In a another embodiment of the invention, a conjugate of the formula III-L-Ab is provided wherein III is a compound of formula m; Ab is an antibody; and —L— is a single bond or a linking group covalently linking said compound of formula III to said antibody.

In a further embodiment of the invention, a conjugate of the formula I'-L-Ab is provided wherein I' is a compound of formula I'; Ab is an antibody; and —L— is a single bond or a linking group covalently linking said compound of formula I' to said antibody.

In a preferred sub-embodiment of the aforesaid conjugates of the formulae I-L-Ab, I'-L-Ab and III-L-Ab, said antibody (Ab) is a monoclonal antibody or a monospecific polyclonal antibody.

In a more preferred sub-embodiment of the aforesaid conjugates of the formulae I-L-Ab, I'-L-Ab and III-L-Ab, the aforesaid antibody (Ab) is a tumor-specific antibody.

In yet a further embodiment of the present invention, there is provided a compound of formula I derivatized as a substrate for a β-lactamase enzyme.

A pharmaceutical composition is also provided comprising a pharmaceutically acceptable carrier and one or more compounds of formula I above, or a pharmaceutically acceptable salt of such compound.

A pharmaceutical composition is additionally provided, comprising a pharmaceutically acceptable carrier and at least one conjugate according to formula I-L-Ab, I'-L-Ab or III-L-Ab.

According to another embodiment of the invention, a method of treating an individual for a proliferative disorder, particularly cancer, is provided, comprising administering to said individual an effective amount of a compound according to formula I, or a pharmaceutically acceptable salt of such compound, alone or in combination with a pharmaceutically acceptable carrier.

In another embodiment, a method of treating an individual an individual for a proliferative disorder, particularly cancer, is provided, comprising administering to said individual an effective amount of at least one conjugate of the formula I-L-Ab, I'-L-Ab or III-L-Ab.

In another embodiment of the invention, a method of inhibiting growth of tumor cells in an individual afflicted with cancer is provided comprising administering to said individual an effective amount of a compound according to formula I, or a pharmaceutically acceptable salt of such compound, alone or in combination with a pharmaceutically acceptable carrier.

In another embodiment of the invention, a method of inhibiting growth of tumor cells in an individual afflicted with cancer is provided comprising administering to said individual an effective amount of at least one conjugate of the formula I-L-Ab, I'-L-Ab or III-L-Ab, alone or in combination with a pharmaceutically acceptable carrier.

In another embodiment, a method of inducing apoptosis of cancer cells, more preferably tumor cells, in an individual afflicted with cancer is provided, comprising administering to said individual an effective amount of a compound according to formula I, or a pharmaceutically acceptable salt of such compound, alone or in combination with a pharmaceutically acceptable carrier.

In another embodiment, a method of inducing apoptosis of cancer cells, more preferably tumor cells, in an individual afflicted with cancer is provided, comprising administering to said individual an effective amount of at least one conjugate of the formula I-L-Ab, I'-L-Ab or III-L-Ab, alone or in combination with a pharmaceutically acceptable carrier.

The amino-substituted styryl sulfonanilides of the invention are characterized by cis-trans isomerism resulting from the presence of a double bond. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127–138. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher ranking groups are on opposite sides of the double bond, is designated E (for the German word "entgegen", which means "opposite"). The compounds of the present invention have the E configuration as shown below.

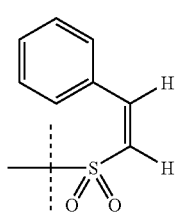

Z configuration

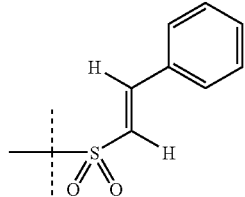

E configuration

The term "acyl" means a radical of the general formula —C(=O)—R, wherein —R is hydrogen, hydrocarbyl, amino or alkoxy." Examples include for example, acetyl (—C(=O)CH$_3$), propionyl(—C(=O)CH$_2$CH$_3$), benzoyl (—C(=O)C$_6$H$_5$). Phenylacetyl (—C(=O)CH$_2$C$_6$H$_5$), carboethoxy (—CO$_2$Et), and dimethylcarbamoyl (—C(=O)N(CH$_3$)$_2$).

The term "alkyl", by itself or as part of another substituent means, unless otherwise stated, a straight, branched or cyclic chain hydrocarbon radical, including di- and multi-radicals, having the number of carbon atoms designated (i.e. C$_1$–C$_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is (C$_1$–C$_3$)alkyl, particularly ethyl, methyl and isopropyl.

The term "alkylene", by itself or as part of another substituent means, unless otherwise stated, a divalent straight, branched or cyclic chain hydrocarbon radical.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers. Preferred are (C$_1$–C$_3$)alkoxy, particularly ethoxy and methoxy.

The term "alkenyl" employed alone or in combination with other terms, means, unless otherwise stated, a stable monounsaturated or di-unsaturated hydrocarbon radical straight chain, branched chain or cyclic hydrocarbon group having the stated number of carbon atoms. Examples include vinyl, propenyl(allyl), crotyl, isopentenyl, butadienyl, 1,3-pentadienyl, 1,4-pentadienyl, cyclopentenyl, cyclopentadienyl and the higher homologs and isomers. A divalent radical derived from an alkene is exemplified by —CH=CH—CH$_2$—.

The term "amine" or "amino" refers to radicals of the general formula —NRR', wherein R and R' are independently selected from hydrogen or a hydrocarbyl radical, or wherein R and R' combined form a heterocycle. Examples of amino groups include: —NH$_2$, methyl amino, diethyl amino, anilino, benzyl amino, piperidinyl, piperazinyl and indolinyl.

The term "carbamyl" means the group —C(=O)NRR', wherein R and R' are independently selected from hydrogen or a hydrocarbyl radical, or wherein R and R' combined form a heterocycle. Examples of carbamyl groups include: —C(=O)NH$_2$ and —C(=O)N(CH$_3$)$_2$.

The term "carboxy(C$_1$–C$_3$)alkoxy" means a radical in which the carboxy group —COOH is attached to a carbon of a straight or branched chain alkoxy group containing one to three carbon atoms. The radical thus contains up to four carbon atoms. Examples include: —O(CH$_2$)$_3$CO$_2$H and —O(CH$_2$)$_2$CO$_2$H.

The term "cycloalkyl" refers to ring-containing alkyl radicals;

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$.

The term "heteroalkenyl" by itself or in combination with another term means, unless otherwise stated, a stable straight or branched chain monounsaturated or di-unsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

The term "hydroxyalkyl" means an alkyl radical wherein one or more of the carbon atoms is substituted with hydroxy. Examples include —$CH_2$CH(OH)$CH_3$ and —$CH_2CH_2$OH.

The terms "halo" or "halogen" by themselves or as part of another substituent mean, unless otherwise stated, a fluorine, chlorine, bromine, or iodine atom.

The term "di($C_1$–$C_6$)alkylamino($C_2$–$C_6$)alkoxy" means (alkyl)$_2$N($CH_2$)$_n$O— wherein the two alkyl chains connected to the nitrogen atom independently contain from one to six carbon atoms, preferably from one to three carbon atoms, and n is an integer from 2 to 6. Preferably, n is 2 or 3. Most preferably, n is 2, and the alkyl groups are methyl, that is, the group is the dimethylaminoethoxy group, ($CH_3$)$_2$N$CH_2CH_2$O—.

The term "phosphonato" means the group —PO(OH)$_2$.

The term "sulfamyl" means the group —$SO_2$NRR', wherein R and R' are independently selected from hydrogen or a hydrocarbyl radical, or wherein R and R' combined form a heterocycle. Examples of sulfamyl groups include: —$SO_2NH_2$, —$SO_2$N($CH_3$)$_2$ and —$SO_2$NH($C_6H_5$).

The term "aromatic" refers to a carbocycle or heterocycle having one or more polyunsaturated rings having aromatic character (4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "aryl-($C_1$–$C_3$)alkyl" means a radical wherein a one to three carbon alkylene chain is attached to an aryl group, e.g., —$CH_2CH_2$-phenyl. Similarly, the term "heteroaryl-($C_1$–$C_3$)alkyl" means a radical wherein a one to three carbon alkylene chain is attached to a heteroaryl group, e.g., —$CH_2CH_2$-pyridyl. The term "substituted aryl-($C_1$–$C_3$)alkyl" means an aryl-($C_1$–$C_3$)alkyl radical in which the aryl group is substituted. The term "substituted heteroaryl-($C_1$–$C_3$)alkyl" means a heteroaryl-($C_1$–$C_3$)alkyl radical in which the heteroaryl group is substituted.

The term "heterocycle" or "heterocyclyl" or "heterocyclic" by itself or as part of another substituent means; unless otherwise stated, an unsubstituted or substituted, stable, mono- or multicyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character.

Examples of non-aromatic heterocycles include monocyclic groups such as: Aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-traizolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: Indolyl, particularly 3-, 4-, 5-, 6- and 7-indolyl, indolinyl, quinolyl, tetrahydroquinolyl, isoquinolyl, particularly 1- and 5-isoquinolyl, tetrahydroisoquinolyl, cinnolinyl, quinoxalinyl, particularly 2- and 5-quinoxalinyl, quinazolinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative, not limiting.

The term "hydrocarbyl" refers to any moiety comprising only hydrogen and carbon atoms.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

Where a substituent is an alkyl or alkoxy group, the carbon chain may be branched, straight or cyclic, with straight being preferred.

The term "antibody" is intended to encompass not only intact antigen-binding immunoglobulin molecules, but also to include antigen-binding fragments thereof such as Fab, Fab' and F(ab')$_2$ fragments, or any other fragment retaining the antigen-binding ability of an intact antibody.

The term "humanized antibody" refers to an antibody that has its complementary determining regions (CDR's) derived from a non-human species immunoglobulin, and the remainder of the antibody molecule derived from a human immunoglobulin.

The term "chimeric antibody" means an antibody comprising a variable region and a constant region derived from different species.

The term "humanized chimeric antibody" is meant a chimeric antibody in which at least the constant region is human-derived.

The term "monospecific polyclonal antibody" means an antibody preparation comprising multiple antibody species having specificity for a single antigen.

The term "monovalent peptidyl moiety" refers to a peptide radical as a substituent on a molecule of formula I. Such a radical has a chemical structure that varies from the structure of the corresponding peptide in that the structural component of the peptide, ie., an alpha amino group, a sidechain amino group, an alpha carboxyl group or a sidechain carboxyl group, will form a different functionality when bonded to the molecule of which it is to be a substituent. For example, when a peptide as shown below:

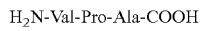

H₂N-Val-Pro-Ala-COOH is a substituent on a compound of formula I, and said peptide is coupled to a compound of formula I such that a carboxyl moiety of said peptide is coupled to a free amine moiety on formula I, there is a functional elimination of H$_2$O that results in the formation of an amide bond. As a practical result, the corresponding monovalent peptidyl substituent will be as shown to the left of the dotted line in the depiction below of the aforementioned peptide bonded to a compound of formula I:

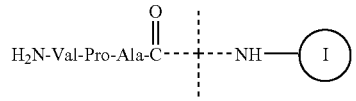

The term "effective amount" when used to describe therapy to a patient suffering from a proliferative disorder, refers to the amount of a compound of formula I that inhibits the growth of tumor cells or alternatively induces apoptosis of cancer cells, preferably tumor cells, resulting in a therapeutically useful and selective cytotoxic effect on proliferative cells when administered to a patient suffering from a cancer or other disorder which manifests abnormal cellular proliferation.

DETAILED DESCRIPTION OF THE INVENTION

According to the present invention, amino-substituted sulfonanilides and salts thereof are believed to selectively inhibit proliferation of cancer cells, and kill various tumor cell types without killing normal cells. Cells are killed at concentrations where normal cells may be temporarily growth-arrested but not killed.

The amino-substituted sulfonanilides compounds of the invention are believed to inhibit the proliferation of tumor cells, and for some compounds, induce cell death. Cell death results from the induction of apoptosis. The compounds are believed effective against a broad range of tumor types, including but not limited to the following: breast, prostate, ovarian, lung, colorectal, brain (i.e, glioma) and renal. The compounds are also effective against leukemic cells.

The amino-substituted sulfonanilides compounds are also believed useful in the treatment of non-cancer proliferative disorders, including but not limited to the following: hemangiomatosis in newborn, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

The amino-substituted sulfonanilides may be prepared by one of two general methods. In the synthesis methods to follow, reference to "Ar" is intended to include substituted and unsubstituted aryl, and also substituted and unsubstituted heteroaryl.

General Mathod A as outlined in Scheme 1, utilizes a Knoevenagel-type condensation according to Oliver et al., Synthesis 321–322 (May 1975). This synthesis relies on the condensation of an arylaminosulfonylacetic acid intermediate G with an appropriate aryl aldehyde H. The entire disclosure of Oliver et al. is incorporated herein by reference.

Scheme 1:

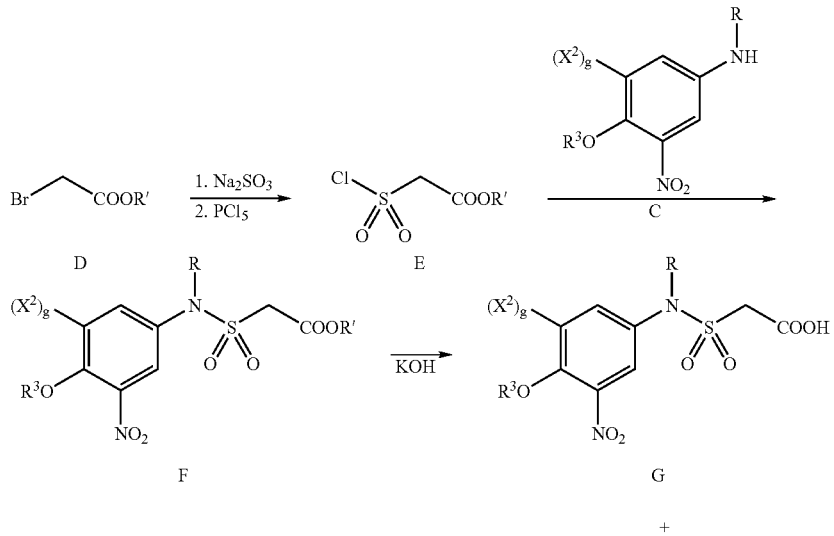

-continued

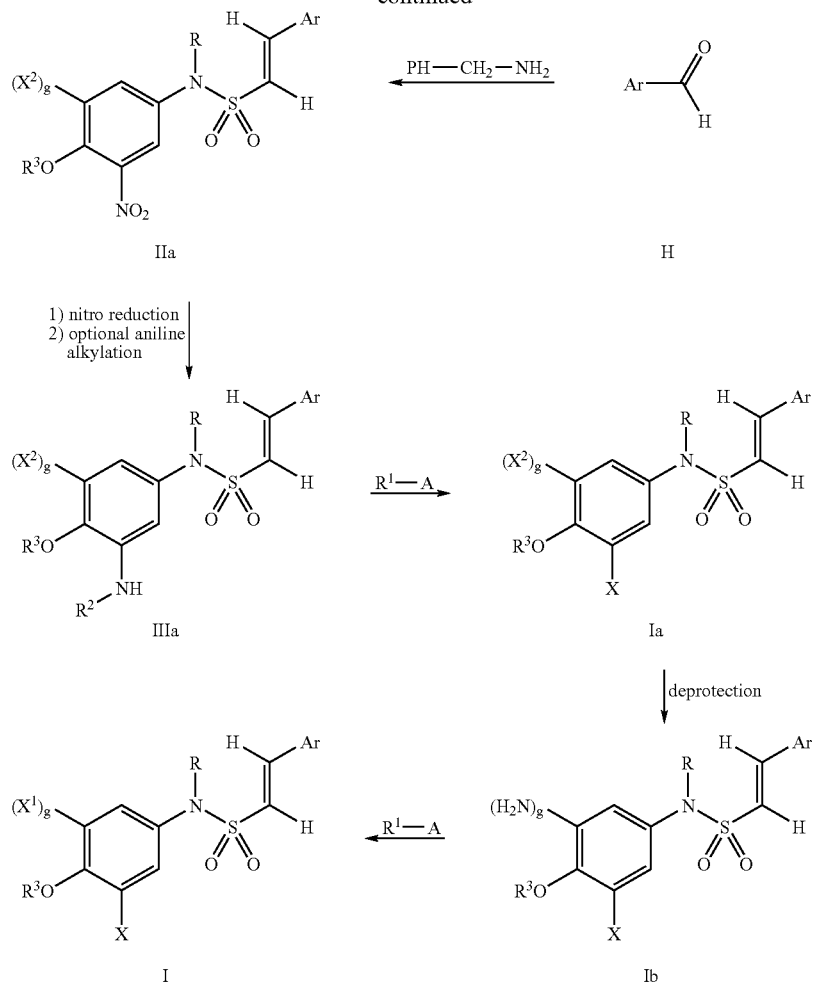

According to Scheme 1, a methyl (or ethyl) β-chlorosulfonylacetate intermediate E is prepared from methyl (or ethyl) bromoacetate (R'=methyl or ethyl). To do this, methyl (or ethyl) bromoacetate is reacted with sodium sulfate to form the sodium sulfoacetate intermediate $Na_2OSO_2CH_2CO_2R'$. Potassium sulfate may be used as a substitute for sodium sulfate. The sodium sulfoacetate intermediate is then reacted with a chlorinating agent, preferably $PCl_5$, to form the methyl (or ethyl) β-chlorosulfonylacetate intermediate E. Reaction of intermediate E with the aromatic amine C yields the anilinosulfonylacetate intermediate F. The latter reaction is conducted in a nonprotic solvent in the presence of a base. The same compound may serve as both the nonprotic solvent and the base. Such dual-function solvents include, for example, pyridine, substituted pyridines, trimethylamine, triethylamine and DIPEA. The anilinosulfonylacetate F is then converted to the corresponding anilinosulfonylacetic acid compound G by any base capable of hydrolyzing the ester function of F to an acid. Such bases include KOH and NaOH, for example. In the final step, the anilinosulfonylacetic acid compound is condensed with an aromatic aldehyde H in the presence of a basic catalyst via a Knoevenagel reaction and decarboxylation of an intermediate. Basic catalysts include, for example, pyridine and benzylamine. The reaction yields the desired amino-substituted sulfonanilide of formula I.

The following are more detailed procedures for the preparation of the formula I compounds, according to Scheme 1 (General Method A).

General Method A

Step 1: Preparation of 3-Nitro-p-Anisidine

To a stirring solution of 4-fluoro-3-nitroaniline (10 mmol) in 30 mL of anhydrous methanol, was added sodium methoxide, portionwise over a period of 15 minutes. Throughout the addition, the reaction temperature was maintained below 25° C. After the addition was complete, the solution was heated to reflux for 21 hours. The reaction progress was monitored by TLC. When the reaction was complete, the mixture was cooled to 0° C. The pH of the mixture was adjusted to 4.0 with hydrochloric acid followed by the addition of water. The solution was then extracted with diethylether (3×50 mL) and the combined ether extract was washed with brine and concentrated under vacuum to yield 3-nitro-p-anisidine. (m.p. 51–53° C.; 84% yield).

Step 2: Preparation of Methyl-3-nitro-4-methoxyanilinesulfonyl acetate

A solution of chlorosulfonyl acetylchloride (22.4 mmol) in anhydrous ether (40 mL) was cooled to 0° C. Anhydrous methanol (22.5 mmol) was added in one portion. The reaction mixture was maintained at 0° C. for 2.5 to 3 hours and the reaction progress was monitored by TLC. When the reaction was complete by TLC, the ether was removed under reduced pressure. The crude product was used in the next step without further purification.

A solution of 3-nitro-p-anisidine (20 mmol) and triethylamine (20 mmol), in dichloromethane (100 mL) was stirred at 10° C. for 15 minutes. To this solution was added dropwise a solution of methyl chlorosulfonyl acetate (20 mmol), in dichloromethane (30 mL). After the addition was complete, the reaction mixture was allowed to warm to room temperature and stirred at room temperature for 3 hours. When the reaction was complete by TLC, water was added, and the resulting mixture was stirred for 15 min. The organic layer was separated and concentrated to yield a viscous liquid. The crude product was purified by column chromatography on silica, eluting with 1:1 ethylacetate/hexane. The desired methyl-3-nitro-4-methoxyanilinesulfonyl acetate was obtained as a white crystalline solid. (m.p. 115–119° C.; yield 78%).

Step 3: Preparation of 3-nitro-4-methoxy anilinesulfonylacetic acid

To a round-bottomed flask was added 5.5 g of methyl 4-methoxy-3-nitroanilinesulfonyl acetate. To this was added portionwise a solution of sodium hydroxide (4.88 g in 110 mL of water). The resulting reaction mixture was stirred at room temperature for 3 h. The reaction progress was monitored by TLC. After the reaction was complete; the mixture was cooled to 0° C. HCl (12M) was added slowly to bring the mixture to pH 3.0–4.0. The acidified mixture was stirred for 20 min at 0° C. An off-white solid slowly precipitated. The solid product was separated by filtration and dried under vacuum. (m.p. 154–156° C.; yield 75%).

Step 4: Preparation of 2,4,6-Trimethoxy styryl-N-(4-methoxy-3-nitrophenyl) Sulfonamide A solution of 4-methoxy-3-nitroanilinesulfonylacetic acid (10 mmol) and 2,4,6-trimethoxy-benzaldehyde (10 mmol) in glacial acetic acid (15 mL) was stirred at room temperature for 10 min. A catalytic amount of benzylamine (300 microliters) was added to the solution. The solution was then refluxed for 8 h. The reaction mixture was then cooled to room temperature. To the cooled reaction mixture was added ethyl acetate. A solid precipitate formed and was separated by filtration. Additional of ethyl acetate (30 mL) was added and the resulting mixture was washed sequentially with saturated sodium bicarbonate, dilute HCL and brine. The organic layer was dried over anhydrous sodium sulfate and then concentrated under vacuum. The solid residue obtained was recrystallized from 2-propanol. (m.p 177–179° C.; yield 48–52%).

Step 5: Preparation of 2,4,6-Trimethoxy styryl-N-(3-Amino-4-methoxyphenyl) Sulfonamide 2,4,6-trimethoxystyryl-N-(4-methoxy-3-nitrophenyl)sulfonamide (7 mmol) was dissolved in ethanol (55 mL) in a round bottomed flask. Palladium catalyst (5% Pd/C, 275 mg) was added. Hydrazine hydrate (182 mmol) was then added in one porion. The resulting misture was refluxed for 5 h and the reaction prgress was monitored by TLC. When the reaction was complete, the palladium catalyst was removed by filtration and the filtrate was poured into a beaker containing ice cold water. The solution was stirred and a solid precipitate formed. The precipitated material was separated by filtration and dried in vacuum. (m.p. 143–145; yield 48%).

Alternate Step 5: Alternate reduction procedure via sodium dithionite

A solution of 2,4,6-trimethoxy styryl-N-(4-methoxy-3-nitrophenyl)sulfonamide (1.3 mmol) was dissolved in a 2:1 mixture of acetone and water (10 mL) and heated to 50° C. After 30 min at 50° C., sodiumdithionite ($Na_2S_2O_4$) (26.3 mmol) was added slowly, and the resulting mixture was maintained at reflux (50° C.) for 1 hour, and then cooled to room temperature. Water was added and a precipitate formed. The solid product was washed with aqueous $NaHCO_3$, and then taken up in ethyl acetate and dried over anhydrous $Na_2SO_4$. The solvent was removed under reduced pressure and the crude product was purified by column chromatography. (m.p. 143–145° C.)

Step 6: Method for coupling carboxylic acids to (E)-2,4,6-trimethoxystyryl-N[(3-amino)-4-methoxyphenyl]sulfonamide A solution of (E)-2,4,6-trimethoxystyryl-N[(3-amino)-4-methoxyphenyl]sulfonamide (1 mmol), aromatic or aliphatic carboxylic acid (1.5 mmol), hydroxybenzotriazole (1.5 mmol) and 1,3-diisopropylcarbodiimide (1.4 mmol) in dimethylformamide (8 mL) is taken in a reaction vessel. The reaction vessel is connected to a manual shaker and is shaken at room temperature for 5 h. Ethyl acetate (20 mL) is then added to the solution and any precipitated material is removed by filtration. The solution is dried under vacuum and the residue is treated with ethanol (20 mL) to give (E)-2,4,6-trimethoxystyryl-N-[(3-aryl or alkylamido)-4-methoxyphenyl]sulfonamide.

Alternate Step 6: Coupling of carboxylic acid halides or sulfonyl halides to 2,4,6-Trimethoxy styryl-N-(3-Amino-4-methoxyphenyl) Sulfonamide To a solution of aromatic or alphatic acid chloride or sulfonyl chloride (10 mmol) in tetrahydrofuran (40 mL) was added dropwise a solution of 2,4,6-trimethoxy styryl-N-(3-amino-4-methoxyphenyl)sulfonamide (10 mmol in 10 mL of tetrahydrofuran). The resulting mixture was stirred overnight and the reaction progress was monitored by TLC. When the reaction was complete, the solvent was removed under vacuum. The residue was taken up in dichloromethane (50 mL) and washed with water (50 mL). The sepatated dichloromethane layer was dried over anhydrous sodium sulfate and concentrated to yield 2,4,6-trimethoxy styryl-N-3-substituted amido-4-methoxyphenyl) sulfonamide.

The synthetic sstrategy for preparation of compounds of the invention is flexible so as to allow for rearrangement of the assembly steps to accommodate for functional group sensitivity or to allow for diversity elements at the 3- (and optionally the 5-position) anilino nitrogens when employing General Method A, or allow for diversification of the Ar functionality when employing General Method B as outlined in Scheme 2 below. For synthetic strategy employing General Method B, a modification in the aniline C is required. Use of the intermediate 2-alkoxy-5-nitroaniline $C^1$ allows for deriviatization of the 3- and optionally the 5-position aniline nitrogens, and thereafter reacting with sulfonyl chloride, E; hydrolysis to intermediate G' and reaction with an aromatic aldehyde H to yield a compound of formula I. The synthetic strategy of General Method B is depicted in Scheme 2 below.

drofuran (THF). The solution is stirred overnight and the completion of the reaction is monitored by TLC. The solvent is removed and the residue is taken in dichloromethane and

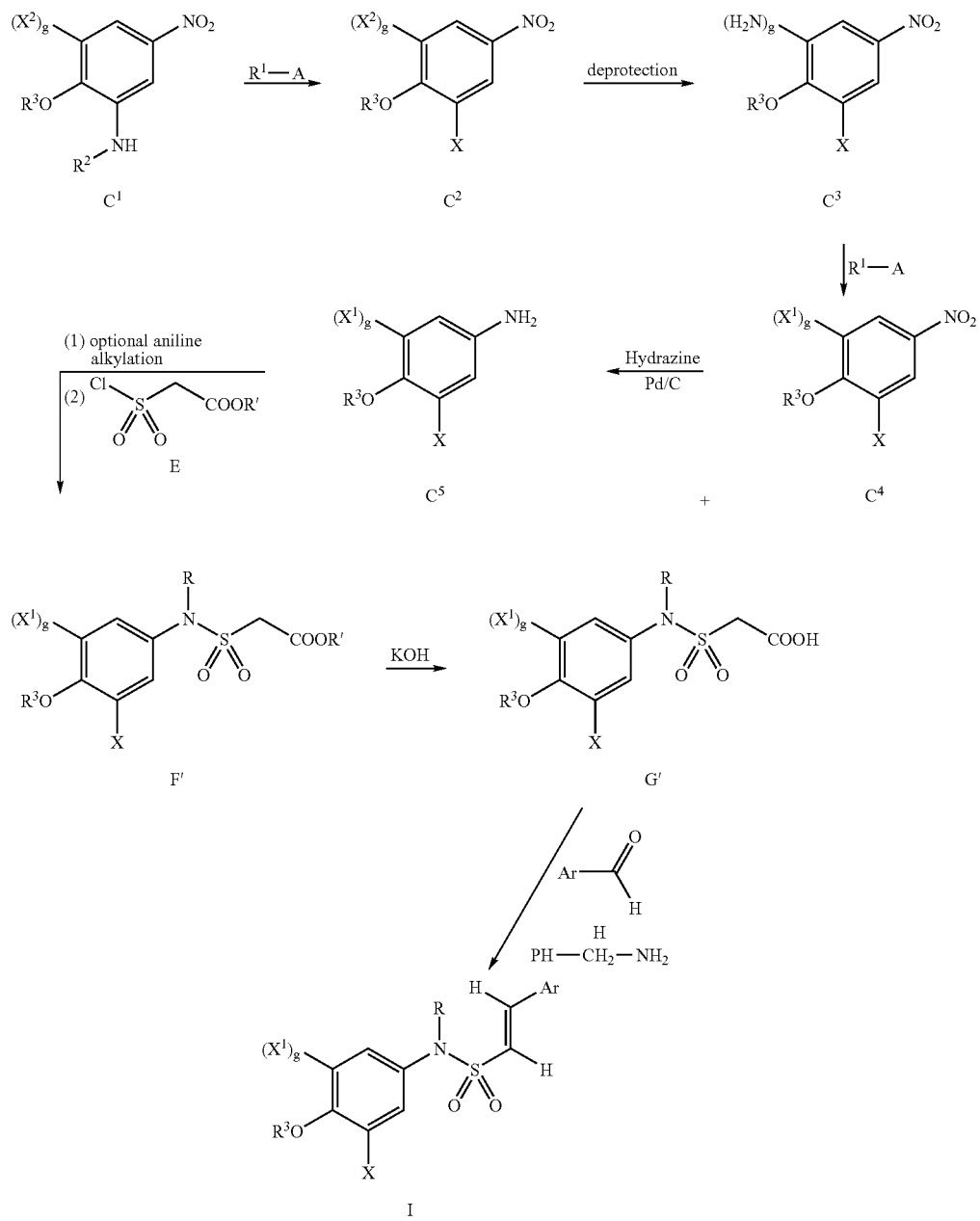

The following are more detailed procedures for the preparation of the formula I compounds, according to Scheme 2 (General Method B).

General Method B:

Step 1: Acylation of an Aniline Compound

To a solution of aromatic or alphatic acid chloride (10 mmol) in tetrahydrofuran (40 mL) is added drop wise a solution of 2-methoxy-5-nitroaniline (10 mmol) in tetrahywashed with water. The organic layer is dried over anhydrous sodium sulfate and evaporated to give 2-amido-4-nitroanisole.

A solution of 2-amido-4-nitroanisole (1.3 mmol) in acetone water (10:5) is heated at 50° C. After 30 min, sodium hydrosulfite ($Na_2S_2O_4$) (26.3 mmol) is added slowly, and the mixture is heated at reflux (50° C., 1 h.), cooled to room temperature and water is added. The product is rinsed with $NaHCO_3$, and then isolated by extraction with ethyl acetate. The organic layer is dried over anhydrous Na₂SO₄. The solvent is removed under reduced pressure and the crude product is purified by passing through a silica column.

Step 2: Preparation of Methyl-3-amido-4-methoxyanilinesulfonyl Acetate

To a solution of chlorosulfonyl acetylchloride (22.4 mmol) in anhydrous ether (40 mL) cooled to 0° C., anhydrous methanol (22.5 mmol) is added in one portion. The reaction mixture is kept at that temperature for 2.5 to 3 hours and the completion of the reaction is monitored by TLC. Once the reaction completion is established, the ether is removed under reduced pressure and proceeded to the next step without purification.

A solution of 3-amido-p-anisidine (20 mmol), triethylamine (20 mmol), in dichloromethane (100 mL) is kept at 10° C. for 15 minutes. To this solution, methyl chlorosulfonyl acetate (20 mmol) in dichloromethane (30 mL) is added dropwise. After the addition is complete, the reaction mixture is stirred at room temperature for 3 h. After the reaction is complete (established by TLC), water is added to the reaction mixture and stirred for 15 min. The separated organic layer is concentrated and purified by column chromatography.

Step 3: Preparation of 3-amido-4-methoxy anilinesulfonylacetic Acid

To a round-bottomed flask is added 5.5 g of methyl 4-methoxy-3-nitroanilinesulfonyl acetate. To this a solution of sodium hydroxide (4.88 g in 110 mL of water) is added in portions. The reaction mixture is stirred at room temperature for 3 h. After completion of the reaction (monitored by TLC), the reaction mixture is cooled to 0° C. and conc. HCl is slowly added to bring the solution to pH 3.0–4.0. The precipitated solid is separated and recrystallized from hot water.

Step 4: Preparation of 2,4,6-Trimethoxy styryl-N-(4-methoxy-3-amidophenyl)-Sulfonamide A solution of 3-amido-4-methoxy anilinesulfonylacetic acid (10 mmol) and 2,4,6-trimethoxy benzaldehyde (10 mmol) in glacial acetic acid (15 mL) is stirred at room temperature for 10 min. A catalytic amount of benzylamine (300 microliters) is added to the solution. The solution is then refluxed for 8 h and then the reaction mixture is cooled to room temperature. Ethyl acetate is then added to the reaction mixture and any solid precipitates are separated by filtration. Additional amount (30 mL) of ethyl acetate is added and washed with saturated sodium bicarbonate, dilute HCl and brine. The organic layer is dried over anhydrous sodium sulfate and dried layer is concentrated under vacuum. The solid product obtained is recrystallized from a suitable solvent.

The compounds of the present invention may take the form of salts. The term "salts", embraces salts commonly used to form alkali metal salts and to form addition salts of free acids or free bases. The term "pharmaceutically-acceptable salt" refers to salts which possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid. Examples of pharmaceutically unacceptable acid addition salts include perchlorates and tetrafluoroborates.

Suitable pharmaceutically acceptable base addition salts of compounds of formula I include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. Examples of pharmaceutically unacceptable salts include lithium salts and cyanate salts. All of these salts may be prepared by conventional means from the corresponding compound of formula I by reacting, for example, the appropriate acid or base with the compound of formula I.

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of formula I which are biologically active in the treatment of cancer or other proliferative disease states.

The compounds of the invention may be administered to individuals (mammals, including animals and humans) afflicted with cancer.

The compounds are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

For treating proliferative disorders, the specific dose of compound according to the invention to obtain therapeutic benefit will, of course, be determined by the particular circumstances of the individual patient including, the size, weight, age and sex of the % patient, the nature and stage of the disease, the aggressiveness of the disease, and the route of administration. For example, a daily dosage of from about 0.05 to about 50 mg/kg/day may be utilized. Higher or lower doses are also contemplated.

The amino-substituted sulfonanilide compounds may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical, subcutaneous or sublingual administration. Also contemplated within the scope of the invention is the instillation of drug in the body of the patient in a controlled formulation, with systemic or local release of the drug to occur at a later time. For anticancer use, the drug may be localized in a depot for controlled release to the circulation, or local site of tumor growth.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Phamaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The practice of the invention is illustrated by the following non-limiting examples. Representative compounds are listed in Table 4.

EXAMPLE 1

(E)-2,4,6-Trimethoxystyryl-N-[(3-N,N-dimethylacetamido)-4-methoxyphenyl]sulfonamide A solution of N,N-dimethylglycyl chloride (10 mmol) and (E)-2,4,6-trimethoxystyryl-N-[(3-aminosubstituted)-4-methoxyphenyl]sulfonamide was reacted according to the General Method A. The product obtained was purified by column chromatography. (yield 94.65%, m.p. 176–178° C.)

EXAMPLE 2

(E)-2,4,6-Trimethoxystyryl-N-[(3-acetamido)$_4$-methoxyphenyl]-sulfonamide

A solution of acetyl chloride (10 mmol) and (E)-2,4,6-trimethoxystyryl-N-[(3-aminosubstituted)-4-methoxyphenyl]sulfonamide was reacted according to the General Method A. The product obtained was purified by column chromatography. (yield 64.5%, m.p. 296–298° C.)

EXAMPLE 3

(E)-2,4,6-Trimethoxystyryl-N-[(3-amino)-4-methoxyphenyl]-sulfonamide-L-lysineamide hydrochloride A. (E)-2,4,6-Trimethoxystyryl-N-[(3-amino)-4-methoxyphenyl]sulfonamide-L-di-boc-lysineamide A solution of (E)-2,4,6-trimethoxystyryl-N-[(3-amino)-4-methoxyphenyl]-sulfonamide (1 mmol), di-boc-lysine (1.5 mmol), hydroxybenzotriazole (HOBT)(1.5 mmol) and 1,3-diisopropylcarbodiimide (DIC) (1.5 mmol) in dimethylformamide (DMF)(8 mL) was shaken in a reaction vessel at room temperature for 5 hours. Ethyl acetate (20 mL) was added to the mixture and any precipitated solid was removed by filtration. The volatiles were removed under vacuum and the resulting residue was triturated with ethanol (20 mL) to give (E)-2,4,6-trimethoxystyryl-N-[(3-amino)-4-methoxyphenyl]sulfonamide-L-di-boc-lysineamide.

B. (E)-2,4,6-Trimethoxystyryl-N-[(3-amino)-4-methoxyphenyl]sulfonamide-L-lysineamide hydrochloride To a solution of (E)-2,4,6-trimethoxystyryl-N-[(3-amino)-4-methoxyphenyl]sulfonamide-L-di-boc-lysineamide (500 mg) in dichloromethane (5 ml) was added a solution of 4M HCl/dioxane (1 mL). The resulting mixture was stirred at room temperature for 2 hours. The precipitated salt was separated by filtration and recrystallized from acetone to give (E)-2,4,6-trimethoxystyryl-N-[(3-amino)-4-methoxyphenyl]sulfonamide-L-lysineamide hydrochloride. (yield 44.8%, m.p. above 300° C.).

EXAMPLE 4

(E)-2,4,6-Trimethoxystyryl-N-[(3-acetoxyacetamido)-4-methoxy-phenyl]sulfonamide

A solution of acetoxy acetyl chloride (10 mmol) and (E)-2,4,6-trimethoxystyryl-N-[(3-aminosubstituted)-4-methoxyphenyl]sulfonamide was reacted according to the General Method A. The product obtained was purified by column chromatography. (yield 64.5%, m.p. 219–222° C.)

EXAMPLE 5

(E)-2,4,6-Trimethoxystyryl-N-[(3-carboxymethylamino)-4-methoxyphenyl]sulfonamide To a stirred solution of methyl bromoacetate (5 mmol) and sodium acetate (5 mmol) in methanol (20 mL) was added (E)-2,4,6-trimethoxystyryl-N-[(3-aminosubstituted)-4-methoxyphenyl]sulfonamide (1 mmol). The resulting mixture was heated to reflux for 12–15 h. The reaction mixture was then cooled and poured onto water ice. A solid precipitate formed and was separated by filtration. The product ester was obtained in 85% yield.

The ester (1 g) was dissolved in a mixture of ethanol (8 mL) and 4% aqueous sodium hydroxide (50 mL). The resulting mixture was heated to reflux for 10 min to form a clear solution. The reaction mixture was then allowed to cool to room temperature and stirred at room temperature for 3 hours. Concentrated hydrochloric acid was then added dropwise until a solid precipitate formed. The precipitate was separated by filtration, washed with water and recrystallized from acetone:water to give (E)-2,4,6-trimethoxystyryl-N-[(3-carboxymethylamino)-4-methoxyphenyl]sulfonamide in 58.7% yield. (m.p. 166–170° C.)

EXAMPLE 6

(E)-2,4,6-Trimethoxystyryl-N-[(3-hydroxyacetamido)-4-methoxy-phenyl]sulfonamide

A solution of (E2,4,6-trimethoxystyryl-N-[(3-acetoxyacetamido)-4-methoxyphenyl]sulfonamide (prepared as in Example 4) was hydrolyzed in aqueous potassium carbonate to give (E)-2,4,6-trimethoxystyryl-N-[(3-hydroxyacetamido)-4-methoxyphenyl]sulfonamide. (yield 33.6%, m.p. 182–184° C.)

EXAMPLE 7

(E)-2,4,6-Trimethoxystyryl-N-[(3-chloroacetamido)-4-methoxyphenyl]-sulfonamide

A solution of chloroacetyl chloride (10 mmol) and (E)-2,4,6-trimethoxystyryl-N-[(3-aminosubstituted)-4-methoxyphenyl]sulfonamide was reacted according to the General Method A. The product obtained was purified by column chromatography. (yield 68.7%, m.p. 192–194° C.

EXAMPLE 8

(E)-2,4,6-Trimethoxystyryl-N-[3-(4-methylpiperazinyl)-acetamido-4-methoxyphenyl]sulfonamide A solution of (E)-2,4,6-trimethoxystyryl-N-[(3-chloroacetamido)-4-methoxyphenyl]sulfonamide (10 mmol), N-methylpiperazine (10 mmol) and potassium carbonate (10 mmol) in DMF (20 mL) was heated to reflux (80° C.) for 5 hours. The reaction mixture was then cooled to room temperature, and water was added. The resulting mixture was extracted with ethylacetate. The organic layer was washed with water and brine and dried over sodium sulfate. The volatiles were removed under vacuum to give (E)-2,4,6-trimethoxystyryl-N-[3-(4-methylpiperazinyl)-acetamido-4-methoxyphenyl]sulfonamide in 44.8% yield. (m.p. 137–140° C.)

EXAMPLE 9

(E)-2,4,6-Trimethoxystyryl-N-[(3-trifluoroacetamido)-4-methoxy-phenyl]sulfonamide A solution of trifluoroacetic anhydride (30 mmol) and (E)-2,4,6-trimethoxystyryl-N-[(3-aminosubstituted)-4-methoxyphenyl]sulfonamide (10 mmol) was stirred at room temperature for 2 hours. The volatiles were removed under vacuum and the resulting residue and the product obtained was purified by column chromatography. (yield 58.60%).

EXAMPLE 10

(E)-2,4,6-Trimethoxystyryl-N-[(3-carboxymethylsulfamyl)-4-methoxyphenyl]sulfonamide A solution of methyl chlorosulfonyl acetate (10 mmol) and 5-nitro-2-methoxyaniline is subjected to General Method B and the product obtained is hydrolyzed with aqueous sodium hydroxide to give the title compound.

EXAMPLE 11

(E)-2,4,6-Trimethoxystyryl-N-[(3-carboxyacetamido)-4-methoxy-phenyl]sulfonamide

A solution of methyl 3-chloro-3-oxopropionate (10 mmol) and 5-nitro-2-methoxyaniline is subjected to General Method B and the product obtained is hydrolyzed with aqueous sodium hydroxide to give the title compound.

EXAMPLE 12

(E)-2,4,6-Trimethoxystyryl-N-[(3-guanidino)-4-methoxyphenyl]-sulfonamide

To a solution of 2,4,6-trimethoxystyryl-N-[(3-amino)-4-methoxyphenyl]-sulfonamide (10 mmol), N,N-bis(tert-butoxycarbonyl)thiourea (12 mmol) and triethylamine (22 mmol) in dichloromethane (10 mL), is added Mukaiyama reagent (2-chloro-1-methylpyridinium iodide) (12 mmol). The reaction mixture is stirred at 25° C. until the completion of the reaction which is monitored by TLC. Upon the completion of the reaction, the solvent is evaporated and the residue is dissolved in diethyl ether (15 mL) and washed with water. The ethereal layer is dried over anhydrous sodium sulfate and evaporated in a rotary evaporator to give 2,4,6-trimethoxystyryl-N-[(3-di-tert-butoxyguanidino)-4-methoxyphenyl]-sulfonamide.

A solution of 2,4,6-trimethoxystyryl-N-(3-di-tert-butoxyguanidino-4-methoxyphenyl)sulfonamide (1 g) is dissolved in a 1:1 mixture of dichloromethane and trifluoroacetic acid. The reaction mixture is stirred for 3 h at room temperature and the solution is concentrated under vacuum. The residue is washed and concentrated several times with diethyl ether for complete removal of trifluoroacetic acid. The residue is given a final wash with water and the solid obtained is subjected to column chromatography (silica gel 70–325 mesh) to yield the title compound.

EXAMPLE 13

(E)-2,4,6-Trimethoxystyryl-N-[3-(3,5-dinitrobenzamido)-4-methoxy-phenyl]sulfonamide A solution of 3,5-dinitrobenzoyl chloride (10 mmol) and 5-nitro-2-methoxyaniline is subjected to General Method B to give the title compound.

EXAMPLE 14

(E)-2,4,6-Trimethoxystyryl-N-[3-(3,5-diaminobenzamido)-4-methoxy-phenyl]sulfonamide A solution of (E)-2,4,6-trimethoxystyryl-N-[3-(3,5-dinitrobenzamido)-4-methoxyphenyl]sulfonamide (Example 5) is reduced by following the sodium hydrosulfite reduction procedure as described in General Method B to give the title compound.

EXAMPLE 15

(E)-2,4,6-Trimethoxystyryl-N-[(3-benzamido)-4-methoxyphenyl]-sulfonamide

A solution of benzoylchloride (10 mmol) and 5-nitro-2-methoxyaniline is subjected to General Method B to give the title compound.

EXAMPLE 16

(E)-2,4,6-Trimethoxystyryl-N-3[(4-nitrobenzamido)-4-methoxy-phenyl]sulfonamide

A solution of 4-nitrobenzoyl chloride (10 mmol) and 5-nitro-2-methoxyaniline is subjected to General Method B to give the title compound.

EXAMPLE 17

(E)-2,4,6-Trimethoxystyryl-N-3[(4-aminobenzamido)-4-methoxy-phenyl]sulfonamide

A solution of (E)-2,4,6-trimethoxystyryl-N-[3-(4-nitrobenzamido)-4-methoxyphenyl]sulfonamide (Example 9) is reduced by following the sodium hydrosulfite reduction procedure as described in General Method B to give the title compound.

EXAMPLE 18

(E)-2,4,6-Trimethoxystyryl-N-3[(4-nitrophenyimino)-4-methoxy-phenyl]sulfonamide

To a solution of (E)-2,4,6-trimethoxystyryl-N-[(3-amino)-4-methoxyphenyl]sulfonamide (10 mmol) in methanol (40 mL) is added 4-nitrobenzaldehyde (10 mmol). The solution is refluxed with vigorous stirring for 5 h. The reaction mixture is cooled, diluted with water and the aqueous mixture is then extracted twice with dichloromethane, and the organic layer is dried over anhydrous magnesium sulfate. The dried organic solution is evaporated and the residue is recrystallized to give the title compound.

EXAMPLE 19

(E)-2,4,6-Trimethoxystyryl-N-[(3-amino)-4-methoxyphenyl]sulfonamide-L-serineamide Step 1: (E)-2,4,6-Trimethoxystyryl-N-[(3-amino)-4-methoxyphenyl]sulfonamide-L-Fmoc-serineamide A solution of (E)-2,4,6-trimethoxystyryl-N-[(3-amino)-4-methoxyphenyl]-sulfonamide (1 mmol), Fmoc-Ser-OH (1.5 mmol), HOBT (1.5 mmol) and DIC (1.5 mmol) in DMF (8 mL) is taken in a reaction vessel. The reaction vessel is connected to a manual shaker and is shaken at room temperature for 5 h. Ethyl acetate (20 mL) is then added to the solution and any precipitated material is removed by filtration. The solution is dried under vacuum and the residue is treated with ethanol (20 mL) to give (E)-2,4,6-trimethoxystyryl-N-[(3-amino)-4-methoxyphenyl]sulfonamide-L-Fmoc-serineamide.

Step 2: (E)-2,4,6-Trimethoxystyryl-N-[(3-amino)-4-methoxyphenyl]sulfonamide-L-serineamide To a stirred solution of (E)-2,4,6-trimethoxystyryl-N-(3-amino-4-methoxyphenyl)sulfonamide-L-Fmoc-serineamide (500 mg) dichloromethane (10 mL), is added piperidine (2 mL) and stirring is continued for 2 h. The solvent is removed under vacuum and the residue is dissolved in dichloromethane and loaded on a silica-gel column. The compound is eluted with 1:1 dichloromethane and ethyl acetate. The solvent is removed under vacuum to give (E)-2,4,6-trimethoxystyryl-N-[(3-amino)-4-methoxyphenyl]sulfonamide-L-serineamide.

EXAMPLE 20

(E)-2,4,6-Trimethoxystyryl-N-[(3-amino)-4-methoxyphenyl]-sulfonamide-D-serineamide Step 1: (E)-2,4,6-Trimethoxystyryl-N-[(3-amino)-4-methoxyphenyl]sulfonamide-D-Fmoc-serineamide A solution of (E)-2,4,6-trimethoxystyryl-N-(3-amino-4-methoxyphenyl) sulfonamide (1 mmol), Fmoc-Ser-OH (1.5 mmol), HOBT (1.5 mmol) and DIC (1.5 mmol) in DMF (8 mL) is taken in a reaction vessel. The reaction vessel is connected to a manual shaker and is shaken at room temperature for 5 h. Ethyl acetate (20 mL) is then added to the solution and any precipitated material is removed by filtration. The solution is dried under vacuum and the residue is treated with ethanol (20 mL) to give (E)-2,4,6-trimethoxystyryl-N-(3-amino-4-methoxyphenyl)sulfonamide-D-Fmoc-serineamide.

Step 2: (E)2,4,6-Trimethoxystyryl-N-[(3-amino)-4-methoxyphenyl]sulfonamide-D-serineamide To a stirred solution of (E)-2,4,6-trimethoxystyryl-N-(3-amino-4-methoxyphenyl)sulfonamide-L-Fmoc-serineamide (500 mg) dichloromethane (10 mL), is added piperidine (2 mL) and stirring is continued for 2 h. The solvent is removed under vacuum and the residue is dissolved in dichloromethane and loaded on a silica-gel column. The compound is eluted with 1:1 dichloromethane and ethyl acetate. The solvent is removed under vacuum to give (E)-2,4,6-trimethoxystyryl-N-(3-amino-4-methoxyphenyl)sulfonamide-D-serineamide.

EXAMPLE 21

(E)-2,4,6-Trimethoxystyryl-N-[(3-ureido)-4-methoxyphenyl]-sulfonamide

To a solution of 2,4,6-trimethoxystyryl-N-(3-amino-4-methoxyphenyl)-sulfonamide (1 mmol) in glacial acetic acid (10 mL) is added an aqueous solution of potassium cyanate (1 mmol in 2 mL of de-ionized water). The reaction mixture is stirred for 3 h at room temperature. The reaction mixture is then poured into de-ionized water (100 mL) and extracted with ethyl acetate for 3 times. The combined organic layer is then washed with sodium bicarbonate to neutralize acetic acid and then with brine. The organic layer is then dried over anhydrous magnesium sulfate and the solvent is removed under vacuum to yield the title compound which is purified by column chromatography.

EXAMPLE 22

(E)-2,4,6-Trimethoxystyryl-N-[(3-N-methylamino)-4-methoxy-phenyl]sulfonamide

To a stirred solution of sodium acetate (5 mmol) and 2,4,6-trimethoxystyryl-N-(3-amino-4-methoxyphenyl)sulfonamide (1 mmol) in methanol (20 mL), is added methyl iodide (1.5 mmol) and stirring is continued under reflux temperature for 12–15 h. The contents of the flask are cooled and poured into the ice water. The white product separated out is filtered, washed with chloroform and dried under vacuum to give (E)-2,4,6-trimethoxystyryl-N-(3-N-methylamino-4-methoxyphenyl)sulfonamide.

EXAMPLE 23

(E)-2,4,6-Trimethoxystyryl-N-[3-(3,5-dinitrobenzenesulfamyl)-4-methoxyphenyl]sulfonamide A solution of 2,4-dinitrobenzenesufonyl chloride (10 mmol) and 5-nitro-2-methoxyaniline is subjected to General Method B to give the title compound.

EXAMPLE 24

(E)-2,4,6-Trimethoxystyryl-N-[3-(3,5-diaminobenzene-sulfamyl)-4-methoxy-phenyl]sulfonamide A solution of (E)-2,4,6-trimethoxystyryl-N-[3-(2,4-dinitrobenzene-sulfamyl)₄-methoxyphenyl]sulfonamide (Example 19) is reduced following the sodium hydrosulfite reduction procedure as described in General Method B to give the title compound.

TABLE 4

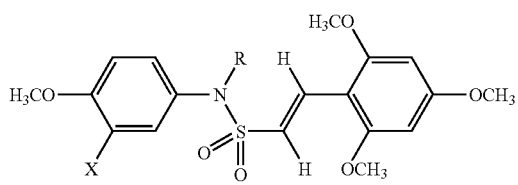

| Example # | X | Synthesis route |
|---|---|---|
| 1 | Dimethylaminoacetamido | A |
| 2 | Acetamido- | A |
| 3 | L-Lysineamido- | A |
| 4 | Acetoxyacetamido | A |
| 5 | Carboxymethylamino | B |
| 6 | Hydroxyacetamido | Hydrolysis of 4 |
| 7 | Chloroacetamido- | A |

TABLE 4-continued

| Example # | X | Synthesis route |
|---|---|---|
| 8 | (4-methylpiperazinyl)-acetamido- | Aminate #7 |
| 9 | trifluoroacetamido | A |
| 10 | Carboxymethylsulfamyl- | B |
| 11 | Carboxyacetamido- | B |
| 12 | Guanidino- | A |
| 13 | 3,5-dinitrobenzamido- | B |
| 14 | 3,5-diaminobenzamido- | Reduce #13 |
| 15 | Benzamido- | B |
| 16 | 4-Nitrobenzamido- | B |
| 17 | 4-Aminobenzamido- | Reduce #16 |
| 18 | 4-nitrophenylimino- | A |
| 19 | L-serinamido- | A |
| 20 | D-serinamido- | A |
| 21 | Ureido- | A |
| 22 | Methylamino- | A |
| 23 | 3,5-dinitrobenzene-sulfamyl- | A |
| 24 | 3,5-diaminobenzene-sulfamyl- | Reduce #23 |

EXAMPLE 25

Effect of Amino-Substituted Sulfonanilides on Tumor Cell Lines

The effect of the amino-substituted sulfonanilides on normal fibroblasts and on tumor cells may be determined by the assay described by Latham et al., *Oncogene* 12:827–837 (1996). Normal diploid lung human fibroblasts (HFL-1) or tumor cells (e.g., prostate, colorectal, breast, glial, pancreatic, ovarian, lung or leukemic) are plated in 6-well dishes at a cell density of $1.0 \times 10^5$ cells per 35-mm² well. The plated cells are treated 24 hours later with various concentrations of amino-substituted sulfonanilide dissolved in dimethyl sulfoxide (DMSO). The total number of viable cells is determined 96 hours later by trypsinizing the wells and counting the number of viable cells, as determined by trypan blue exclusion, using a hemacytometer. Normal HFL cells are treated with the same compounds under the same conditions of concentration and time. Biological data for compounds of the present invention is shown in Table 5 below in DU145, BT20, DLD1 and H157 tumor cell lines. A (+) in the table indicates that the compound showed tumor cell killing activity at a concentration of less than 20 micromolar.

TABLE 5

| Example # | X-R | DU145 | BT20 | DLD1 | H157 |
|---|---|---|---|---|---|
| 1 | 3-NH—COCH₂N(CH₃)₂ | + | + | + | + |
| 2 | 3-NH—COCH₃ | + | + | + | + |
| 3 | 3-NH-L-lysine | + | + | + | + |
| 4 | 3-NH—COCH₂OOCCH₃ | + | + | + | + |
| 5 | 3-NH—CH₂COOH | + | + | + | + |
| 6 | 3-NH—COCH₂OH | + | + | + | + |
| 7 | 3-NH—COCH₂Cl | + | + | + | + |
| 8 | 3-NH—COCH₂-piperazine-N—CH₃ | + | + | + | + |
| 9 | 3-NH—COCF₃ | ND | ND | ND | ND |

EXAMPLE 26

Induction of Apoptosis in Tumor Cells

The following assay demonstrates the apoptotic activity of the compounds of the invention against tumor cells.

The caspases and the ICE-family proteases are cysteine proteases which are activated during apoptosis (Patel et al., FASEB 10:587–597, 1996). The cleavage of poly(ADP-ribose) polymerase (PARP), which is a target of caspase-3, apopain, and several other activated proteases, is a widely used and accepted marker for apoptosis Nicholson et al., Nature 376(6533):37–43, 1995; Lippke et al., *J. Biol. Chemistry* 271:1825, 1996). For this assay, BT20 cells (an estrogen receptor negative breast carcinoma) and HFL-1 cells (normal lung fibroblasts) are treated with an amino-substituted sulfonanilide according to the present invention at a final concentration of 20 μM or dimethyl sulfoxide (DMSO) for 96 hours. The cells are then lysed in RIPA buffer and 100 μg of total cellular protein from each sample is resolved on a 10% SDS-polyacrylamide gel. The proteins are then Western blotted onto PROTRAN filter paper (S/S) and the filter is then probed with antibody (Boehringer Mannheim) specific for PARP. This antibody recognizes both the 116 kDa full length PARP and the 83 kDa cleaved product. The assay shows whether the test compound specifically activates caspases in the treated breast carcinoma cell line and not in the normal cell line. The western blot shows whether only the test compound-treated BT20 cells displayed the presence of the 83 kDa PARP cleavage product. The HFL-1 cells, treated in a similar manner as controls, do not cleave full length PARP. BT20 cells treated with DMSO as a control for the same amount of time do not activate the apoptotic pathway. The results will show that the compounds of the invention selectively kill cancer cells by activating the apoptotic pathway as indicated by the activation of the cysteine proteases, a molecular marker for apoptosis. Cells which are not tumorigenic will not undergo apoptosis but may become growth arrested at concentrations significantly higher than the concentration necessary for tumor cell death.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A compound of formula I:

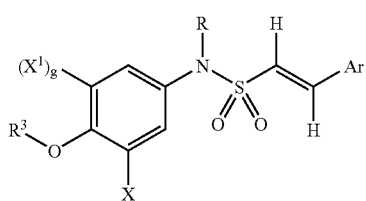

wherein:
Ar is selected from the group consisting of substituted and unsubstituted aryl, and substituted and unsubstituted heteroaryl;
X is selected from the group consisting of (i) and (ii) below:

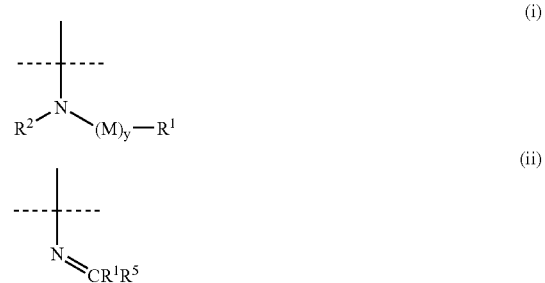

$X^1$ is selected from the group consisting of (i), (ii) and (iii) below:

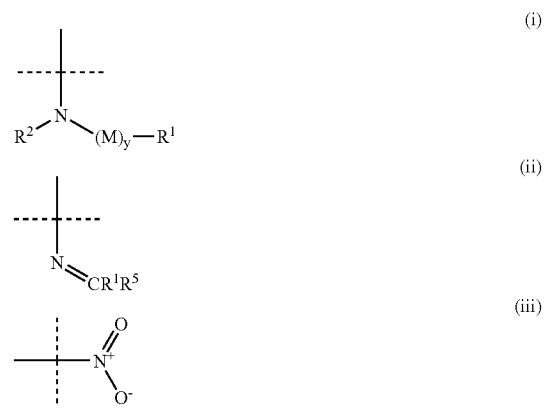

wherein $X^1$ is optionally protected with one or more chemical protecting groups;

g is 0 or 1;

each M is a bivalent connecting group independently selected from the group consisting of —($C_1$–$C_6$)alkylene-, —$(CH_2)_a$—V—$(CH_2)_b$—, —$(CH_2)_d$—W—$(CH_2)_e$— and —Z—;

each y is independently selected from the group consisting of 0 and 1;

each V is independently selected from the group consisting of —C(=O)—, —C(=O)—O—, —C(=O)—(C1–C6)perfluoroalkylene-, —C(=S)—, —S(=O)—, —$SO_2$—, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

—Z— is 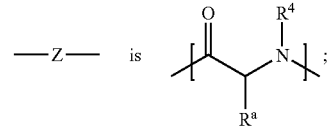;

wherein the absolute stereochemistry of —Z— is D or L, or a mixture of D and L;

R is selected from the group consisting of —H, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heterocyclic, unsubstituted heterocyclic, substituted aryl$(C_1-C_3)$alkyl, unsubstituted aryl$(C_1-C_3)$alkyl, substituted heterocyclic$(C_1-C_3)$alkyl and unsubstituted heterocyclic$(C_1-C_3)$alkyl;

each $R^a$ is independently selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$—(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$—(3-indolyl), —CH$_2$—(4-hydroxyphenyl), —CH(CH$_3$)$_2$ and —CH$_2$—CH$_3$; and includes compounds wherein $R^a$ and $R^1$ combine to form a 5-, 6- or 7-membered heterocyclic ring;

each $R^1$ is independently selected from the group consisting of —H, —(C$_1$-C$_6$)perfluoroalkyl, unsubstituted aryl, substituted aryl, substituted heterocyclic, unsubstituted heterocyclic, —CO$_2$R$^5$, —C(=O)NR$^4_2$, —CR$^4$R$^6$R$^7$, —C(=NH)—NR$^4_2$ and a monovalent peptidyl moiety with a molecular weight of less than 1000; provided that when y is 0 and $R^1$ is —CO$_2$R$^5$, $R^5$ is not —H;

each $R^2$ is independently selected from the group consisting of —H, —(C$_1$-C$_6$)alkyl, and aryl(C$_1$-C$_3$)alkyl, wherein —R$^2$ and —(M)$_y$—R$^1$ may optionally be linked covalently to form a 5-, 6- or 7-membered substituted or unsubstituted heterocycle;

$R^3$ is independently selected from —(C$_1$-C$_6$)alkyl;

each $R^4$ is independently selected from the group consisting of —H, and —(C$_1$-C$_6$)alkyl;

wherein:
when $R^4$ and $R^1$ are bonded to the same nitrogen atom, $R^1$ and $R^4$ may combine to form a heterocycle; and
when two $R^4$ groups are geminally bonded to the same nitrogen, the two $R^4$ groups may combine to form a heterocycle;

each $R^5$ is independently selected from the group consisting of —H, —(C$_1$-C$_6$)alkyl and —(C$_1$-C$_6$)acyl;

each $R^6$ is independently selected from the group consisting of —H, —(C$_1$-C$_6$)alkyl, —CO$_2$R$^5$, —C(=O)R$^7$, —OR$^5$, —SR$^4$, —(C$_1$-C$_3$)alkoxy, —(C$_1$-C$_3$)alkylthio, guanidino, —NR$^4_2$, phenyl, substituted phenyl, heterocyclic, substituted heterocyclic and halogen;

each $R^7$ is independently selected from the group consisting of —H, halogen, —(C$_1$-C$_6$)alkyl, —NR$^4_2$ and heterocycles containing two nitrogen atoms; and wherein the substituents for the substituted aryl and substituted heterocyclic groups comprising or included within Ar, R, $R^1$, $R^a$, $R^6$ and $R^7$, are independently selected from the group consisting of halogen, (C$_1$-C$_6$)alkyl, (C$_1$-C$_6$)alkoxy, —NO$_2$, —C≡N, —CO$_2$R$^5$, —C(=O)O(C$_1$-C$_3$)alkyl, —OH, —(C$_2$-C$_6$)—OH, phosphonato, —NR$^4_2$, —NHC(=O)(C$_1$-C$_6$)alkyl, sulfamyl, carbamyl, —OC(=O)(C$_1$-C$_3$)alkyl, —O(C$_2$-C$_6$)—N((C$_1$-C$_6$)alkyl)$_2$ and —CF$_3$;

provided
(1) when $R^1$ is a monovalent peptidyl moiety of molecular weight less than 1000 and V is —C(=O), —C(=S)—, —S(=O)— or —SO$_2$—, and b is 0;

then said peptidyl moiety is coupled to M through the peptide's amino terminus or through a sidechain amino group to form an amide, thioamide, sulfinamide or sulfonamide respectively;

(2) when $R^1$ is a monovalent peptidyl moiety of molecular weight less than 1000 and V is —C(=O)NR$^3$—, —SO$_2$NR$^3$—, or —NR$^4$—, and b is 0, then said peptidyl moiety is coupled to M through the peptide's carboxy terminus or through a sidechain carboxyl group to form an imide, sulfonimide, or carboxamide respectively; and (3) when $R^1$ is a monovalent peptidyl moiety of molecular weight less than 1000 and W is —S— or —O—, and d is 0, then said peptidyl moiety is coupled to M through the peptide's carboxy terminus or through a sidechain carboxyl group to form a carbothioic acid ester or the carboxylic ester respectively;

or a salt of such a compound.

2. A compound according to claim 1 selected from the group consisting of:

(E)-2,4,6-Trimethoxystyryl-N-[(3-trifluoroacetamido)-4-methoxy-phenyl]sulfonamide; and (E)-2,4,6-Trimethoxystyryl-N-[(3-acetoxyacetamido)4-methoxyphenyl]-sulfonamide;

or a salt of such a compound.

3. A compound according to claim 1 having the formula III:

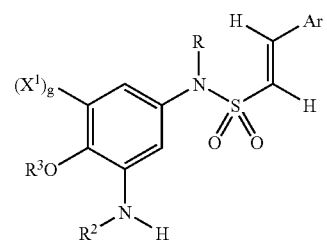

wherein:
Ar, $X^1$, R, $R^2$, $R^3$ and g are defined as in claim 1;
or a salt of such a compound.

4. A compound according to claim 3 having the formula IIIa:

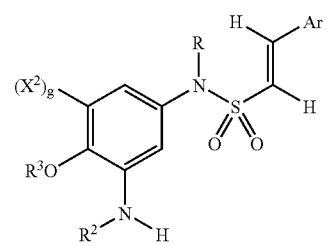

wherein:
Ar, R, $R^2$, $R^3$ and g are defined as in claim 3;
$X^2$ is selected from the group consisting of NO$_2$ and —NH$_2$, optionally protected with a chemical protecting group;
or a salt of such a compound.

5. A compound according to claim 4 wherein Ar is optionally substituted phenyl; or a salt of such a compound.

6. A compound according to claim 1 wherein R is hydrogen or $(C_1-C_6)$alkyl.

7. A compound according to claim 6 wherein Ar is optionally substituted phenyl.

8. A compound according to claim 7 of the formula I':

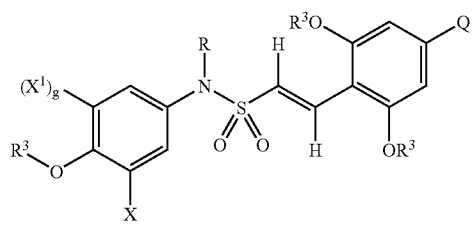

I' wherein:
each $R^3$ is independently selected from —$(C_1-C_6)$alkyl; and
Q is selected from the group consisting of —H, —$(C_1-C_6)$alkoxy, halogen, —$(C_1-C_6)$alkyl and —$NR^4_2$;
or a salt of such a compound.

9. A compound according to claim 4 of formula IIIa':

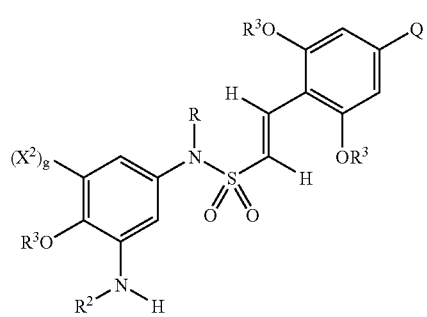

IIIa' wherein:
$X^2$, R, $R^2$ and g are defined as in claim 4;
each $R^3$ is independently selected from —$(C_1-C_6)$alkyl; and
Q is selected from the group consisting of —H, —$(C_1-C_6)$alkoxy, halogen, —$(C_1-C_6)$alkyl and —$NR^4_2$;
or a salt of such a compound.

10. A compound according to claim 9 wherein Q is —$(C_1-C_6)$alkoxy;
or a salt of such a compound.

11. A compound according to claim 10 wherein Q is —$OCH_3$;
or a salt of such a compound.

12. A compound according to claim 11 wherein $R^3$ is —$CH_3$;
or a salt of such a compound.

13. A compound according to claim 12 wherein said compound is (E)-2,4,6-trimethoxystyryl-4-methoxy-3-aminophenylsulfonamide;
or a salt of such a compound.

14. A compound of formula IIa:

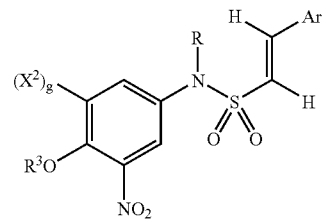

IIa wherein:
Ar is selected from the group consisting of substituted and unsubstituted aryl, and substituted and unsubstituted heteroaryl;
g is 0 or 1;
R is selected from the group consisting of —H, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted heterocyclic, substituted heterocyclic, substituted aryl $(C_1-C_3)$alkyl, unsubstituted aryl$(C_1-C_3)$alkyl, substituted heterocyclic$(C_1-C_3)$alkyl and unsubstituted heterocyclic$(C_1-C_3)$alkyl;
$R^3$ is independently selected from —$(C_1-C_6)$alkyl;
$X^2$ is selected from the group consisting of $NO_2$ and —$NH_2$, optionally protected with a chemical protecting group;
or a salt of such a compound.

15. A compound according to claim 14 which is (E)-2,4,6-trimethoxy-styryl-4-methoxy-3-nitrophenylsulfonamide;
or a salt of such a compound.

16. A compound according to claim 1, wherein:
X is

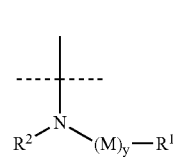

(i)

y is 1;
M is —$(CH_2)_a$—V—$(CH_2)_b$—;
V is —C(=O)—; or a salt of such a compound.

17. A compound according to claim 16, wherein Ar is optionally substituted phenyl.

18. A compound according to claim 17, having the formula IV:

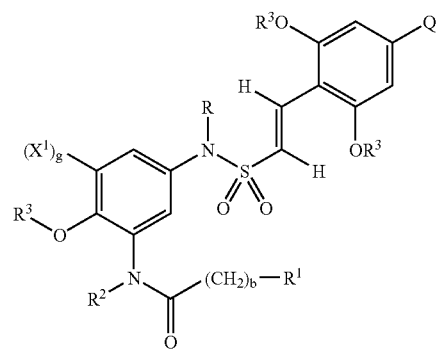

IV wherein:
each $R^3$ is independently selected from —$(C_1–C_6)$alkyl; and

Q is selected from the group consisting of —H, —$(C_1–C_6)$alkoxy, halogen, —$(C_1–C_6)$alkyl and —$NR^4_2$;

or a salt of such a compound.

19. A compound according to claim 18, wherein g is 0; or a salt of such a compound.

20. A compound according to claim 19 selected from the group consisting of:
(E)-2,4,6-trimethoxystyryl-N-[(3-carboxyacetamido)-4-methoxyphenyl]-sulfonamide;
(E)-2,4,6-trimethoxystyryl-N-[3-(3,5,dinitrobenzamido)4-methoxy-phenyl]-sulfonamide;
(E)-2,4,6-trimethoxystyryl-N-[3-(3,5,diaminobenzamido)-4-methoxy-phenyl]-sulfonamide;
(E)-2,4,6-trimethoxystyryl-N-[(3-chloroacetamido)-4-methoxyphenyl]-sulfonamide;
(E)-2,4,6-trimethoxystyryl-N-[3-(4-methylpiperazinyl)acetamido-4-methoxy-phenyl]sulfonamide;
(E)-2,4,6-trimethoxystyryl-N-[(3-benzamido)-4-methoxyphenyl]-sulfonamide;
(E)-2,4,6-trimethoxystyryl-N-3[(4-nitrobenzamido)-4-methoxyphenyl]-sulfonamide;
(E)-2,4,6-trimethoxystyryl-N-3[(4-aminobenzamido)-4-methoxyphenyl]-sulfonamide;
(E)-2,4,6-trimethoxystyryl-N-[(3-acetamido)-4-methoxyphenyl]-sulfonamide;
(E)-2,4,6-trimethoxystyryl-N-[(3-hydroxyacetamido)-4-methoxyphenyl)]-sulfonamide; and
(E)-2,4,6-trimethoxystyryl-N-[(3-N,N-dimethylacetamido)-4-methoxyphenyl]-sulfonamide;
or a salt of such a compound.

21. A compound according to claim 1 wherein:
X is

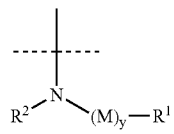

(i)

y is 1; and M is —Z—;
or a salt of such a compound.

22. A compound according to claim 21, wherein Ar is optionally substituted phenyl.

23. A compound according to claim 22, having the formula V:

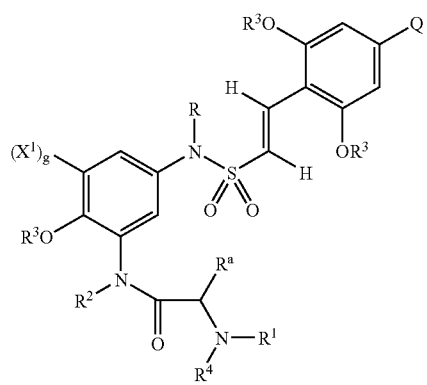

V wherein:
each $R^3$ is independently selected from —$(C_1–C_6)$alkyl; and

Q is selected from the group consisting of —H, —$(C_1–C_6)$alkoxy, halogen, —$(C_1–C_6)$alkyl and —$NR^4_2$;

or a salt of such a compound.

24. A compound according to claim 23, wherein g is 0; or a salt of such a compound.

25. A compound according to claim 24 selected from the group consisting of:
(E)-2,4,6-trimethoxystyryl-N-[(3-amino)4-methoxyphenyl]sulfonamide-L-lysineamide;
(E)-2,4,6-trimethoxystyryl-N-[(3-amino)-4-methoxyphenyl]sulfonamide-L-serineamide;
(E)-2,4,6-trimethoxystyryl-N-[(3-amino)-4-methoxyphenyl]sulfonamide-D-serineamide;
or a salt of such a compound.

26. A compound according to claim 1, wherein:
X is

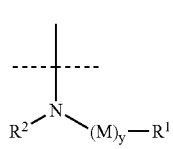

(i)

y is 1; M is —$(CH_2)_a$—V—$(CH_2)_b$—; and V is —$SO_2$—;
or a salt of such a compound.

27. A compound according to claim 26, wherein Ar is optionally substituted phenyl; or a salt of such a compound.

28. A compound according to claim 27, having the formula VI:

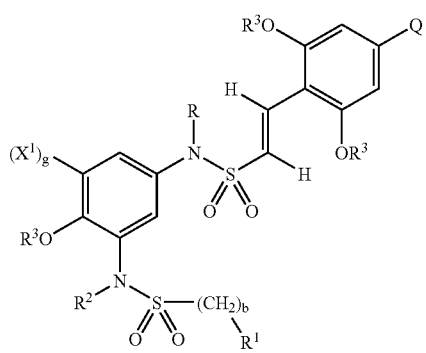

VI wherein:
each $R^3$ is independently selected from —$(C_1–C_6)$alkyl; and

Q is selected from the group consisting of —H, —$(C_1–C_6)$alkoxy, halogen, —$(C_1–C_6)$alkyl and —$NR^4_2$;

or a salt of such a compound.

29. A compound according to claim 28, wherein g is 0; or a salt of such a compound.

30. A compound according to claim 29 selected from the group consisting of:
(E)-2,4,6-trimethoxystyryl-N-[(3-carboxymethylsulfamyl)-4-methoxy-phenyl]sulfonamide;
(E)-2,4,6-trimethoxystyryl-N-[3-(3,5-dinitrobenzenesulfamyl)-4-methoxy-phenyl]sulfonamide;

(E)-2,4,6-trimethoxystyryl-N-[3-(3,5-diaminobenzene-sulfamyl)-4-methoxy-phenyl]sulfonamide;
or a salt of such a compound.

31. A compound according to claim 1 wherein:
X is

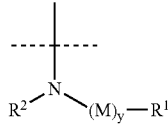
(i)

y is 0;
$R^1$ is —C(=NH)—$NR^3{}_2$;
or a salt of such a compound.

32. A compound according to claim 31 wherein Ar is optionally substituted phenyl; or a salt of such a compound.

33. A compound according to claim 32 having the formula VII:

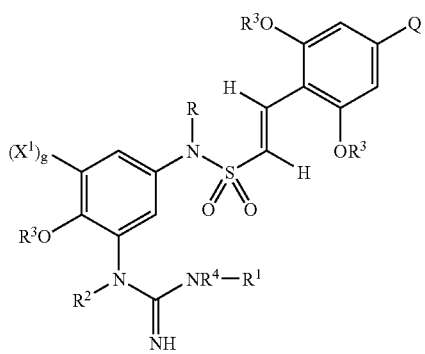
VII wherein:
each $R^3$ is independently selected from —($C_1$–$C_6$)alkyl; and
Q is selected from the group consisting of —H, —($C_1$–$C_6$)alkoxy, halogen, —($C_1$–$C_6$)alkyl and —$NR^4{}_2$;
or a salt of such a compound.

34. A compound according to claim 33, wherein g is 0, or a salt of such a compound.

35. A compound according to claim 34 wherein said compound is (E)-2,4,6-trimethoxystyryl-N-[(3-guanidino)-4-methoxyphenyl]sulfonamide;
or a salt of such a compound.

36. A compound according to claim 1 wherein:
X is

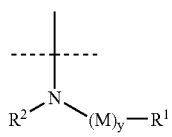
(i)

y is 1; and M is —($C_1$–$C_6$)alkylene-;
or a salt of such a compound.

37. A compound according to claim 36 wherein Ar is optionally substituted phenyl; or a salt of such a compound.

38. A compound according to claim 37 having the formula VIII:

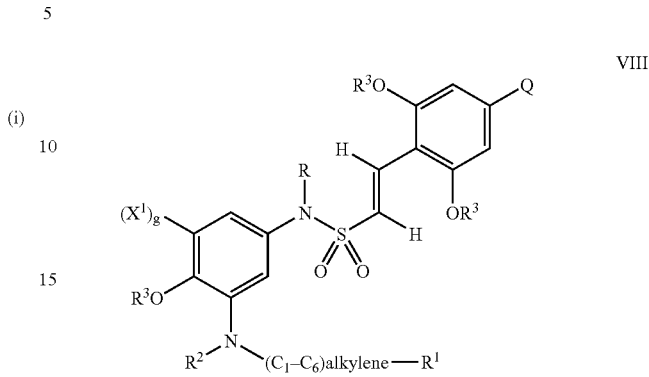
VIII wherein:
each $R^3$ is independently selected from —($C_1$–$C_6$)alkyl; and
Q is selected from the group consisting of —H, —($C_1$–$C_6$)alkoxy, halogen, —($C_1$–$C_6$)alkyl and —$NR^4{}_2$;
or a salt of such a compound.

39. A compound according to claim 38, wherein g is 0; or a salt of such a compound.

40. A compound according to claim 39 selected from the group consisting of:
(E)-2,4,6-trimethoxystyryl-N-[(3-carboxymethylamino) 4-methoxy-phenyl]-sulfonamide;
(E)-2,4,6-trimethoxystyryl-N-[(3-N-methylamino)-4-methoxyphenyl]-sulfonamide;
or a salt of such a compound.

41. A compound according to claim 1 having the formula IX:

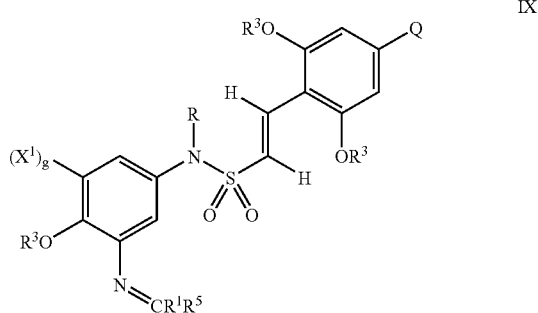
IX wherein:
each $R^3$ is independently selected from —($C_1$–$C_6$)alkyl; and
Q is selected from the group consisting of —H, —($C_1$–$C_6$)alkoxy, halogen, —($C_1$–$C_6$)alkyl and —$NR^4{}_2$;
or a salt of such a compound.

42. A compound according to claim 41, wherein g is 0; or a salt of such a compound.

43. A compound according to claim 42 wherein said compound is (E)-2,4,6-trimethoxystyryl-N-3 [(4-nitrophenylimino)-4-methoxyphenyl]-sulfonamide;
or a salt of such a compound.

44. A compound of formula I according to claim 1 wherein:

X is

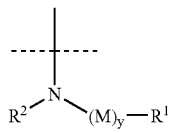

(i)

y is 1; M is —(CH$_2$)$_a$—V—(CH$_2$)$_b$—; and V is —C(=O)NR$^4$—;

or a salt of such a compound.

45. A compound according to claim 44, wherein Ar is optionally substituted phenyl; or a salt of such a compound.

46. A compound according to claim 45 having the formula X:

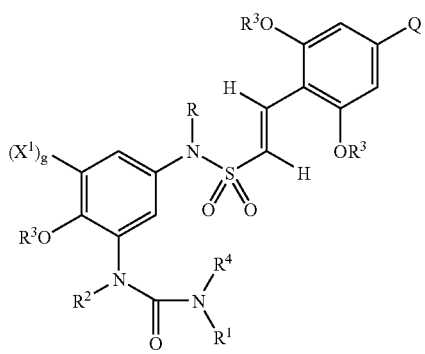

X wherein:
each R$^3$ is independently selected from —(C$_1$–C$_6$)alkyl; and

Q is selected from the group consisting of —H, —(C$_1$–C$_6$)alkoxy, halogen, —(C$_1$–C$_6$)alkyl and —NR$^4$$_2$;

or a salt of such a compound.

47. A compound according to claim 46, wherein g is 0; or a salt of such a compound.

48. A compound according to claim 47 which is (E)-2,4,6-trimethoxystyryl-N-[(3-ureido)-4-methoxyphenyl]sulfonamide, or a salt of such a compound.

49. A process for preparing a compound of claim 1 comprising:
(1) coupling a compound of formula IIIa:

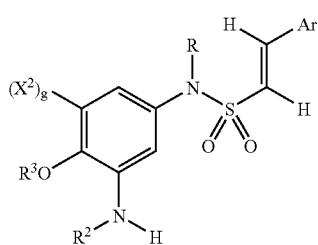

IIIa wherein:
X$^2$ is selected from the group consisting of —NO$_2$ and —NH$_2$, optionally protected with a chemical protecting group;
or a salt of such a compound;
with a compound of formula XI

R$^1$—A       XI wherein:
R$^1$, R$^4$, R$^5$, R$^6$, and R$^7$ are defined as in claim 1; and
A is a moiety containing an electrophilic reactive center, said moiety selected from the group consisting of:
(a) an alkyl moiety having a leaving group;
(b) an aryl halide or aryl pseudo halide;
(c) a carboxylic acid activated with a leaving group;
(d) a sulfonic acid activated with a leaving group;
(e) a carbamic acid moiety activated with a leaving group;
(f) a cyanate moiety;
(g) an aldehyde or ketone moiety, or a hydrate thereof or a ketal or acetal thereof;
(h) a carboxylic acid moiety and an amide coupling reagent; or
(i) the intermediate product of a thiourea moiety and 2-chloro-1-methyl pyridinium iodide;
to form a compound of formula Ia:

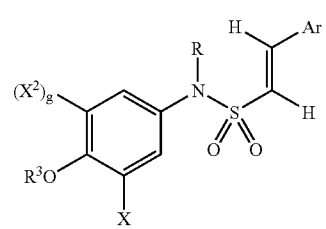

Ia (2) optionally
(a) when —X$^2$ is —NH$_2$ protected with a protecting group, removing said protecting group from —X$^2$ to yield a compound of formula Ib; or
(b) when —X$^2$ is —NO$_2$, chemically reducing said —NO$_2$ to —NH$_2$,
to form a compound of formula Ib:

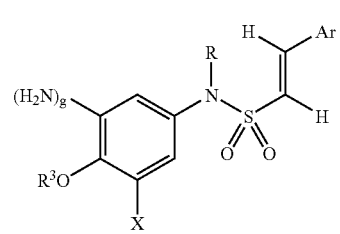

Ib (3) optionally coupling said compound of formula Ib or a salt of such a compound:
with a compound of formula XI:

R$^1$—A       XI wherein one or more functional groups comprising R$^1$ are optionally protected by chemical protecting groups; and wherein A is a moiety containing an electrophilic reactive center as defined above; and (4) optionally removing said protecting groups protecting functionalities on $R^1$ to form a compound of formula I:

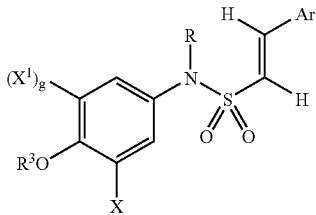

or a salt of such a compound.

50. A process for preparing a compound according to claim 5 of the formula IIIa:

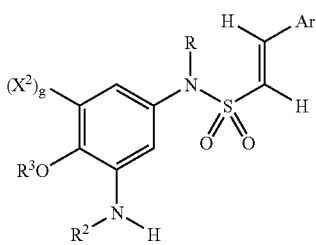

wherein:
Ar is selected from the group consisting of substituted and unsubstituted aryl, and substituted and unsubstituted heteroaryl;
$X^2$ is selected from the group consisting of —$NO_2$ and —$NH_2$, optionally protected with a chemical protecting group
g is 0 or 1;
R is selected from the group consisting of —H, ($C_1$–$C_6$)alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl ($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;
$R^3$ is independently selected from —($C_1$–$C_6$)alkyl;
or a salt of such a compound;
comprising
(1) chemically reducing a compound according to formula IIa:

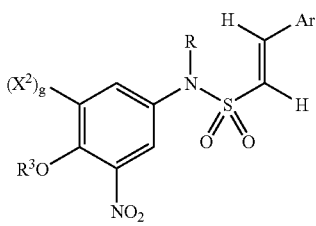

wherein
Ar is selected from the group consisting of substituted and unsubstituted aryl, and substituted and unsubstituted heteroaryl;

$X^2$ is selected from the group consisting of —$NO_2$ and —$NH_2$, optionally protected with a chemical protecting group
g is 0 or 1;
R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl ($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;
$R^3$ is independently selected from —($C_1$–$C_6$)alkyl;
or a salt of such a compound; and
(2) alkylating the aniline reduction product of step 1;
to form a compound of formula IIIa.

51. A process according to claim 50 wherein the compound of formula IIa is prepared by condensing a compound of formula D:

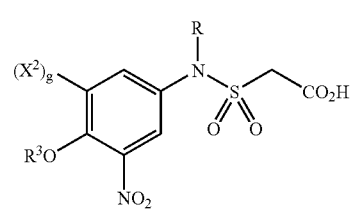

wherein:
R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl ($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;
$R^3$ is independently selected from —($C_1$–$C_6$)alkyl; and
g is 0 or 1; and
$X^2$ is selected from the group consisting of —$NO_2$ and —$NH_2$, optionally protected with a chemical protecting group;
with a compound of formula E:

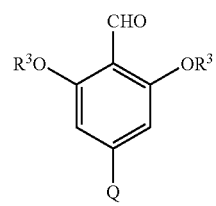

wherein:
each $R^3$ is independently selected from —($C_1$–$C_6$)alkyl; and
each $R^4$ is independently selected from the group consisting of —H, and —($C_1$–$C_6$)alkyl; and
Q is selected from the group consisting of —H, —($C_1$–$C_6$)alkoxy, halogen, —($C_1$–$C_6$)alkyl and —$NR^4_2$; and salts thereof;
to form said compound of formula IIa;
or a salt of such a compound.

52. A process for preparing a compound of claim 1 comprising:

(1) coupling a compound of formula C':

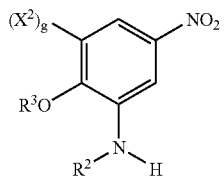

wherein:
$X^2$ is —$NH_2$, optionally protected with a chemical protecting group
g is 0 or 1;
$R^3$ is independently selected from —$(C_1-C_6)$alkyl;
or a salt of such a compound;
with a compound of formula XI $$R^1—A \qquad XI$$

wherein:
$R^1$ is selected from the group consisting of —H, unsubstituted aryl, substituted aryl, substituted heterocyclic, unsubstituted heterocyclic, —$CO_2R^5$, —$C(=O)NR^4_2$, —$CHR^6R^7$, —$C(=NH)$—$NR^4_2$ and a monovalent peptidyl moiety with a molecular weight of less than 1000;
each $R^4$ is independently selected from the group consisting of —H, and —$(C_1-C_6)$alkyl;
each $R^5$ is independently selected from the group consisting of —H, —$(C_1-C_6)$alkyl and —$(C_1-C_6)$acyl;
$R^6$ is selected from the group consisting of —H, —$(C_1-C_6)$alkyl, —$CO_2R^5$, —$C(=O)R^7$, —OH, —$SR^4$, —$(C_1-C_3)$alkoxy, —$(C_1-C_3)$alkylthio, guanidino, —$NR^4_2$, phenyl, substituted phenyl, heterocyclic, substituted heterocyclic and halogen;
$R^7$ is selected from the group consisting of —H, halogen, —$(C_1-C_6)$alkyl, —$NR^4_2$ and heterocycles containing two nitrogen atoms;
wherein the substituents for the substituted aryl and substituted heterocyclic groups comprising or included within $R^1$, $R^6$ and $R^7$, are independently selected from the group consisting of halogen, $(C_1-C_6)$alkyl, $(C_1-C_6)$alkoxy, —$NO_2$, —$C\equiv N$, —$CO_2R^5$, —$C(=O)O(C_1-C_3)$alkyl, —OH, —$(C_2-C_6)$—OH, phosphonato, —$NR^4_2$, —$NHC(=O)(C_1-C_6)$alkyl, sulfamyl, —$OC(=O)(C_1-C_3)$alkyl, —$O(C_2-C_6)$—$N((C_1-C_6)$alkyl$)_2$ and —$CF_3$; and wherein one or more functional groups comprising $R^1$ are optionally protected by chemical protecting groups; and
wherein A is a moiety containing an electrophilic reactive center, said moiety selected from the group consisting of:
(a) an alkyl moiety having a leaving group;
(b) an aryl halide or aryl pseudo halide;
(c) a carboxylic acid activated with a leaving group;
(d) a sulfonic acid activated with a leaving group;
(e) a carbamic acid moiety activated with a leaving group;
(f) a cyanate moiety;
(g) an aldehyde or ketone moiety, or a hydrate thereof or a ketal or acetal thereof;
(h) a carboxylic acid moiety and an amide coupling reagent; or (i) the intermediate product of a thiourea moiety and 2-chloro-1-methyl pyridinium iodide;
to form a compound of formula Ia':

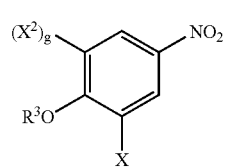

(2) optionally removing said protecting group from —$X^2$ to yield a compound of formula Ib';

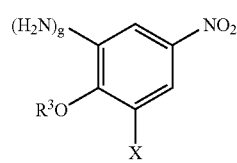

(3) optionally coupling said compound of formula Ib' or a salt of such a compound:
with a compound of formula XI:

$$R^1—A \qquad XI$$

wherein one or more functional groups comprising $R^1$ are optionally protected by chemical protecting groups; and
wherein A is a moiety containing an electrophilic reactive center as defined above;
to form a compound of formula Ic':

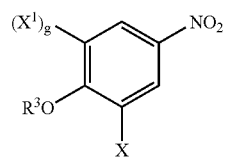

(4) chemically reducing said compound of formula Ic' to give a compound of formula Id':

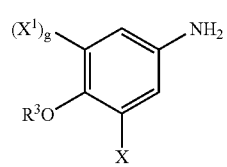

(5) optionally reacting said compound of formula Id' with:
(a) an aldehyde or ketone under reductive amination conditions; or
(b) alkylating the aniline nitrogen of Id' with an alkyl moiety having a leaving group To form a compound of formula Ie':

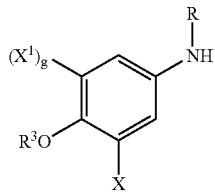

(6) reacting said compound of formula Ie' with an ester of chlorosulfonylacetic acid;

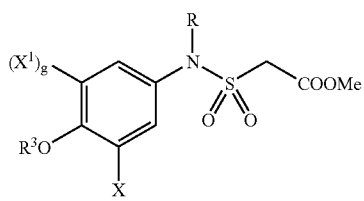

(7) hydrolysing said compound of formula If', to give a compound of formula Ig':

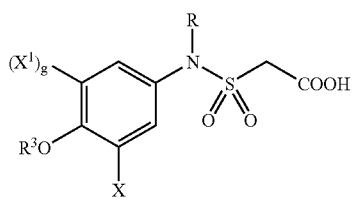

(8) reacting said compound of formula Ig' with an aryl aldehyde, H:

and (9) optionally removing said protecting groups protecting functionalities on $R^1$ to form a compound of formula I:

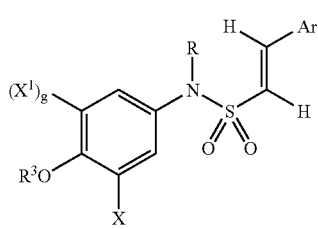

53. A process for producing a compound according to claim 18 having the formula IV, comprising,
(1) coupling a compound of formula IIIa:

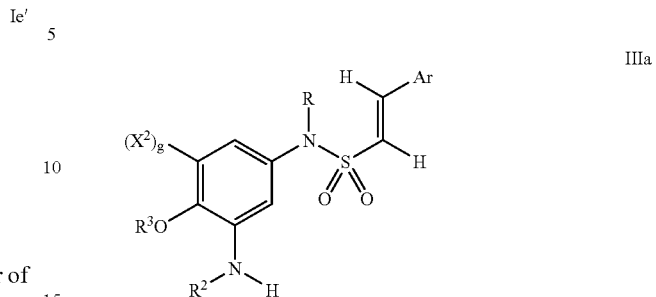

wherein:
Ar is selected from the group consisting of substituted and unsubstituted aryl, and substituted and unsubstituted heteroaryl;
$X^2$ is selected from the group consisting of —$NO_2$ and —$NH_2$, optionally protected with a chemical protecting group
g is 0 or 1;
R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl ($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;
$R^3$ is independently selected from —($C_1$–$C_6$)alkyl;
or a salt of such a compound;
with a compound of formula XII:

$$R^1-A^1 \qquad XII$$

wherein:
$R^1$ is selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000;
each $R^4$ is independently selected from the group consisting of —H, and —($C_1$–$C_6$)alkyl;
each $R^5$ is independently selected from the group consisting of —H, —($C_1$–$C_6$)alkyl and —($C_1$–$C_6$)acyl;
$R^6$ is selected from the group consisting of —H, —($C_1$–$C_6$)alkyl, —$CO_2R^5$, —C(=O)$R^7$, —OH, —$SR^4$, —($C_1$–$C_3$)alkoxy, —($C_1$–$C_3$)alkylthio, guanidino, —$NR^4_2$, phenyl, substituted phenyl, heterocyclic, substituted heterocyclic and halogen;
$R^7$ is selected from the group consisting of —H, halogen, —($C_1$–$C_6$)alkyl, —$NR^4_2$ and heterocycles containing two nitrogen atoms;
wherein the substituents for the substituted aryl and substituted heterocyclic groups comprising or included within $R^1$, $R^6$ and $R^7$, are independently selected from the group consisting of halogen, ($C_1$–$C_6$)alkyl, ($C_1$–$C_6$) alkoxy, —$NO_2$, —C≡N, —$CO_2R^5$, —C(=O)O ($C_1$–$C_3$)alkyl, —OH, —($C_2$–$C_6$)—OH, phosphonato, —$NR^4_2$, —NHC(=O)($C_1$–$C_6$)alkyl, sulfamyl, —OC (=O)($C_1$–$C_3$)alkyl, —O($C_2$–$C_6$)—N(($C_1$–$C_6$)alkyl)$_2$ and —$CF_3$; and wherein one or more functional groups comprising $R^1$ are optionally protected by chemical protecting groups; and $A^1$ is a carboxylic acid moiety containing a leaving group to form a compound of formula IVa:

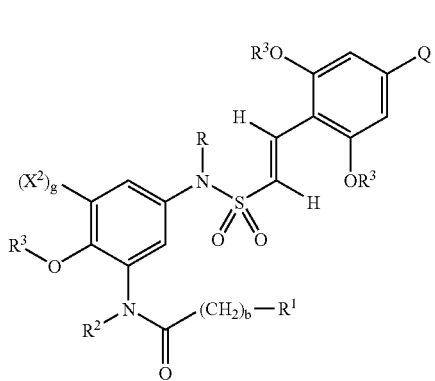

(2) optionally:
   (a) when —$X^2$ is —$NH_2$ protected with a protecting group, removing said protecting group from —$X^2$ to yield a compound of formula IVb; or
   (b) when —$X^2$ is —$NO_2$, chemically reducing said —$NO_2$ to —$NH_2$ to form a compound of formula IVb:

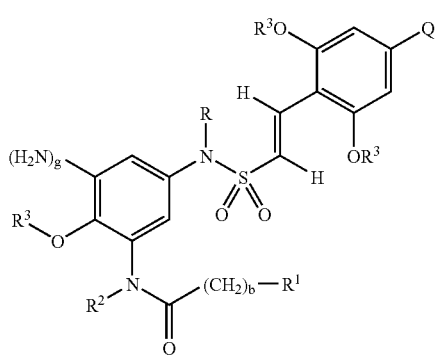

(3) optionally coupling said compound of formula IVb or a salt of such a compound, with a compound of formula XI:

$R^1$—A      XI wherein one or more functional groups comprising $R^1$ are optionally protected by chemical protecting groups; and wherein A is a moiety containing an electrophilic reactive center as defined above; and (4) optionally removing said protecting groups protecting functionalities on $R^1$ to form said compound of formula IV or a salt of such a compound.

54. A process for producing a compound according to claim 23 having the formula V:

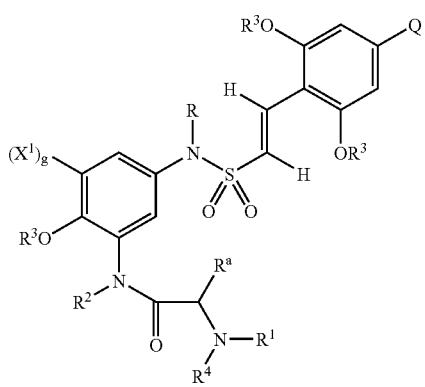

comprising:
(1) reacting a compound of formula IIIa

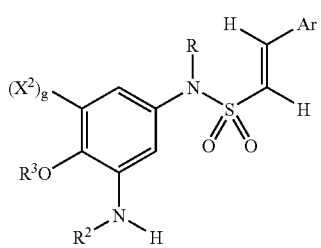

wherein:
Ar is selected from the group consisting of substituted and unsubstituted aryl, and substituted and unsubstituted heteroaryl;

$X^2$ is selected from the group consisting of —$NO_2$ and —$NH_2$, optionally protected with a chemical protecting group g is 0 or 1;

R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl ($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;

$R^3$ is independently selected from —($C_1$–$C_6$)alkyl;

or a salt of such a compound;
with
(a) a compound of formula XIII:

$R^1$—$A^2$      XIII wherein $R^a$ is selected from the group consisting of —H, —$CH_3$, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$—(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —CH₂—OH, —CH(OH)—CH₃, —CH₂-(3-indolyl), —CH₂-(4-hydroxyphenyl), —CH(CH₃)₂ and —CH₂—CH₃; and includes compounds wherein R$^a$ and R$^1$ combine to form a 5-, 6- or 7-membered heterocyclic ring;

R$^1$ is selected from the group consisting of —H, unsubstituted aryl, substituted aryl, substituted heterocyclic, unsubstituted heterocyclic, —CO₂R$^5$, —C(=O)NR$^4$₂, —CHR$^6$R$^7$, —C(=NH)—NR$^4$₂ and a monovalent peptidyl moiety with a molecular weight of less than 1000 and coupled through the peptide's carboxy terminus or through a sidechain carboxyl group to form a carboxamide bond;

each R$^5$ is independently selected from the group consisting of —H, and —(C₁–C₆)alkyl;

R$^1$ is selected from the group consisting of —H, —(C₁–C₆)alkyl and —(C₁–C₆)acyl;

R$^6$ is selected from the group consisting of —H, —(C₁–C₆)alkyl, —CO₂R$^5$, —C(=O)R$^7$, —OH, —SR$^4$, —(C₁–C₃)alkoxy, —(C₁–C₃)alkylthio, guanidino, —NR$^4$₂, phenyl, substituted phenyl, heterocyclic, substituted heterocyclic and halogen;

R$^7$ is selected from the group consisting of —H, halogen, —(C₁–C₆)alkyl, —NR$^4$₂ and heterocycles containing two nitrogen atoms;

wherein the substituents for the substituted aryl and substituted heterocyclic groups comprising or included within R$^1$, R$^a$, R$^6$ and R$^7$, are independently selected from the group consisting of halogen, (C₁–C₆)alkyl, (C₁–C₆)alkoxy, —NO₂, —C≡N, —CO₂R$^5$, —C(=O)O(C₁–C₃)alkyl, —OH, —(C₂–C₆)—OH, phosphonato, —NR$^4$₂, —NHC(=O)(C₁–C₆)alkyl, sulfamyl, —OC(=O)(C₁–C₃)alkyl, —O(C₂–C₆)—N((C₁–C₆)alkyl)₂ and —CF₃; and wherein one or more functional groups comprising R$^1$ are optionally protected by chemical protecting groups; and (b) an amide coupling reagent;

to form a compound of formula Va:

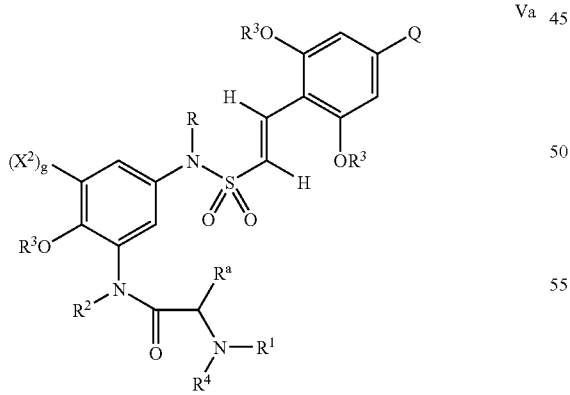

(2) optionally:
(a) when —X$^2$ is —NH₂ protected with a protecting group, removing said protecting group from —X$^2$ to yield a compound of formula Vb; or
(b) when —X$^2$ is —NO₂, chemically reducing said —NO₂ to —NH₂, to form a compound of formula Vb:

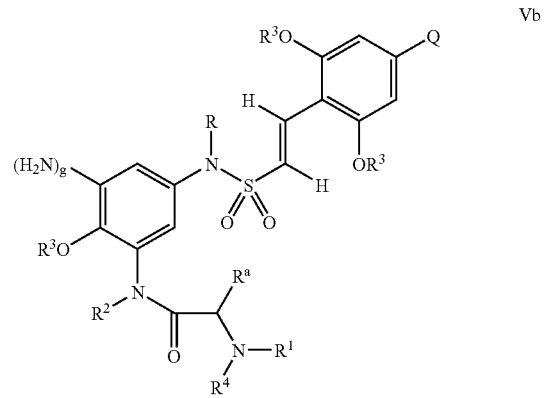

(3) optionally coupling said compound of formula Vb or a salt of such a compound:

with a compound of formula XI:

R$^1$—A    XI wherein one or more functional groups comprising R$^1$ are optionally protected by chemical protecting groups; and wherein A is a moiety containing an electrophilic reactive center as defined above; and (4) optionally removing said protecting groups protecting functionalities on R$^1$ to form said compound of formula V; or a salt of such a compound.

55. A process for producing a compound according to claim 28 having the formula VI:

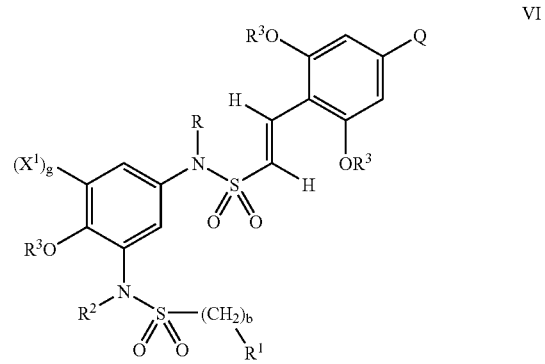

comprising,
(1) coupling a compound of formula IIIa:

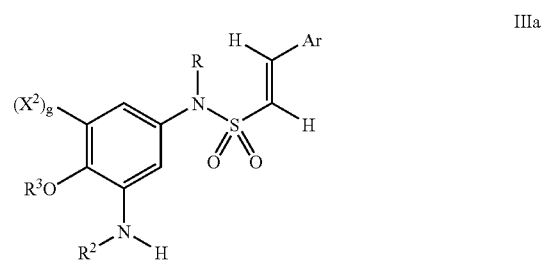

wherein:
Ar is selected from the group consisting of substituted and unsubstituted aryl, and substituted and unsubstituted heteroaryl;

$X^2$ is selected from the group consisting of —$NO_2$ and —$NH_2$, optionally protected with a chemical protecting group g is 0 or 1;

R is selected from the group consisting of —H, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heterocyclic, unsubstituted heterocyclic, substituted aryl $(C_1-C_3)$alkyl, unsubstituted aryl$(C_1-C_3)$alkyl, substituted heterocyclic$(C_1-C_3)$alkyl and unsubstituted heterocyclic$(C_1-C_3)$alkyl;

$R^3$ is independently selected from —$(C_1-C_6)$alkyl;

each $R^4$ is independently selected from the group consisting of —H, and —$(C_1-C_6)$alkyl;

or a salt of such a compound;

with a compound of formula XIV:

$$R^1-A^3 \qquad\qquad XIV$$

wherein:

$R^1$ is selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$ and a monovalent peptidyl moiety with a molecular weight of less than 1000;

each $R^4$ is independently selected from the group consisting of —H, and —$(C_1-C_6)$alkyl;

each $R^5$ is independently selected from the group consisting of —H, $(C_1-C_6)$alkyl and —$(C_1-C_6)$acyl;

$R^6$ is selected from the group consisting of —H, —$(C_1-C_6)$alkyl, —$CO_2R^5$, —C(=O)$R^7$, —OH, —$SR^4$, —$(C_1-C_3)$alkoxy, —$(C_1-C_3)$alkylthio, guanidino, —$NR^4_2$, phenyl substituted phenyl, heterocyclic, substituted heterocyclic and halogen;

$R^7$ is selected from the group consisting of —H, halogen, —$(C_1-C_6)$alkyl, —$NR^4_2$ and heterocycles containing two nitrogen atoms;

wherein the substituents for the substituted aryl and substituted heterocyclic groups comprising or included within $R^1$, $R^6$ and $R^7$, are independently selected from the group consisting of halogen, $(C_1-C_6)$alkyl, $(C_1-C_6)$alkoxy, —$NO_2$, —C≡N, —$CO_2R^5$, —C(=O)O$(C_1-C_3)$alkyl, —OH, —$(C_2-C_6)$—OH, phosphonato, —$NR^4_2$, —NHC(=O)$(C_1-C_6)$alkyl, sulfamyl, —OC(=O)$(C_1-C_3)$alkyl, —O$(C_2-C_6)$—N$((C_1-C_6)$alkyl$)_2$ and —$CF_3$; and wherein one or more functional groups comprising $R^1$ are optionally protected by chemical protecting groups; and $A^3$ is a sulfonyl chloride moiety;

to form a compound of formula VIa:

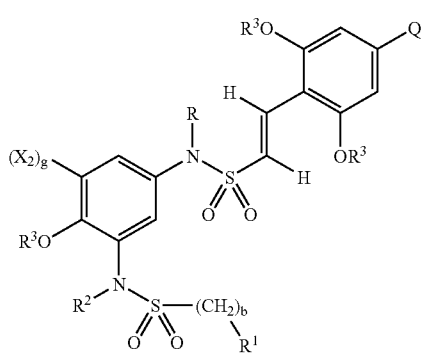

(2) optionally:

(a) when —$X^2$ is —$NH_2$ protected with a protecting group, removing said protecting group from —$X^2$ to yield a compound of formula VIb; or (b) when —$X^2$ is —$NO_2$, chemically reducing said —$NO_2$ to —$NH_2$, to form a compound of formula VIb:

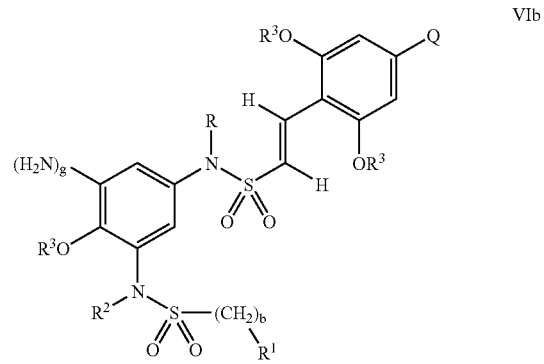

(3) optionally coupling said compound of formula VIb or a salt of such a compound:

with a compound of formula XI:

$$R^1-A \qquad\qquad XI$$

wherein one or more functional groups comprising $R^1$ are optionally protected by chemical protecting groups; and wherein A is a moiety containing an electrophilic reactive center as defined above; and (4) optionally removing said protecting groups protecting functionalities on $R^1$ to form said compound of formula VI.

56. A process for producing a compound according to claim 33 having the formula VII:

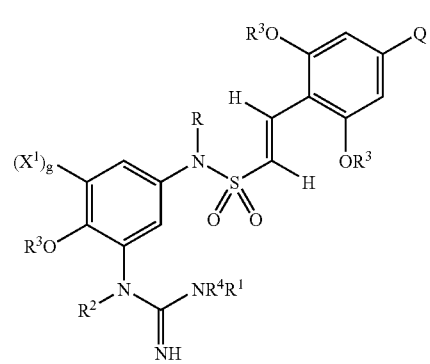

comprising, (1) coupling a compound of formula IIIa:

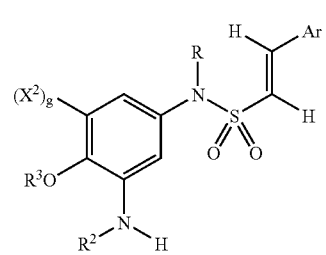

wherein:

Ar is selected from the group consisting of substituted and unsubstituted aryl, and substituted and unsubstituted heteroaryl;

$X^2$ is selected from the group consisting of —$NO_2$ and —$NH_2$, optionally protected with a chemical protecting group.

g is 0 or 1;

R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;

$R^3$ is independently selected from —($C_1$–$C_6$)alkyl;

or a salt of such a compound;

with a compound of formula XV:

$R^1$—$A^4$     XV wherein one or more functional groups comprising $R^1$ are optionally protected by chemical protecting groups; and wherein $A^4$ is moiety which is a reactive intermediate product of a substituted thiourea and 2-chloro-1-methylpyridinium iodide;

to form a compound of formula VIIa:

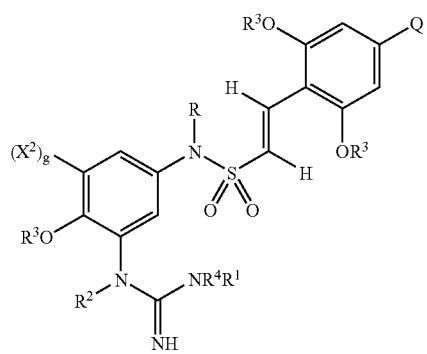

VIIa (2) optionally:
  (a) when —$X^2$ is —$NH_2$ protected with a protecting group, removing said protecting group from —$X^2$ to yield a compound of formula VIIb; or
  (b) when —$X^2$ is —$NO_2$, chemically reducing said —$NO_2$ to —$NH_2$, to form a compound of formula VIIb:

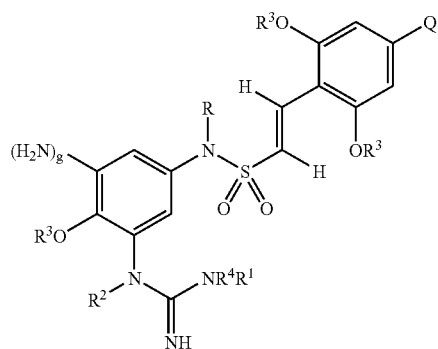

VIIb (3) optionally coupling said compound of formula VIIb or a salt of such a compound:

with a compound of formula XI:

$R^1$—A     XI wherein one or more functional groups comprising $R^1$ are optionally protected by chemical protecting groups; and wherein A is a moiety containing an electrophilic reactive center as defined above; and (4) optionally removing said protecting groups protecting functionalities on $R^1$ to form said compound of formula VII; or a salt of such a compound.

57. A process for producing a compound according to claim 38 having the formula VIII:

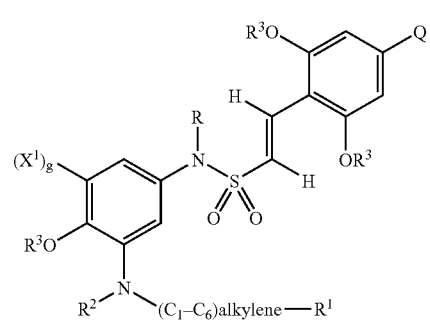

VIII comprising:
(1) coupling a compound of formula IIIa:

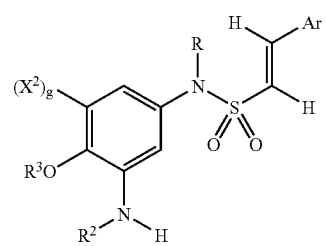

IIIa wherein:
Ar is selected from the group consisting of substituted and unsubstituted aryl, and substituted and unsubstituted heteroaryl;

$X^2$ is selected from the group consisting of —$NO_2$ and —$NH_2$, optionally protected with a chemical protecting group g is 0 or 1;

R is selected from the group consisting of —H, ($C_1$–$C_6$) alkyl, ($C_1$–$C_6$)alkoxy, ($C_3$–$C_6$)alkenyl, ($C_2$–$C_6$)heteroalkyl, ($C_3$–$C_6$)heteroalkenyl, ($C_2$–$C_6$)hydroxyalkyl, substituted aryl, unsubstituted aryl, substituted heterocyclic, unsubstituted heterocyclic, substituted aryl($C_1$–$C_3$)alkyl, unsubstituted aryl($C_1$–$C_3$)alkyl, substituted heterocyclic($C_1$–$C_3$)alkyl and unsubstituted heterocyclic($C_1$–$C_3$)alkyl;

$R^3$ is independently selected from —($C_1$–$C_6$)alkyl;

or a salt of such a compound;

with a compound of formula XVI $R^1$—$A^5$     XVI wherein:
$R^1$ is selected from the group consisting of —H, unsubstituted aryl, substituted aryl, substituted heterocyclic, unsubstituted heterocyclic, —$CO_2R^5$, —C(=O)$NR^4_2$, —CHR⁶R⁷, —C(=NH)—NR⁴₂ and a monovalent peptidyl moiety with a molecular weight of less than 1000;

each R⁴ is independently selected from the group consisting of —H, and —(C₁–C₆)alkyl;

each R⁵ is independently selected from the group consisting of —H, —(C₁–C₆)alkyl and —(C₁–C₆)acyl;

R⁶ is selected from the group consisting of —H, —(C₁–C₆)alkyl, —CO₂R⁵, —C(=O)R⁷, —OH, —SR⁴, —(C₁–C₃)alkoxy, —(C₁–C₃)alkylthio, guanidino, —NR⁴₂, phenyl, substituted phenyl, heterocyclic, substituted heterocyclic and halogen;

R⁷ is selected from the group consisting of —H, halogen, —(C₁–C₆)alkyl, —NR⁴₂ and heterocycles containing two nitrogen atoms;

wherein the substituents for the substituted aryl and substituted heterocyclic groups comprising or included within R¹, R⁶ and R⁷, are independently selected from the group consisting of halogen, (C₁–C₆)alkyl, (C₁–C₆) alkoxy, —NO₂, —C≡N, —CO₂R⁵, —C(=O)O (C₁–C₃)alkyl, —OH, —(C₂–C₆)—OH, phosphonato, —NR⁴₂, —NHC(=O)(C₁–C₆)alkyl, sulfamyl, —OC(=O)(C₁–C₃)alkyl, —O(C₂–C₆)—N((C₁–C₆)alkyl)₂ and —CF₃; and wherein one or more functional groups comprising R¹ are optionally protected by chemical protecting groups; and wherein A⁵ is an alkyl moiety containing a leaving group;

to form a compound of formula VIIa:

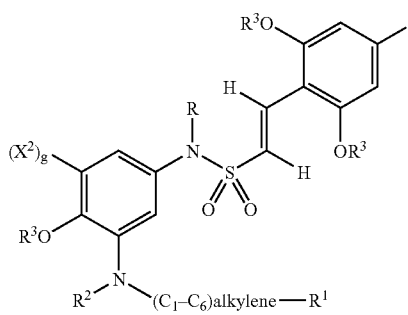

VIIIa (2) optionally:
(a) when —X² is —NH₂ protected with a protecting group, removing said protecting group from —X² to yield a compound of formula VIIIb; or
(b) when —X² is —NO₂, chemically reducing said —NO₂ to —NH₂, to form a compound of formula VIIIb:

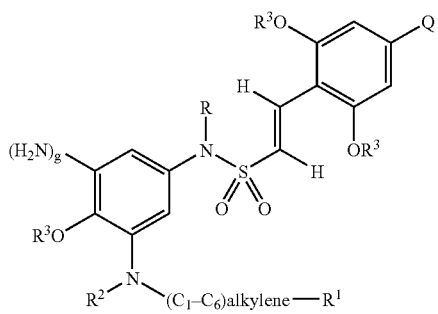

VIIIb (3) optionally coupling said compound of formula VIIIb or a salt of such a compound:

with a compound of formula XI:

R¹—A       XI wherein one or more functional groups comprising R¹ are optionally protected by chemical protecting groups; and wherein A is a moiety containing an electrophilic reactive center as defined above; and (4) optionally removing said protecting groups protecting functionalities on R¹ to form said compound of formula VIII; or a salt of such a compound.

58. A process for producing a compound according to claim 41 having the formula IX:

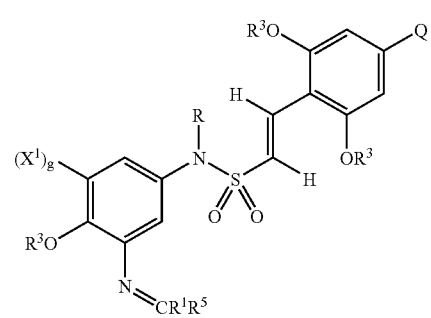

IX comprising;
(1) coupling a compound of formula IIIa:

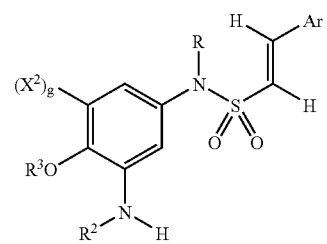

IIIa wherein:
Ar is selected from the group consisting of substituted and unsubstituted aryl, and substituted and unsubstituted heteroaryl;
X² is selected from the group consisting of —NO₂ and —NH₂, optionally protected with a chemical protecting group
g is 0 or 1;
R is selected from the group consisting of —H, (C₁–C₆) alkyl, (C₁–C₆)alkoxy, (C₃–C₆)alkenyl, (C₂–C₆)heteroalkyl, (C₃–C₆)heteroalkenyl, (C₂–C₆)hydroxyalkyl, substituted aryl, unsubstituted aryl, substituted heterocyclic, unsubstituted heterocyclic, substituted aryl (C₁–C₃)alkyl, unsubstituted aryl(C₁–C₃)alkyl, substituted heterocyclic(C₁–C₃)alkyl and unsubstituted heterocyclic(C₁–C₃)alkyl;
R² is —H;
R³ is independently selected from —(C₁–C₆)alkyl;
or a salt of such a compound;
with a compound of formula XVII

R¹—A⁶       XVII wherein:
R¹ is selected from the group consisting of —H, unsubstituted aryl, substituted aryl, substituted heterocyclic, unsubstituted heterocyclic, —CO$_2$R$^5$, —C(═O)NR$^4$$_2$, —CHR$^6$R$^7$, —C(═NH)—NR$^4$$_2$ and a monovalent peptidyl moiety with a molecular weight of less than 1000;

each R$^4$ is independently selected from the group consisting of —H, and —(C$_1$–C$_6$)alkyl;

each R$^5$ is independently selected from the group consisting of —H, —(C$_1$–C$_6$)alkyl and —(C$_1$–C$_6$)acyl;

R$^6$ is selected from the group consisting of —H, —(C$_1$–C$_6$)alkyl, —CO$_2$R$^5$, —C(═O)R$^7$, —OH, —SR$^4$, —(C$_1$–C$_3$)alkoxy, —(C$_1$–C$_3$)alkylthio, guanidino, —NR$^4$$_2$, phenyl, substituted phenyl, heterocyclic, substituted heterocyclic and halogen;

R$^7$ is selected from the group consisting of —H, halogen, —(C$_1$–C$_6$)alkyl, —NR$^4$$_2$ and heterocycles containing two nitrogen atoms;

wherein the substituents for the substituted aryl and substituted heterocyclic groups comprising or included within R$^1$, R$^6$ and R$^7$, are independently selected from the group consisting of halogen, (C$_1$–C$_6$)alkyl, (C$_1$–C$_6$) alkoxy, —NO$_2$, —C≡N, —CO$_2$R$^5$, —C(═O)O (C$_1$–C$_3$)alkyl, —OH, —(C$_2$–C$_6$)—OH, phosphonato, —NR$^4$$_2$, —NHC(═O)(C$_1$–C$_6$)alkyl sulfamyl, —OC (═O)(C$_1$–C$_3$)alkyl, —O(C$_2$–C$_6$)—N((C$_1$–C$_6$)alkyl)$_2$ and —CF$_3$; and wherein one or more functional groups comprising R$^1$ are optionally protected by chemical protecting groups; and wherein A$^6$ comprises an aldehyde or ketone moiety, or a hydrate thereof or a ketal or acetal thereof;

to form a compound of formula IXa:

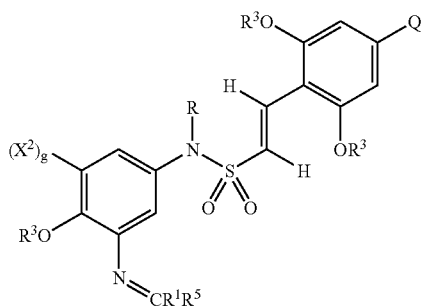

IXa (2) optionally:
(a) when —X$^2$ is —NH$_2$ protected with a protecting group, removing said protecting group from —X$^2$ to yield a compound of formula IXb; or
(b) when —X$^2$ is —NO$_2$, chemically reducing said —NO$_2$ to —NH$_2$,
to form a compound of formula IXb:

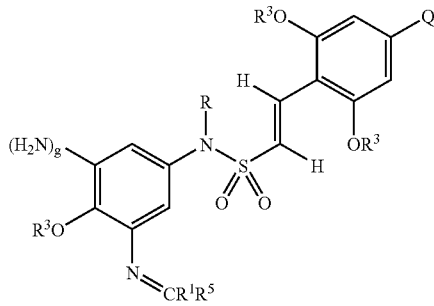

IXb (3) optionally coupling said compound of formula IXb or a salt of such a compound:

with a compound of formula XI:

R$^1$—A    XI wherein one or more functional groups comprising R$^1$ are optionally protected by chemical protecting groups; and wherein A is a moiety containing an electrophilic reactive center as described above; and (4) optionally removing said protecting groups protecting functionalities on R$^1$ to form said compound of formula IX; or a salt of such a compound.

59. A process for producing a compound according to claim 46 having the formula X:

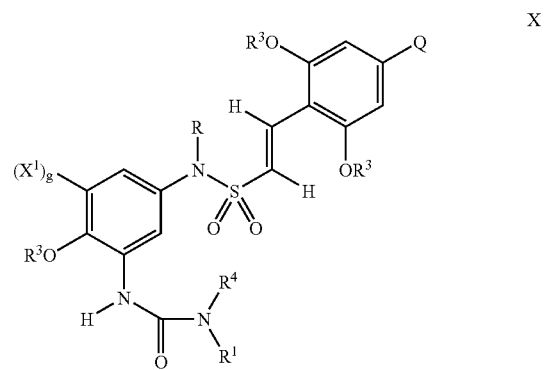

X comprising;

(1) coupling a compound of formula IIIa:

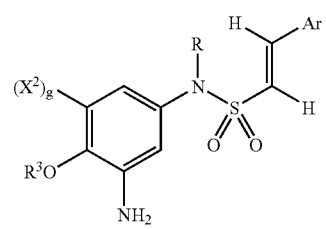

IIIa wherein:

Ar is selected from the group consisting of substituted and unsubstituted aryl, and substituted and unsubstituted heteroaryl;

X$^2$ is selected from the group consisting of —NO$_2$ and —NH$_2$, optionally protected with a chemical protecting group g is 0 or 1;

R is selected from the group consisting of —H, (C$_1$–C$_6$) alkyl, (C$_1$–C$_6$)alkoxy, (C$_3$–C$_6$)alkenyl, (C$_2$–C$_6$)heteroalkyl, (C$_3$–C$_6$)heteroalkenyl, (C$_2$–C$_6$)hydroxyalkyl, substituted aryl, unsubstituted aryl, substituted heterocyclic, unsubstituted heterocyclic, substituted aryl (C$_1$–C$_3$)alkyl, unsubstituted aryl(C$_1$–C$_3$)alkyl, substituted heterocyclic(C$_1$–C$_3$)alkyl and unsubstituted heterocyclic(C$_1$–C$_3$)alkyl;

R$^3$ is independently selected from —(C$_1$–C$_6$)alkyl;

or a salt of such a compound;

with a compound of formula XVIII:

$$R^1-A^7 \quad\quad XVIII$$

wherein:
R¹ is selected from the group consisting of —H, unsubstituted aryl, substituted aryl, substituted heterocyclic, unsubstituted heterocyclic, —CO₂R⁵, —C(=O)NR⁴₂, —CHR⁶R⁷, —C(=NH)—NR⁴₂ and a monovalent peptidyl moiety with a molecular weight of less than 1000;

each R⁴ is independently selected from the group consisting of —H, and —(C₁–C₆)alkyl;

each R⁵ is independently selected from the group consisting of —H, —(C₁–C₆)alkyl and —(C₁–C₆)acyl;

R⁶ is selected from the group consisting of —H, —(C₁–C₆)alkyl, —CO₂R⁵, —C(=O)R⁷, —OH, —SR⁴, —(C₁–C₃)alkoxy, —(C₁–C₃)alkylthio, guanidino, —NR⁴₂, phenyl, substituted phenyl, heterocyclic, substituted heterocyclic and halogen;

R⁷ is selected from the group consisting of —H, halogen, —(C₁–C₆)alkyl, —NR⁴₂ and heterocycles containing two nitrogen atoms;

wherein the substituents for the substituted aryl and substituted heterocyclic groups comprising or included within R¹, R⁶ and R⁷, are independently selected from the group consisting of halogen, (C₁–C₆)alkyl, (C₁–C₆) alkoxy, —NO₂, —C≡N, —CO₂R⁵, —C(=O)O (C₁–C₃)alkyl, —OH, —(C₂–C₆)—OH, phosphonato, —NR⁴₂, —NHC(=O)(C₁–C₆)alkyl, sulfamyl, —OC (=O)(C₁–C₃)alkyl, —O(C₂–C₆)—N((C₁–C₆)alkyl)₂ and —CF₃; and wherein one or more functional groups comprising R¹ are optionally protected by chemical protecting groups; and wherein:
(a) if A⁷ is a cyanate moiety, then R¹ is selected from the group consisting of —H, (C₁–C₆)alkyl and aryl; and R⁴ is —H; and
(b) if A⁷ is a carbamic acid moiety activated with a leaving group, then R¹ and R⁴ of formula X are as defined above;

to form a compound of formula Xa:

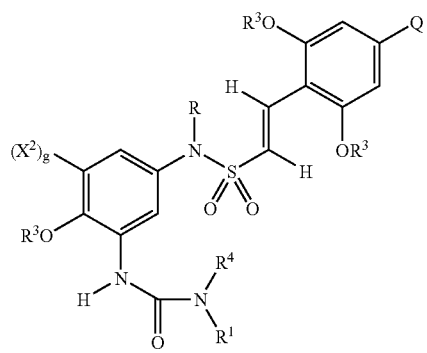

(2) optionally:
(a) when —X² is —NH₂ protected with a protecting group, removing said protecting group from —X² to yield a compound of formula Xb; or
(b) when —X² is —NO₂, chemically reducing said —NO₂ to —NH₂;

to form a compound of formula Xb:

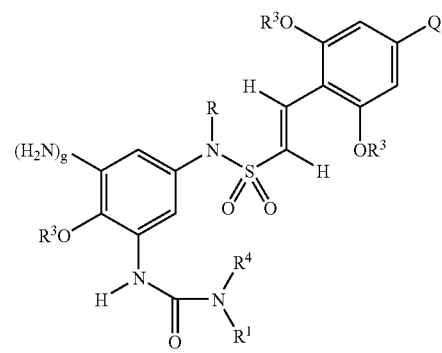

(3) optionally coupling said compound of formula Xb or a salt of such a compound:
with a compound of formula XI:

$$R^1-A \quad\quad XI$$

wherein one or more functional groups comprising R¹ are optionally protected by chemical protecting groups; and wherein A is a moiety containing an electrophilic reactive center as described above; and (4) optionally removing said protecting groups protecting functionalities on R¹ to form said compound of formula X; or a salt of such a compound.

60. A conjugate of the formula, I-L-Ab;
wherein
I is a compound according to claim 1;
Ab is an antibody; and
—L— is a single covalent bond or a linking group covalently linking said compound to said antibody.

61. A conjugate according to claim 60 wherein said antibody Ab is a monoclonal antibody or a monospecific polyclonal antibody.

62. A conjugate according to claim 61 wherein said antibody Ab is a tumor-specific antibody.

63. A conjugate of the formula, III-L-Ab;
wherein
III is a compound according to claim 2;
Ab is an antibody; and
—L— is a single covalent bond or a linking group covalently linking said compound to said antibody.

64. A conjugate according to claim 63 wherein said antibody Ab is a monoclonal antibody or a monospecific polyclonal antibody.

65. A conjugate according to claim 64 wherein said antibody Ab is a tumor-specific antibody.

66. A conjugate of the formula, I'-L-Ab;
wherein
I' is a compound according to claim 7;
Ab is an antibody; and
—L— is a single covalent bond or a linking group covalently linking said compound to said antibody.

67. A conjugate according to claim 66 wherein said antibody Ab is a monoclonal antibody or a monospecific polyclonal antibody.

68. A conjugate according to claim 67 wherein said antibody Ab is a tumor-specific antibody.

69. A pharmaceutical composition comprising a pharmaceutically acceptable carrier and at least one compound according to claim 1, or a pharmaceutically acceptable salt of such a compound.

70. A pharmaceutical composition comprising a pharmaceutically acceptable carrier and at least one conjugate according to claim 60, 63 or 66.

71. A method of treating an individual for a proliferative disorder comprising administering to said individual an effective amount of at least one compound according to claim 1, or a pharmaceutically acceptable salt of such a compound.

72. A method according to claim 71 wherein the proliferative disorder is selected from the group consisting of hemangiomatosis in newborn; secondary progressive multiple sclerosis; chronic progressive myelodegenerative disease; neurofibromatosis; ganglioneuromatosis; keloid formation; Paget's Disease of the bone; fibrocystic disease, sarcoidosis; Peronies and Duputren's fibrosis, cirrhosis, atherosclerosis and vascular restenosis.

73. A method according to claim 71 wherein the proliferative disorder is cancer.

74. A method of according to claim 73 wherein the cancer is selected from the group of cancers of the ovaries, testis, cervix, uterus, vagina, breast, prostate, lung, kidney, rectum, colon, stomach adrenal gland, mouth esophagus, brain, liver, gall bladder, skin, bone, lymphatic system and eye, or the cancer is a hematological neoplasia.

75. A method of inducing apoptosis of tumor cells in an individual afflicted with cancer comprising administering to said individual an effective amount of at least one compound according to claim 1, or a pharmaceutically acceptable salt of such a compound.

76. A method according to claim 75 wherein the tumor cells are selected from the group of tumors consisting of tumors of the ovaries, testis, cervix, uterus, vagina, breast, prostate, lung, kidney, rectum, colon, stomach adrenal gland, mouth esophagus, brain, liver, gall bladder, skin, bone, lymphatic system and eye.

77. A method of treating an individual afflicted with cancer, comprising administering to said individual an effective amount of at least one conjugate according to claim 60, 63 or 66.

* * * * *

UNITED STATES PATENT AND TRADEMARK OFFICE
CERTIFICATE OF CORRECTION

PATENT NO. : 7,161,031 B2
APPLICATION NO. : 10/505998
DATED : January 9, 2007
INVENTOR(S) : Reddy et al.

It is certified that error appears in the above-identified patent and that said Letters Patent is hereby corrected as shown below:

IN THE SPECIFICATION column 1 line 61: "antineoplasitc" should read --antineoplastic--
column 4 line 19: "-($C_2$-$C_6$)-OH" should read -- -($C_2$-$C_6$)alkylene-OH --
column 4 line 21: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 7 line 6: "-($C_2$-$C_6$)-OH" should read -- -($C_2$-$C_6$)alkylene-OH --
column 7 line 8: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 10 line 16: "-($C_2$-$C_6$)-OH" should read -- -($C_2$-$C_6$)alkylene-OH --
column 10 line 18: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 18 line 53: "-($C_2$-$C_6$)-OH" should read -- -($C_2$-$C_6$)alkylene-OH --
column 18 line 55: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 19 line 13: "Iia" should read --IIa--.
column 20 line 28: delete the expression "or a salt of such a compound"
column 20 line 61: "compound." should read --compound;--
column 21 line 11: "moety" should read --moiety--
column 21 line 26: "Mukaima's reagent" should read --Mukaiyama's reagent--
column 22 line 19: "compounds compounds" should read --compounds--
column 22 line 23: "electrophylic" should read --electrophilic--
column 22 line 44: "incompatable" should read --incompatible--
column 25 line 59: "-($C_2$-$C_6$)-OH" should read -- -($C_2$-$C_6$)alkylene-OH --
column 25 line 61: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 26 line 6: "moety" should read --moiety--
column 26 line 22: "Mukaima's reagent" should read --Mukaiyama's reagent--
column 30 line 55: "formula IVb" should read --formula Vb--
column 33 line 6: "$A^4$ is moiety" should read --$A^4$ is a moiety--
column 41 line 53: "(4n + 2)" should read --((4n + 2)--
column 42 line 31: "traizolyl" should read --triazolyl--
column 44 line 30: " Pagets Disease" should read --Paget's disease--
column 44 line 31: "Peronies and Duputren's fibrosis" should read --Peyronie's fibrosis, Dupuytren's fibrosis--
column 44 line 37: "Mathod" should read --Method--
column 46 line 59: " diethylether" should read --diethyl ether--
column 47 line 18: " ethylacetate" should read -- ethyl acetate--
column 47 line 51: "HCL" should read --HCl--
column 47 line 64: "porion" should read --portion--

UNITED STATES PATENT AND TRADEMARK OFFICE
CERTIFICATE OF CORRECTION

PATENT NO. : 7,161,031 B2
APPLICATION NO. : 10/505998
DATED : January 9, 2007
INVENTOR(S) : Reddy et al.

It is certified that error appears in the above-identified patent and that said Letters Patent is hereby corrected as shown below:

IN THE SPECIFICATION (cont'd)

column 47 line 64: "misture" should read --mixture--
column 47 line 65: "prgress" should read --progress--
column 48 line 12: "sodiumdithionite" should read -- sodium dithionite--
column 48 line 43: "alphatic" should read --aliphatic--
column 48 line 51: " sepatated" should read --separated--
column 48 line 55: replace "sstrategy" with --strategy--
column 48 line 65: " deriviatization" should read -- derivatization--
column 49 line 65: "alphatic" should read --aliphatic--
column 52 line 12: delete the expression "salicyclic, salicyclic,"
column 52 line 16: "algenic" should read --alginic--
column 52 line 17: "salicyclic" should read --salicylic--
column 52 line 52: "Pagets Disease" should read --Paget's disease--
column 52 lines 53-54: "Peronies and Duputren's fibrosis" should read --Peyronie's fibrosis , Dupuytren's fibrosis--
column 53 line 16: "to" should read --not--
column 53 line 56: "Table 4" should read --Table 1--
column 55 line 49: " ethylacetate" should read -- ethyl acetate--
column 56 line 64: "Example 5" should read --Example 13--
column 57 line 27: "Example 9" should read --Example 16--
column 57 lines 34-35: "nitrophenyimino" should read --nitrophenylimino--
column 59 lines 31-32: "Example 19" should read --Example 23--
column 59 line 36: "Table 4" should read --Table 1--
column 60 line 1: "Table 4" should read --Table 1--
column 60 lines 49: "Table 5" should read --Table 2--
column 60 lines 53: "Table 5" should read --Table 2--

IN THE CLAIMS column 62 line 46: "(C1-C6)perfluoroalkylene" should read--$(C_1-C_6)$perfluoroalkylene--
column 63 line 60: "-$(C_2-C_6)$-OH" should read -- -$(C_2-C_6)$alkylene-OH --
column 63 line 63: "-$O(C_2-C_6)$-$N((C_1-C_6)$alkyl$)_2$" should read
-- -$O(C_2-C_6)$alkylene-$N((C_1-C_6)$alkyl$)_2$ --
column 64 line 23: "Trimethoxystyryl" should read --trimethoxystyryl--
column 64 line 24: "methoxy-phenyl" should read --methoxyphenyl--
column 64 line 25: "Trimethoxystyryl" should read --trimethoxystyryl--
column 75 line 48: "-$(C_2-C_6)$-OH" should read -- -$(C_2-C_6)$alkylene-OH --
column 75 line 50: "-$O(C_2-C_6)$-$N((C_1-C_6)$alkyl$)_2$" should read
-- -$O(C_2-C_6)$alkylene-$N((C_1-C_6)$alkyl$)_2$ --

UNITED STATES PATENT AND TRADEMARK OFFICE
CERTIFICATE OF CORRECTION

PATENT NO. : 7,161,031 B2
APPLICATION NO. : 10/505998
DATED : January 9, 2007
INVENTOR(S) : Reddy et al.

It is certified that error appears in the above-identified patent and that said Letters Patent is hereby corrected as shown below:

IN THE CLAIMS (cont'd)

column 78 line 62: "-($C_2$-$C_6$)-OH" should read -- -($C_2$-$C_6$)alkylene-OH --
column 78 line 64: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 81 line 34: "-($C_2$-$C_6$)-OH" should read -- -($C_2$-$C_6$)alkylene-OH --
column 81 line 36: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 83 line 44: "-($C_2$-$C_6$)-OH" should read -- -($C_2$-$C_6$)alkylene-OH --
column 83 line 46: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 85 line 22: "$A^4$ is moiety" should read --$A^4$ is a moiety--
column 87 line 21: "-($C_2$-$C_6$)-OH" should read -- -($C_2$-$C_6$)alkylene-OH --
column 87 line 23: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 89 line 23: "-($C_2$-$C_6$)-OH" should read -- -($C_2$-$C_6$)alkylene-OH --
column 89 line 25: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 91 line 29: "-($C_2$-$C_6$)-OH" should read -- -($C_2$-$C_6$)alkylene-OH --
column 91 line 31: "-O($C_2$-$C_6$)-N(($C_1$-$C_6$)alkyl)$_2$" should read -- -O($C_2$-$C_6$)alkylene-N(($C_1$-$C_6$)alkyl)$_2$ --
column 93 line 20: " Pagets Disease" should read --Paget's disease--
column 93 line 21: "Peronies and Duputren's fibrosis" should read --Peyronie's fibrosis , Dupuytren's fibrosis--

Signed and Sealed this

Third Day of July, 2007

JON W. DUDAS
*Director of the United States Patent and Trademark Office*